US010415050B2

(12) United States Patent
Liedschulte et al.

(10) Patent No.: US 10,415,050 B2
(45) Date of Patent: Sep. 17, 2019

(54) REDUCTION OF NICOTINE TO NORNICOTINE CONVERSION IN PLANTS

(71) Applicant: PHILIP MORRIS PRODUCTS S.A., Neuchatel (CH)

(72) Inventors: Verena Liedschulte, Valangin (CH); Simon Goepfert, Lausanne (CH); Lucien Bovet, La Chaux-de-Fonds (CH); Nicolas Sierro, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 0 days.

(21) Appl. No.: 15/306,172

(22) PCT Filed: May 7, 2015

(86) PCT No.: PCT/EP2015/060124
§ 371 (c)(1),
(2) Date: Oct. 24, 2016

(87) PCT Pub. No.: WO2015/169927
PCT Pub. Date: Nov. 12, 2015

(65) Prior Publication Data
US 2017/0130239 A1    May 11, 2017

(30) Foreign Application Priority Data

May 8, 2014  (EP) ..................................... 14167598
May 9, 2014  (EP) ..................................... 14001645

(51) Int. Cl.
*C12N 15/82*  (2006.01)
*C12N 9/02*   (2006.01)
*C12Q 1/6895* (2018.01)

(52) U.S. Cl.
CPC ....... *C12N 15/8243* (2013.01); *C12N 9/0073* (2013.01); *C12N 15/8218* (2013.01);
(Continued)

(58) Field of Classification Search
CPC .............. C12N 15/8243; C12N 9/0073; C12N 15/102; C12N 15/1027; C12N 15/1031
See application file for complete search history.

(56) References Cited

U.S. PATENT DOCUMENTS 5,810,020 A    9/1998 Northway
6,202,649 B1   3/2001 Williams
(Continued)

FOREIGN PATENT DOCUMENTS

CN      102858983       1/2013
WO      WO 98/58555     12/1998
(Continued)

OTHER PUBLICATIONS

Østergaard, Lars, and Martin F. Yanofsky. "Establishing gene function by mutagenesis in *Arabidopsis thaliana*." The Plant Journal 39. 5 (2004): 682-696 (Year: 2004).*
(Continued)

*Primary Examiner* — Weihua Fan
(74) *Attorney, Agent, or Firm* — Mueting, Raasch & Gebhardt, P.A.

(57) ABSTRACT

The present invention relates to a mutant, non-naturally occurring or transgenic tobacco plant cell comprising: (i) a polynucleotide comprising, consisting or consisting essentially of a sequence encoding a functional nicotine N-demethylase and having at least 95% sequence identity to SEQ ID NO:2; (ii) a polypeptide encoded by the polynucleotide set forth in (i); (iii) a polypeptide comprising, consisting or consisting essentially of a sequence encoding a nicotine N-demethylase and having at least 95% sequence identity to SEQ ID NO:3; or (iv) a construct, vector or expression vector comprising the isolated polynucleotide set forth in (i), and wherein the expression or activity of said nicotine demethylase is reduced as compared to a control tobacco
(Continued)

plant cell in which the expression or activity of said nicotine demethylase has not been reduced.

12 Claims, 3 Drawing Sheets

Specification includes a Sequence Listing.

(52) U.S. Cl.
 CPC ....... *C12Q 1/6895* (2013.01); *C12Q 2600/13* (2013.01); *C12Q 2600/156* (2013.01); *C12Y 114/13* (2013.01)

(56) References Cited

U.S. PATENT DOCUMENTS

| | | | |
|---|---|---|---|
| 7,884,263 B2* | 2/2011 | Dewey | C12N 9/0077 800/285 |
| 8,124,851 B2* | 2/2012 | Dewey | C12N 15/8243 800/317.3 |
| 9,247,706 B2 | 2/2016 | Dewey | |
| 2010/0012137 A1 | 1/2010 | Xu | |

FOREIGN PATENT DOCUMENTS

| WO | WO 2005/116199 | 12/2005 |
|---|---|---|
| WO | WO 2006/091194 | 8/2006 |
| WO | WO 2008/070274 | 6/2008 |
| WO | WO 2009/064771 | 5/2009 |
| WO | WO 2009/074325 | 6/2009 |
| WO | WO 2011/088180 | 7/2011 |
| WO | WO 2012/028309 | 3/2012 |

OTHER PUBLICATIONS

NCBI Reference Sequence: XM_016644847.1. retrieved from www.ncbi.nlm.nih.gov/nuccore/XM_016644847.1?report=genbank. Published in 2016 (Year: 2016).*

PCT Search Report and Written Opinion for PCT/EP2015/060124 dated Jul. 13, 2015 (10 pages).
International Preliminary Report on Patentability for PCT/EP2015/060124 dated Nov. 17, 2016 (7 pages).
Dickerson et al., "A Previously Undescribed Chemical Link Between Smoking and Metabolic Disease", *Proc. Natl. Acad. Sci. USA 99*, 15084-15088 (2002).
Genbank Accession No. L22344.
Genbank Accession No. S78780.
McCallum et al, "Targeted Screening for Induced Mutations", *Nat. Biotechnol.* 18; 455-457 (2000).
Pompon et al., "Yeast Expression of Animal and Plant P450s in Optimized Redox Environments", *Methods Enzymol.* 272: 51-64 (1995).
Siminszky et al., "Conversion of Nicotine to Nornicotine in *Nicotiana Tabacum* is Mediated by CYP82E4, a Cytochrome P450 Monooxygenase," *Proc. Natl. Acad. Sci.*, USA 102: 14919-14924 (2005).
Smith et al., "Total Silencing by Intron-Spliced Hairpin RNAs", *Nature*, 407, 319-320 (2000).
Stemple, "Tilling—A High-Throughout Harvest for Functional Genomics", *Nat. Rev Genet*, 5(2): 145-50 (2004).
Wen et al., "A Novel Approach Obtaining Intron-Containing Hairpin RNA Constructs", *Bioscience, Biotechnology and Biochemistry*, 72, 2, 615-617 (2008).
Wernsman et al., Chapter Seventeen, Tobacco, pp. 669-698. *Cultivar Development Crop Species*, W.H. Fehr (ed), MacMillan Publishing Co., Inc., New York, NY.
Wesley et al., "Construct Design for Efficient, Effective and High-Throughout Gene Silencing in Plants", *Plant. J.*, 27, 581-590 (2001).
Office Action issued in China for Application No. 201580023352.1 dated Jan. 11, 2019 (English translation included).
GenBank, NCBI Reference Sequence XM_016644847.1.

* cited by examiner

REDUCTION OF NICOTINE TO NORNICOTINE CONVERSION IN PLANTS

This application is a U.S. National Stage Application of International Application No. PCT/EP2015/060124, filed May 7, 2015, which was published in English on Nov. 12, 2015, as International Publication No. WO 2015/169927 A1. International Application No. PCT/EP2015/060124 claims priority to European Application No. 14167598.3 filed May 8, 2014 and European Application No. 14001645.2 filed May 9, 2014.

FIELD OF THE INVENTION

The present invention discloses the polynucleotide sequences of a novel variant of nicotine N-demethylase (NND3) from the genus *Nicotiana* and variants, homologues and fragments thereof. The polypeptide sequences and variants, homologues and fragments thereof are also disclosed. The modification of the expression of this gene or the activity of the protein encoded thereby to modulate the levels of one or more tobacco specific nitrosamines (TS-NAs) in a plant cell or a plant is also disclosed.

BACKGROUND OF THE INVENTION

Tobacco specific nitrosamines (TSNAs) are formed primarily during the curing and processing of tobacco leaves. Tobacco curing is a process of physical and biochemical changes that bring out the aroma and flavor of each variety of tobacco. It is believed that the amount TSNA in cured tobacco leaf is dependent on the accumulation of nitrites, which accumulate during the death of the plant cell and are formed during curing by the reduction of nitrates under conditions approaching an anaerobic (oxygen deficient) environment. The reduction of nitrates to nitrites is believed to occur by the action of bacteria on the surface of the leaf under anaerobic conditions, and this reduction is particularly pronounced under certain conditions. Once nitrites are formed, these compounds are believed to combine with various tobacco alkaloids, including pyridine-containing compounds, to form nitrosamines.

The four principal TSNAs, that is, those typically found to be present in the highest concentrations, are N-nitrosonicotine (NNN), 4-(methylnitrosamino)-1-(3-pyridyl)-1-butanone (NNK), N-nitrosoanabasine (NAB) and N-nitrosoanatabine (NAT). Minor compounds, that is, those typically found at significantly lower levels than the principal TSNAs, include 4-(methylnitrosamino) 4-(3-pyridyl) butanal (NNA), 4-(methylnitrosamino)-1-(3-pyridyl)-1-butanol (NNAL), 4-(methylnitrosamino)4-(3-pyridyl)-1-butanol (iso-NNAL), and 4-(methylnitrosamino)-4-(3-pyridyl)-1-butyric acid (iso-NNAC). At least NNN and NNK have been reported to be carcinogenic when applied to animals in laboratory studies.

The primary biochemical mechanism of NNN formation is the N-nitrosation of nornicotine, an alkaloid produced through the N-demethylation of nicotine by the enzyme nicotine N-demethylase. Although nornicotine typically represents <5% of the total alkaloid content in cultivated tobacco, nornicotine levels can dramatically increase by a mechanism termed "conversion" in which plants that accumulate nicotine as their principal alkaloid give rise to progeny that metabolize a large portion (as high as 95%) of leaf nicotine to nornicotine. In individuals that have genetically converted (termed "converters"), N-demethylation of nicotine to nornicotine primarily occurs during senescence and curing. Maintaining low nornicotine levels is desirable because of its well characterised role as the precursor of NNN and also because nornicotine per se may be responsible for unwanted health effects. Dickerson and Janda (2002) *Proc. Natl. Acad. Sci. USA* 99, 15084-15088 demonstrated that nornicotine can induce aberrant glycation of proteins and showed the increased accumulation of modified proteins in the blood plasma of smokers. Furthermore, the same report provided evidence that nornicotine can react covalently with commonly used steroid drugs, such as prednisone, potentially altering both the efficacy and toxicity of these drugs. WO98/58555 describes the treatment of tobacco leaves before or during flue-curing by microwaving for reducing TSNAs. U.S. Pat. No. 5,810,020 describes a process for removing TSNAs from tobacco by contacting the tobacco material with a trapping sink, wherein the trapping sink comprises a select transition metal complex which is readily nitrosated to form a nitrosyl complex with little kinetic or thermodynamic hindrance. U.S. Pat. No. 6,202,649 describes a method of substantially preventing formation of TSNAs by, among other things, curing tobacco in a controlled environment having a sufficient airflow to substantially prevent an anaerobic condition around the vicinity of the tobacco leaf. The controlled environment is provided by controlling one or more curing parameters, such as airflow, humidity, and temperature. However, methods such as these can add considerable cost and time to the production of tobacco and therefore are less likely to be accepted by the tobacco industry. Thus, a need remains for an effective and relatively inexpensive method for reducing TSNAs. Molecular based methods for reducing the levels of TSNAs in plants are highly desirable since they do not require expensive, and often complex, methods to achieve the reduced levels of TSNAs. One such molecular based approach is disclosed in WO2011/088180. Compositions and methods are disclosed in WO2011/088180 for inhibiting the expression or function of a root-specific nicotine demethylase polypeptide (CYP82E10) that is involved in the metabolic conversion of nicotine to nornicotine in the roots of tobacco plants. Nicotine demethylase belongs to the family of the cytochrome P450 monooxygenases (CYP). Other nicotine demethylase genes have been described including CYP82E4 and CYP82E5 which participate in the conversion of nicotine to nornicotine and are described in WO2006091194, WO2008070274 and WO2009064771. The knockout of CYP82E4, CYP82E5 and CYP82E10 is able to reduce conversion of nicotine to nornicotine from 3.2% down to 1.1% in Burley tobacco (see WO 2011088180 A1).

There is a continuing need in the art to further reduce the levels of nornicotine in tobacco plants to further reduce the levels of metabolities of nornicotine (for example, TSNAs—such as NNN) that are formed during curing. The present invention seeks to address this need.

SUMMARY OF THE INVENTION

The inventors have identified a further gene belonging to the nicotine N-demethylase (NND) family in *Nicotiana tabacum*, which is referred to herein as NND3. Although the polypeptide sequence of NND3 shows 94% sequence identity to the known polypeptide sequence of CYP82E4 and 91% sequence identity to the known polypeptide sequence of CYP82E5 and CYP82E10, the expression profile of NND3 in *N. tabacum* is surprisingly different when compared to CYP82E4, CYP82E5 and CYP82E10. As shown in FIG. 1 whilst CYP82E4, CYP82E5, CYP82E10 and NND3 each show expression in flowers and roots, NND3 is not expressed at detectable levels in leaves whereas CYP82E4 shows expression exclusively in senescent leaves and CYP82E5 and CYP82E10 show expression in all leaf types tested. The polynucleotide coding sequence of NND3 encodes a functional nicotine N-demethylase. The gene is set forth in SEQ ID NO: 1 and the polynucleotide coding sequence is set forth in SEQ ID NO: 2. The polypeptide sequence is set forth in SEQ ID NO: 3. By reducing the expression of this gene in tobacco plants a reduced conversion of nicotine to nornicotine may be seen. This can result in reduced levels of nornicotine and metabolites of nornicotine—such as NNN—that are formed during curing. This can result in reduced levels of NNN is smoke from cured tobacco material. The present invention is therefore useful to modulate (eg. reduce) the levels of nornicotine and/or the levels of TSNAs in plants—such as at least NNN. In particular, the present invention may be particularly useful when combined with other methods that are able to reduce the levels of nornicotine and/or TSNAs—such as NNN. Thus, it may, for example, be desirable in certain embodiments to reduce the expression of NND3 together with one or more other nicotine demethylase genes in a tobacco plant. This combination is expected to further reduce the conversion of nicotine to nornicotine, which will further reduce the levels of metabolites formed in the tobacco during curing and when the cured material is smoked. The tobacco products derived from the tobacco plants described herein may find use in methods for reducing the carcinogenic potential of tobacco products, and reducing the exposure of humans to carcinogenic nitrosamines. One or more mutations in a gene encoding NND3 are contemplated, wherein the mutations result in reduced expression or function of NND3. The tobacco plants can further comprise one or more mutations in a gene encoding a CYP82E4 nicotine demethylase and/or one or more mutations in a gene encoding a CYP82E5 nicotine demethylase and/or one or more mutations in a gene encoding a CYP82E4 nicotine demethylase wherein the mutations within these genes result in reduced expression or function of the CYP82E4 and/or CYP82E5 and/or CYP82E10 nicotine demethylase.

ASPECTS AND EMBODIMENTS OF THE INVENTION

Aspects and embodiments of the present invention are set forth in the accompanying claims.

In a first aspect there is described a mutant, non-naturally occurring or transgenic tobacco plant cell comprising: (i) a polynucleotide comprising, consisting or consisting essentially of a sequence encoding a functional nicotine N-demethylase and having at least 95% sequence identity to SEQ ID NO:3; (ii) a polypeptide encoded by the polynucleotide set forth in (i); (iii) a polypeptide comprising, consisting or consisting essentially of a sequence encoding a nicotine N-demethylase and having at least 95% sequence identity to SEQ ID NO:3; or (iv) a construct, vector or expression vector comprising the isolated polynucleotide set forth in (i), and wherein the expression or activity of said nicotine demethylase is reduced as compared to a control tobacco plant cell in which the expression or activity of said nicotine demethylase has not been reduced.

In one embodiment, the tobacco plant cell comprises one or more mutations that reduce the expression or activity of said nicotine demethylase.

In one embodiment, the mutant, non-naturally occurring or transgenic tobacco plant cell further comprises one or more mutations in a gene encoding a CYP82E4 nicotine demethylase, wherein said mutation results in reduced expression or function of said CYP82E4 nicotine demethylase, preferably, wherein said CYP82E4 nicotine demethylase is selected from the group consisting of SEQ ID NOs: 12 to 16 or a combination of two or more thereof, preferably, wherein said mutation results in a modification of said CYP82E4 nicotine demethylase and occurs at a position selected from the group consisting of amino acid residues 329, 364, 376, 382, and 458 of SEQ ID NO: 5 or a combination of two or more thereof, preferably, wherein said mutation is selected from the group consisting of: a) a stop codon substitution for the tryptophan residue at position 329 of SEQ ID NO: 5; b) an asparagine substitution for the lysine residue at position 364 of SEQ ID NO: 5; c) a methionine substitution for the valine residue at position 376 of SEQ ID NO: 5; d) a serine substitution for the proline residue at position 382 of SEQ ID NO: 5; d) a serine substitution for the proline residue at position 458 of SEQ ID NO: 5; and e) any combination of two or more thereof.

In one embodiment, the mutant, non-naturally occurring or transgenic tobacco plant cell further comprises one or more mutations in a gene encoding a CYP82E5 nicotine demethylase, wherein said mutation results in reduced expression or function of said CYP82E5 nicotine demethylase, preferably, wherein said CYP82E5 nicotine demethylase is selected from SEQ ID NO: 24 or 25 or a combination thereof, preferably, wherein said mutation results in a modification of said CYP82E5 nicotine demethylase and occurs at amino acid residues 422 or 449 of SEQ ID NO: 17 or a combination thereof, preferably, wherein said mutation is selected from the group consisting of: a) a stop codon substituted for the tryptophan residue at position 422 of SEQ ID NO: 17; b) a leucine substituted for the proline residue at position 449 of SEQ ID NO: 17; and c) a combination thereof.

In one embodiment, the mutant, non-naturally occurring or transgenic tobacco plant cell further comprises one or more mutations in a gene encoding a CYP82E10 nicotine demethylase, wherein said mutation results in reduced expression or function of said CYP82E10 nicotine demethylase, preferably, wherein said CYP82E10 nicotine demethylase is selected from the group consisting of SEQ ID NOs: 32 to 35 or a combination of two or more thereof, preferably, wherein said mutation results in a modification of said CYP82E10 nicotine demethylase and occurs at a position selected from the group consisting of amino acid residues 79, 107, 382, 419 of SEQ ID NO: 26 or a combination of two or more thereof, preferably, wherein said mutation is selected from the group consisting of: a) a serine substitution for the glycine residue at position 79 of SEQ ID NO: 26; b) a serine substitution for the proline residue at position 107 of SEQ ID NO: 26; c) a serine substitution for the proline residue at position 382 of SEQ ID NO: 26; d) a serine substitution for the proline residue at position 419 of SEQ ID NO: 26; and e) any combination thereof.

In one embodiment, the mutant, non-naturally occurring or transgenic tobacco plant cell further comprises: (i) one or more mutations in a gene encoding a CYP82E4 nicotine demethylase, wherein said mutation results in reduced expression or function of said CYP82E4 nicotine demethylase, preferably, wherein said CYP82E4 nicotine demethylase is selected from the group consisting of SEQ ID NOs: 12 to 16 or a combination of two or more thereof, preferably, wherein said mutation results in a modification of said CYP82E4 nicotine demethylase and occurs at a position selected from the group consisting of amino acid residues 329, 364, 376, 382, and 458 of SEQ ID NO:5 or a combination of two or more thereof, preferably, wherein said mutation is selected from the group consisting of: a) a stop codon substitution for the tryptophan residue at position 329 of SEQ ID NO: 5; b) an asparagine substitution for the lysine residue at position 364 of SEQ ID NO: 5; c) a methionine substitution for the valine residue at position 376 of SEQ ID NO: 5; d) a serine substitution for the proline residue at position 382 of SEQ ID NO: 5; d) a serine substitution for the proline residue at position 458 of SEQ ID NO: 5; and e) any combination of two or more thereof; and (ii) one or more mutations in a gene encoding a CYP82E5 nicotine demethylase, wherein said mutation results in reduced expression or function of said CYP82E5 nicotine demethylase, preferably, wherein said CYP82E5 nicotine demethylase is selected from SEQ ID NO: 24 or 25 or a combination thereof, preferably, wherein said mutation results in a modification of said CYP82E5 nicotine demethylase and occurs at amino acid residues 422 or 449 of SEQ ID NO: 17 or a combination thereof, preferably, wherein said mutation is selected from the group consisting of: a) a stop codon substituted for the tryptophan residue at position 422 of SEQ ID NO: 17; b) a leucine substituted for the proline residue at position 449 of SEQ ID NO: 17; and c) a combination thereof; and (iii) one or more mutations in a gene encoding a CYP82E10 nicotine demethylase, wherein said mutation results in reduced expression or function of said CYP82E10 nicotine demethylase, preferably, wherein said CYP82E10 nicotine demethylase is selected from the group consisting of SEQ ID NOs: 32 to 35 or a combination of two or more thereof, preferably, wherein said mutation results in a modification of said CYP82E10 nicotine demethylase and occurs at a position selected from the group consisting of amino acid residues 79, 107, 382, 419 of SEQ ID NO: 26 or a combination of two or more thereof, preferably, wherein said mutation is selected from the group consisting of: a) a serine substitution for the glycine residue at position 79 of SEQ ID NO: 26; b) a serine substitution for the proline residue at position 107 of SEQ ID NO: 26; c) a serine substitution for the proline residue at position 382 of SEQ ID NO: 26; d) a serine substitution for the proline residue at position 419 of SEQ ID NO: 26; and e) any combination thereof.

In one embodiment, the mutant, non-naturally occurring or transgenic tobacco plant cell further comprises (i) one or more mutations in a gene encoding a CYP82E4 nicotine demethylase, one or more mutations in a gene encoding a CYP82E5 nicotine demethylase and one or more mutations in a gene encoding a CYP82E10 nicotine demethylase, wherein said CYP82E4 nicotine demethylase comprises the sequence set forth in SEQ ID NO: 13 (W329Stop), said CYP82E5 nicotine demethylase comprises the sequence set forth in SEQ ID NO: 24 (W422Stop), and said CYP82E10 nicotine demethylase comprises the sequence set forth in SEQ ID NO: 33 (G79S); or (ii) one or more mutations in a gene encoding a CYP82E4 nicotine demethylase, one or more mutations in a gene encoding a CYP82E5 nicotine demethylase and one or more mutations a gene encoding a CYP82E10 nicotine demethylase, wherein said CYP82E4 nicotine demethylase comprises the sequence set forth in SEQ ID NO: 13 (W329Stop), said CYP82E5 nicotine demethylase comprises the sequence set forth in SEQ ID NO: 24 (W422Stop), and said CYP82E10 nicotine demethylase comprises the sequence set forth in SEQ ID NO: 34 (P107S); or (iii) one or more mutations in a gene encoding a CYP82E4 nicotine demethylase, one or more mutations in a gene encoding a CYP82E5 nicotine demethylase and one or more mutations in a gene encoding a CYP82E10 nicotine demethylase, wherein said CYP82E4 nicotine demethylase comprises the sequence set forth in SEQ ID NO: 13 (W329Stop), said CYP82E5 nicotine demethylase comprises the sequence set forth in SEQ ID NO: 24 (W422Stop), and said CYP82E10 nicotine demethylases comprise the sequence set forth in SEQ ID NO: 35 (P382S); or (iv) one or more mutations in a gene encoding a CYP82E4 nicotine demethylase, one or more mutations in a gene encoding a CYP82E5 nicotine demethylase and one or more mutations in a gene encoding a CYP82E10 nicotine demethylase, wherein said CYP82E4 nicotine demethylase comprises the sequence set forth in SEQ ID NO: 13 (W329Stop), said CYP82E5 nicotine demethylase comprises the sequence set forth in SEQ ID NO: 24 (W422Stop), and said CYP82E10 nicotine demethylase comprises the sequence set forth in SEQ ID NO: 32 (P419S).

In one embodiment, said mutation(s) is a homozygous mutation.

In one embodiment, said plant cell or plant comprising said plant cell has less than about 1.0%, less than about 0.9%, less than about 0.8%, less than about 0.7%, less than about 0.6%, less than about 0.5%, less than about 0.4%, less than about 0.3%, less than about 0.2% or less than about 0.1% conversion of nicotine to nornicotine. The % conversion is calculated using the equation [% nornicotine/(% nornicotine+% nicotine)]×100.

In one embodiment, said plant cell or plant comprising said plant cell has less than about 0.04%, less than about 0.03%, less than about 0.02% or less than about 0.01% nornicotine, calculated on a dry weight basis.

In a further aspect there is described a mutant, non-naturally occurring or transgenic plant comprising the plant cell described herein.

In a further aspect there is described plant material including biomass, seed, stem or leaves from the plant described herein. Suitably, NND3 is expressed in flowers (for example, immature flower, mature flower, immature capsule, dry capsule) and roots of the plant material. Suitably, NND3 is expressed exclusively or specifically in flowers (for example, immature flower, mature flower, immature capsule, dry capsule) and roots of the plant material.

In a further aspect there is described a tobacco product comprising the plant cell, the plant or the plant material described herein.

In a further aspect there is described a method for preparing a tobacco plant with reduced levels of nornicotine and/or NNN, said method comprising the steps of: (a) providing a plant comprising (i) a polynucleotide comprising, consisting or consisting essentially of a sequence encoding a (functional) nicotine N-demethylase and having at least 95% sequence identity to SEQ ID NO:2; (b) inserting one or more mutations into said polynucleotide of said tobacco plant to create a mutant tobacco plant; (c) optionally curing the tobacco plant material; and (d) measuring the level of nornicotine and/or NNN in the mutant tobacco plant, wherein a decrease in the level of nornicotine and/or NNN in the mutant tobacco plant as compared to a control tobacco plant is indicative that the levels of nornicotine and/or NNN in said mutant tobacco plant have been reduced. The use of fragments of the sequences described herein is also contemplated. For example, the fragments can be used as RNAi constructs to modulate expression.

In one embodiment, the tobacco plant in step (b) is a mutant tobacco plant, preferably, wherein said mutant tobacco plant comprises one or more mutations in one or more further nicotine N-demethylase genes.

In one embodiment, said mutant tobacco plant has one or more further mutations in the genes consisting of the group of CYP82E4, CYP82E5 or CYP82E10 or a combination of two or more thereof.

In one embodiment, the tobacco plant in step (b) is a mutant tobacco plant which has reduced levels of nornicotine as compared to a control tobacco plant.

In one embodiment, said tobacco plant has one or more mutations in CYP82E4, CYP82E5 or CYP82E10 or a combination of two or more thereof.

In a further aspect there is described a method for identifying one or more mutations in a tobacco plant that correlate with low levels of nornicotine and/or NNN, said method comprising the steps of: (a) identifying a tobacco plant with low levels of nornicotine and/or NNN as compared to a control tobacco plant; (b) providing a nucleic acid sample from the tobacco plant identified in step (a); (c) screening the nucleic acid sample from step (b) for the presence of one or more mutations in the sequence of SEQ ID NO: 2 that are not present in the control plant; (d) optionally comparing the one or more mutations identified in step (c) with known mutations that reduce the levels of nornicotine and/or NNN in a tobacco plant; and (e) identifying those one or more mutations which correlate with low levels of nornicotine and/or NNN.

In a further aspect there is described a method for producing cured plant material, preferably cured leaves, with reduced levels of nornicotine and/or at least NNN therein comprising the steps of: (a) providing at least part of a plant or the plant material described herein; (b) optionally harvesting the plant material therefrom; and (c) curing the plant material for a period of time sufficient for the levels of nornicotine and/or at least NNN to decrease therein.

In a further aspect there is described a tobacco plant comprising one or more mutations in a gene encoding a NND3 nicotine demethylase, one or more mutations in a gene encoding a CYP82E10 nicotine demethylase, one or more mutations in a gene encoding a CYP82E4 nicotine demethylase, and one or more mutations in a gene encoding a CYP82E5 nicotine demethylase, optionally wherein said CYP82E10 nicotine demethylase comprises a mutation at position 382 of SEQ ID NO: SEQ ID NO: 26, said CYP82E4 nicotine demethylase comprises a mutation at position 329 of SEQ ID NO: 5, and said CYP82E5 nicotine demethylase comprises a mutation at position 422 of SEQ ID NO: 17, preferably, wherein each of said mutations is a homozygous mutation.

In a further aspect there is described a tobacco plant comprising one or more mutations in a NND3 gene that inhibits nicotine demethylase activity in flowers (for example, immature flower, mature flower, immature capsule, dry capsule) and roots, one or more mutations in a CYP82E10 gene that inhibits nicotine demethylase activity in roots and/or leaves, one or more mutations in a CYP82E4v2 gene that inhibits nicotine demethylase activity in senescent leaves, and one or more mutations in a CYP83E5v2 gene that inhibits nicotine demethylase activity in roots and/or leaves.

In a further aspect there is described an isolated polynucleotide sequence comprising, consisting or consisting essentially of a sequence encoding a NND3 nicotine N-demethylase and having the sequence of SEQ ID NO:2, or at least 95% sequence identity to SEQ ID NO:2, preferably wherein said isolated polynucleotide is a synthetic polynucleotide or cDNA.

In a further aspect there is described an isolated polypeptide encoded by the polynucleotide described herein.

In a further aspect there is described an isolated polypeptide comprising, consisting or consisting essentially of a sequence encoding a NND3 nicotine N-demethylase and having the sequence of SEQ ID NO:3, or at least 95% sequence identity to SEQ ID NO:3, preferably wherein said isolated polypeptide is a synthetic polypeptide. Fragments of the polypeptide are also contemplated as described herein.

In a further aspect there is described a construct, vector or expression vector comprising the isolated polynucleotide described herein.

In a further aspect there is described a mutation in a gene encoding a NND3 nicotine demethylase, wherein said mutation results in reduced expression or function of said NND3 nicotine demethylase.

In a further aspect, there is described a method for reducing the level of nornicotine, or reducing the rate of conversion of nicotine to nornicotine, or reducing the level of at least NNN in a tobacco plant cell comprising the steps of: (a) reducing the expression or activity of: (i) a polynucleotide comprising, consisting or consisting essentially of a sequence encoding a nicotine N-demethylase and having at least 95% sequence identity to SEQ ID NO:2; (ii) a polypeptide encoded by the polynucleotide set forth in (i); (iii) a polypeptide comprising, consisting or consisting essentially of a sequence encoding a nicotine N-demethylase and having at least 95% sequence identity to SEQ ID NO:3; (b) measuring at least the nornicotine and/or NNN content in the plant cell obtained in step (a); and (c) identifying a plant cell in which at least the nornicotine and/or NNN content therein has changed in comparison to a control plant in which the expression or activity of the polynucleotide or polypeptide set forth in (a) has not been modulated.

In a further aspect, there is provided a method for reducing a carcinogenic potential of a tobacco product, said method comprising preparing said tobacco product from a tobacco plant or progeny thereof as described herein.

In a further aspect, there is provided a method of reducing the level of nornicotine, or reducing the rate of conversion of nicotine to nornicotine, or reducing the level of at least NNN in a tobacco plant, said method comprising introducing into the genome of said plant one or more mutations within at least one allele of the NND3 nicotine demethylase gene, wherein said mutation reduces expression of said nicotine demethylase gene.

In one embodiment, NND3 is expressed in flowers (for example, immature flower, mature flower, immature capsule, dry capsule) and roots.

In one embodiment, NND3 is expressed exclusively or specifically in flowers (for example, immature flower, mature flower, immature capsule, dry capsule) and roots.

Each of the embodiments discussed above are disclosed as embodiments of each of the aspects of the invention. Combinations of one or more of the embodiments are also contemplated.

DEFINITIONS

Figure 1:
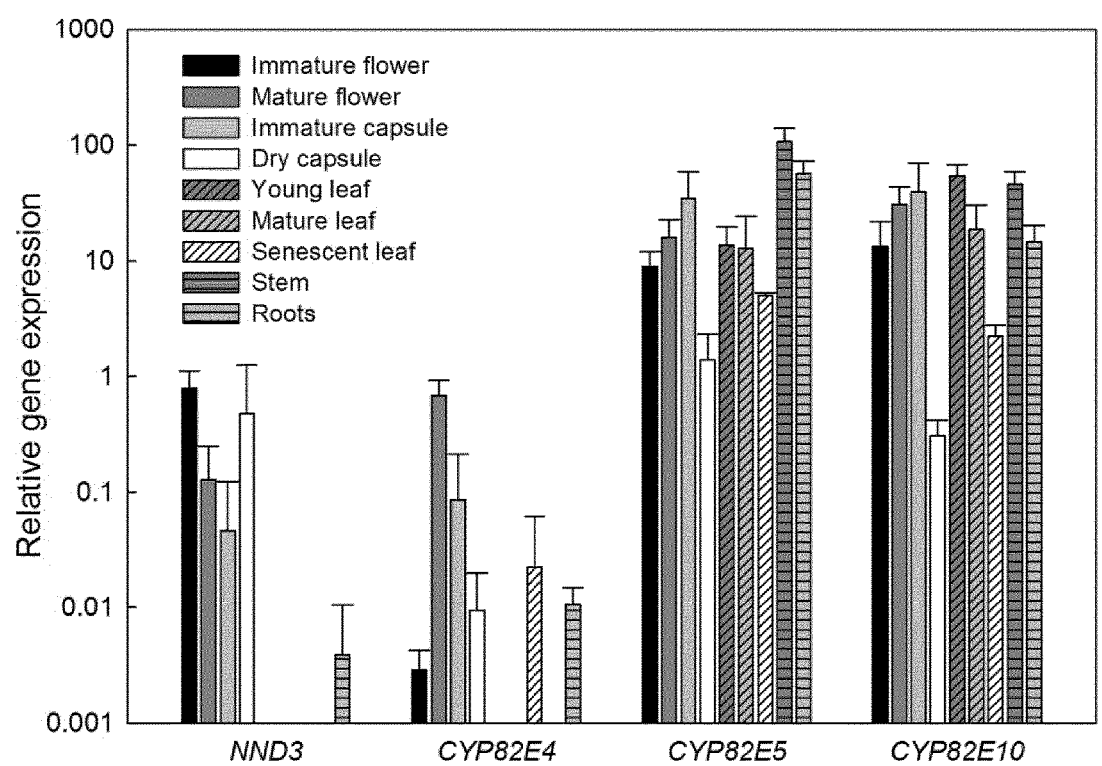
FIG. 1 shows the relative expression levels of NND3 and related functional CYP82E genes in different plant tissues. Bars indicate mean±SD of three biological replicates taken from three greenhouse grown mature *N. tabacum* var. TN90 plants.

The technical terms and expressions used within the scope of this application are generally to be given the meaning commonly applied to them in the pertinent art of plant and molecular biology. All of the following term definitions apply to the complete content of this application. The word "comprising" does not exclude other elements or steps, and the indefinite article "a" or "an" does not exclude a plurality. A single step may fulfil the functions of several features recited in the claims. The terms "about", "essentially" and "approximately" in the context of a given numerate value or range refers to a value or range that is within 20%, within 10%, or within 5%, 4%, 3%, 2% or 1% of the given value or range.

The term "isolated" refers to any entity that is taken from its natural milieu, but the term does not connote any degree of purification.

An "expression vector" is a nucleic acid vehicle that comprises a combination of nucleic acid components for enabling the expression of nucleic acid. Suitable expression vectors include episomes capable of extra-chromosomal replication such as circular, double-stranded nucleic acid plasmids; linearized double-stranded nucleic acid plasmids; and other functionally equivalent expression vectors of any origin. An expression vector comprises at least a promoter positioned upstream and operably-linked to a nucleic acid, nucleic acid constructs or nucleic acid conjugate, as defined below.

The term "construct" refers to a double-stranded, recombinant nucleic acid fragment comprising one or more polynucleotides. The construct comprises a "template strand" base-paired with a complementary "sense or coding strand." A given construct can be inserted into a vector in two possible orientations, either in the same (or sense) orientation or in the reverse (or anti-sense) orientation with respect to the orientation of a promoter positioned within a vector—such as an expression vector.

A "vector" refers to a nucleic acid vehicle that comprises a combination of nucleic acid components for enabling the transport of nucleic acid, nucleic acid constructs and nucleic acid conjugates and the like. Suitable vectors include episomes capable of extra-chromosomal replication such as circular, double-stranded nucleic acid plasmids; linearized double-stranded nucleic acid plasmids; and other vectors of any origin.

A "promoter" refers to a nucleic acid element/sequence, typically positioned upstream and operably-linked to a double-stranded DNA fragment. Promoters can be derived entirely from regions proximate to a native gene of interest, or can be composed of different elements derived from different native promoters or synthetic DNA segments.

The terms "homology, identity or similarity" refer to the degree of sequence similarity between two polypeptides or between two nucleic acid molecules compared by sequence alignment.

The degree of homology between two discrete nucleic acid sequences being compared is a function of the number of identical, or matching, nucleotides at comparable positions. The percent identity may be determined by visual inspection and mathematical calculation. Alternatively, the percent identity of two nucleic acid sequences may be determined by comparing sequence information using a computer program such as—ClustalW, BLAST, FASTA or Smith-Waterman.

A "variant" means a substantially similar sequence. A variant can have a similar function or substantially similar function as a wild-type sequence. For a nicotine demethylase, a similar function is at least about 50%, 60%, 70%, 80% or 90% of wild-type enzyme function of converting nicotine to nornicotine under the same conditions. For a nicotine demethylase, a substantially similar function is at least about 90%, 95%, 96%, 97%, 98% or 99% of wild-type enzyme function of converting nicotine to nornicotine under the same conditions. For example, wild-type NND3 coding sequence is set forth in SEQ ID NO: 2. The variants can have one or more favourable mutations that result in the enzyme having a reduced level of nicotine demethylase activity as compared to the wild-type polypeptide. The variants can have one or more favourable mutations that result in their nicotine demethylase activity being knocked out (ie. a 100% inhibition, and thus a non-functional polypeptide). Exemplary variants of wild-type CYP82E10 include CYP82E10 P419S which has a favourable mutation that results in the enzyme having only about 25% of the nicotine demethylase activity of the wild-type CYP82E10 polypeptide. The variants CYP82E10 G79S, CYP82E10 P107S and CYP82E10 P382S have favourable mutations that result in their nicotine demethylase activity being knocked out (ie. a 100% inhibition, and thus a non-functional polypeptide). Exemplary variants of wild-type CYP82E4 include CYP82E4 V376M which has a favourable mutation that results in the enzyme having only about 50% of the nicotine demethylase activity of the wild-type CYP82E4 polypeptide. The variants CYP82E4 W329Stop, CYP82E4 K364N, CYP82E4 P382S and CYP82E4 P458S have favourable mutations that result in their nicotine demethylase activity being knocked out (i.e. 100% inhibition, and thus a non-functional polypeptide). Exemplary variants of wild-type CYP82E5 include CYP82E5 P449L which has a favourable mutation that results in inhibition of its nicotine demethylase activity, and the variant CYP82E5 W22Stop has a favourable mutation that results in its nicotine demethylase activity being knocked out (i.e., 100% inhibition, and thus a non-functional polypeptide). Combinations of these variants are disclosed herein.

The term "plant" refers to any plant or part of a plant at any stage of its life cycle or development, and its progenies. In one embodiment, the plant is a "tobacco plant", which refers to a plant belonging to the genus *Nicotiana*. Preferred species of tobacco plant are described herein.

"Plant parts" include plant cells, plant protoplasts, plant cell tissue cultures from which a whole plant can be regenerated, plant calli, plant clumps and plant cells that are intact in plants or parts of plants such as embryos, pollen, anthers, ovules, seeds, leaves, flowers, stems, branches, fruit, roots, root tips and the like. Progeny, variants and mutants of regenerated plants are also included within the scope of the disclosure, provided that they comprise the introduced polynucleotides described herein.

A "plant cell" refers to a structural and physiological unit of a plant. The plant cell may be in the form of a protoplast without a cell wall, an isolated single cell or a cultured cell, or as a part of higher organized unit such as but not limited to, plant tissue, a plant organ, or a whole plant.

The term "plant material" refers to any solid, liquid or gaseous composition, or a combination thereof, obtainable from a plant, including biomass, leaves, stems, roots, flowers or flower parts, fruits, pollen, egg cells, zygotes, seeds, cuttings, secretions, extracts, cell or tissue cultures, or any other parts or products of a plant. In one embodiment, the plant material comprises or consists of biomass, stem, seed or leaves. In another embodiment, the plant material comprises or consists of leaves.

The term "variety" refers to a population of plants that share constant characteristics which separate them from other plants of the same species. While possessing one or more distinctive traits, a variety is further characterized by a very small overall variation between individuals within that variety. A variety is often sold commercially.

The term "line" or "breeding line" as used herein denotes a group of plants that are used during plant breeding. A line is distinguishable from a variety as it displays little variation between individuals for one or more traits of interest, although there may be some variation between individuals for other traits.

The term "modulating" may refer to reducing, inhibiting, increasing or otherwise affecting the expression or activity of a polypeptide. The term may also refer to reducing, inhibiting, increasing or otherwise affecting the activity of a gene encoding a polypeptide which can include, but is not limited to, modulating transcriptional activity.

The term "reduce" or "reduced" as used herein, refers to a reduction of from about 10% to about 99%, or a reduction of at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "inhibit" or "inhibited" as used herein, refers to a reduction of from about 98% to about 100%, or a reduction of at least 98%, at least 99%, but particularly of 100%, of a quantity or an activity, such as but not limited to polypeptide activity, transcriptional activity and protein expression.

The term "increase" or "increased" as used herein, refers to an increase of from about 5% to about 99%, or an increase of at least 5%, at least 10%, at least 20%, at least 25%, at least 30%, at least 40%, at least 50%, at least 60%, at least 70%, at least 75%, at least 80%, at least 90%, at least 95%, at least 98%, at least 99%, or at least 100% or more of a quantity or an activity, such as but not limited to polypeptide activity, transcriptional activity and protein expression.

The term "control" in the context of a control plant means a plant or plant cell in which the expression or activity of an enzyme has not been modified (for example, increased or reduced) and so it can provide a comparison with a plant in which the expression or activity of the enzyme has been modified. The control plant may comprise an empty vector. The control plant or plant cell may correspond to a wild-type plant or wild-type plant cell. For example, the control plant or plant cell can be the same genotype as the starting material for the genetic alteration that resulted in the subject plant. In all such cases, the subject plant and the control plant are cultured and harvested using the same protocols for comparative purposes. Changes in levels, ratios, activity, or distribution of the genes or polypeptides described herein, or changes in tobacco plant phenotype, particularly reduced accumulation of nornicotine and its carcinogenic metabolite, NNN, can be measured by comparing a subject plant to the control plant, where the subject plant and the control plant have been cultured and/or harvested using the same protocols. The control plant can provide a reference point for measuring changes in phenotype of the subject plant. The measurement of changes in phenotype can be measured at any time in a plant, including during plant development, senescence, or after curing. Measurement of changes in phenotype can be measured in plants grown under any conditions, including from plants grown in growth chamber, greenhouse, or in a field. Changes in phenotype can be measured by determining the nicotine to nornicotine conversion rate. Conversion can be measured by dividing the percentage of nornicotine or metabolite thereof (as a percentage of the total tissue weight) by the sum of the percentage nicotine and nornicotine or metabolite thereof (as percentages of the total tissue weight) and multiplying by 100. Changes in phenotype can be measured by measuring TSNA content—such as at least the NNN content using methods that are well known in the art.

DETAILED DESCRIPTION

In one embodiment, there is provided an isolated polynucleotide comprising, consisting or consisting essentially of a polynucleotide sequence having at least 95% sequence identity to any of the sequences described herein, including any of polynucleotides shown in the sequence listing. Suitably, the isolated polynucleotide comprises, consists or consists essentially of a sequence having at least 95%, 96%, 97%, 98%, 99% or 100% sequence identity thereto.

In another embodiment, there is provided an isolated polynucleotide comprising, consisting or consisting essentially of a polynucleotide sequence having at least 95% sequence identity to SEQ ID NO:2. Suitably, the isolated polynucleotide comprises, consists or consist essentially of a sequence having at least about 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO:2.

In another embodiment, there is provided a polynucleotide comprising, consisting or consisting essentially of a polynucleotide with substantial homology (that is, sequence similarity) or substantial identity to SEQ ID NO:2.

In another embodiment, there is provided polynucleotide variants that have at least about 95%, 95% 96%, 97%, 98%, 99%, 99.1%, 99.2%, 99.3%, 99.4%, 99.5%, 99.6%, 99.7%, 99.8% or 99.9% sequence identity to the sequence of SEQ ID NO:2.

In another embodiment, there is provided fragments of SEQ ID NO:2 with substantial homology (that is, sequence similarity) or substantial identity thereto that have at least about 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO:2.

Preferably, the fragments have the stated sequence identity over a stretch of at least 15 contiguous nucleotides of SEQ ID NO:1. In embodiments, the sequence identity extends over at least 20, 25, 30, 35, 40, 45, 50 or more contiguous nucleotides.

In another embodiment, there is provided polynucleotides comprising a sufficient or substantial degree of identity or similarity to SEQ ID NO:2 that encodes a polypeptide that functions as a nicotine N-demethylase. Suitably, the polynucleotide(s) described herein encode a protein with nicotine N-demethylase activity that is at least about 50%, 60%, 70%, 80%, 90% 95%, 96%, 97%, 98%, 99% or 100% or more of the activity of the protein set forth in SEQ ID NO:3.

To determine if a polypeptide is a functional nicotine demethylase, its cDNA can be cloned into an expression vector and transformed into a yeast strain—such as strain W(R). Strain W(R) is a yeast cell line that has been engineered to overexpress the yeast NADPH-dependent P450 reductase, an enzyme that serves as the direct electron donor to P450s; this system enhances the detection of foreign P450 enzyme activities that are expressed in yeast (Pompon et al., (1995) *Methods Enzymol.* 272: 51-64). Nicotine demethylase assays can be conducted by incubating yeast microsomal membrane preparations with [$^{14}$C]-nicotine, and resolving the products by thin layer chromatography as described in Siminszky et al. (2005) *Proc. Natl. Acad. Sci.* USA 102: 14919-14924.

A polynucleotide as described herein can include a polymer of nucleotides, which may be unmodified or modified deoxyribonucleic acid (DNA) or ribonucleic acid (RNA). Accordingly, a polynucleotide can be, without limitation, a genomic DNA, complementary DNA (cDNA), mRNA, or antisense RNA or a fragment(s) thereof. Moreover, a polynucleotide can be single-stranded or double-stranded DNA, DNA that is a mixture of single-stranded and double-stranded regions, a hybrid molecule comprising DNA and RNA, or a hybrid molecule with a mixture of single-stranded and double-stranded regions or a fragment(s) thereof. In addition, the polynucleotide can be composed of triple-stranded regions comprising DNA, RNA, or both or a fragment(s) thereof. A polynucleotide can contain one or more modified bases, such as phosphothioates, and can be a peptide nucleic acid. Generally, polynucleotides can be assembled from isolated or cloned fragments of cDNA, genomic DNA, oligonucleotides, or individual nucleotides, or a combination of the foregoing. Although the polynucleotide sequences described herein are shown as DNA sequences, the sequences include their corresponding RNA sequences, and their complementary (for example, completely complementary) DNA or RNA sequences, including the reverse complements thereof.

A polynucleotide as described herein will generally contain phosphodiester bonds, although in some cases, polynucleotide analogues are included that may have alternate backbones, comprising, for example, phosphoramidate, phosphorothioate, phosphorodithioate, or O-methylphophoroamidite linkages; and peptide polynucleotide backbones and linkages. Other analogue polynucleotides include those with positive backbones; non-ionic backbones, and non-ribose backbones. Modifications of the ribose-phosphate backbone may be done for a variety of reasons, for example, to increase the stability and half-life of such molecules in physiological environments or as probes on a biochip. Mixtures of naturally occurring polynucleotides and analogues can be made; alternatively, mixtures of different polynucleotide analogues, and mixtures of naturally occurring polynucleotides and analogues may be made.

A variety of polynucleotide analogues are known, including, for example, phosphoramidate, phosphorothioate, phosphorodithioate, O-methylphophoroamidite linkages and peptide polynucleotide backbones and linkages. Other analogue polynucleotides include those with positive backbones, non-ionic backbones and non-ribose backbones. Polynucleotides containing one or more carbocyclic sugars are also included.

Other analogues include peptide polynucleotides which are peptide polynucleotide analogues. These backbones are substantially non-ionic under neutral conditions, in contrast to the highly charged phosphodiester backbone of naturally occurring polynucleotides. This may result in advantages. First, the peptide polynucleotide backbone may exhibit improved hybridization kinetics. Peptide polynucleotides have larger changes in the melting temperature for mismatched versus perfectly matched base pairs. DNA and RNA typically exhibit a 2-4° C. drop in melting temperature for an internal mismatch. With the non-ionic peptide polynucleotide backbone, the drop is closer to 7-9° C. Similarly, due to their non-ionic nature, hybridization of the bases attached to these backbones is relatively insensitive to salt concentration. In addition, peptide polynucleotides may not be degraded or degraded to a lesser extent by cellular enzymes, and thus may be more stable.

Among the uses of the disclosed polynucleotides, and fragments thereof, is the use of fragments as probes in nucleic acid hybridisation assays or primers for use in nucleic acid amplification assays. Such fragments generally comprise at least about 10, 11, 12, 13, 14, 15, 16, 17, 18, 19 or 20 or more contiguous nucleotides of a DNA sequence. In other embodiments, a DNA fragment comprises at least about 10, 15, 20, 30, 40, 50 or 60 or more contiguous nucleotides of a DNA sequence. Thus, in one aspect, there is also provided a method for detecting a polynucleotide encoding a protein with nicotine N-demethylase activity member or encoding a nicotine N-demethylase enzyme comprising the use of the probes or primers or both.

The basic parameters affecting the choice of hybridization conditions and guidance for devising suitable conditions are described by Sambrook, J., E. F. Fritsch, and T. Maniatis (1989, Molecular Cloning: A Laboratory Manual, Cold Spring Harbor Laboratory Press, Cold Spring Harbor, N.Y.). Using knowledge of the genetic code in combination with the amino acid sequences described herein, sets of degenerate oligonucleotides can be prepared. Such oligonucleotides are useful as primers, for example, in polymerase chain reactions (PCR), whereby DNA fragments are isolated and amplified. In certain embodiments, degenerate primers can be used as probes for genetic libraries. Such libraries would include but are not limited to cDNA libraries, genomic libraries, and even electronic express sequence tag or DNA libraries. Homologous sequences identified by this method would then be used as probes to identify homologues of the sequences identified herein.

Also of potential use are polynucleotides and oligonucleotides (for example, primers or probes) that hybridize under reduced stringency conditions, typically moderately stringent conditions, and commonly highly stringent conditions to the polynucleotide(s) as described herein. The basic parameters affecting the choice of hybridization conditions and guidance for devising suitable conditions are set forth by Sambrook, J., E. F. Fritsch, and T. Maniatis (1989, Molecular Cloning: A Laboratory Manual, Cold Spring Harbor Laboratory Press, Cold Spring Harbor, N.Y. and can be readily determined by those having ordinary skill in the art based on, for example, the length or base composition of the polynucleotide. One way of achieving moderately stringent conditions involves the use of a prewashing solution containing 5× Standard Sodium Citrate, 0.5% Sodium Dodecyl Sulphate, 1.0 mM Ethylenediaminetetraacetic acid (pH 8.0), hybridization buffer of about 50% formamide, 6× Standard Sodium Citrate, and a hybridization temperature of about 55° C. (or other similar hybridization solutions, such as one containing about 50% formamide, with a hybridization temperature of about 42° C.), and washing conditions of about 60° C., in 0.5× Standard Sodium Citrate, 0.1% Sodium Dodecyl Sulphate. Generally, highly stringent conditions are defined as hybridization conditions as above, but with washing at approximately 68° C., 0.2× Standard Sodium Citrate, 0.1% Sodium Dodecyl Sulphate. SSPE (1×SSPE is 0.15 M sodium chloride, 10 mM sodium phosphate, and 1.25 mM Ethylenediaminetetraacetic acid, pH 7.4) can be substituted for Standard Sodium Citrate (1× Standard Sodium Citrate is 0.15 M sodium chloride and 15 mM sodium citrate) in the hybridization and wash buffers; washes are performed for 15 minutes after hybridization is complete. It should be understood that the wash temperature and wash salt concentration can be adjusted as necessary to achieve a desired degree of stringency by applying the basic principles that govern hybridization reactions and duplex stability, as known to those skilled in the art and described further below (see, for example, Sambrook, J., E. F. Fritsch, and T. Maniatis (1989, Molecular Cloning: A Laboratory Manual, Cold Spring Harbor Laboratory Press, Cold Spring Harbor, N.Y.). When hybridizing a polynucleotide to a target polynucleotide of unknown sequence, the hybrid length is assumed to be that of the hybridizing polynucleotide. When polynucleotides of known sequence are hybridized, the hybrid length can be determined by aligning the sequences of the polynucleotides and identifying the region or regions of optimal sequence complementarity. The hybridization temperature for hybrids anticipated to be less than 50 base pairs in length should be 5 to 10° C. less than the melting temperature of the hybrid, where melting temperature is determined according to the following equations. For hybrids less than 18 base pairs in length, melting temperature (° C.)=2(number of A+T bases)+4(number of G+C bases). For hybrids above 18 base pairs in length, melting temperature (° C.)=81.5+16.6(log 10 [Na+])+0.41(% G+C)−(600/N), where N is the number of bases in the hybrid, and [Na+] is the concentration of sodium ions in the hybridization buffer ([Na+] for 1× Standard Sodium Citrate=0.165M). Typically, each such hybridizing polynucleotide has a length that is at least 25% (commonly at least 50%, 60%, or 70%, and most commonly at least 80%) of the length of a polynucleotide to which it hybridizes, and has at least 60% sequence identity (for example, at least 70%, 75%, 80%, 85%, 90%, 95%, 96%, 97%, 98%, 99% or 100%) with a polynucleotide to which it hybridizes.

As will be understood by the person skilled in the art, a linear DNA has two possible orientations: the 5'-to-3' direction and the 3'-to-5' direction. For example, if a reference sequence is positioned in the 5'-to-3' direction, and if a second sequence is positioned in the 5'-to-3' direction within the same polynucleotide molecule/strand, then the reference sequence and the second sequence are orientated in the same direction, or have the same orientation. Typically, a promoter sequence and a gene of interest under the regulation of the given promoter are positioned in the same orientation. However, with respect to the reference sequence positioned in the 5'-to-3' direction, if a second sequence is positioned in the 3'-to-5' direction within the same polynucleotide molecule/strand, then the reference sequence and the second sequence are orientated in anti-sense direction, or have anti-sense orientation. Two sequences having anti-sense orientations with respect to each other can be alternatively described as having the same orientation, if the reference sequence (5'-to-3' direction) and the reverse complementary sequence of the reference sequence (reference sequence positioned in the 5'-to-3') are positioned within the same polynucleotide molecule/strand. The sequences set forth herein are shown in the 5'-to-3' direction.

Recombinant constructs provided herein can be used to transform plants or plant cells in order to modulate protein expression and/or activity levels. A recombinant polynucleotide construct can comprise a polynucleotide encoding one or more polynucleotides as described herein, operably linked to a regulatory region suitable for expressing the polypeptide. Thus, a polynucleotide can comprise a coding sequence that encodes the polypeptide as described herein. Plants or plant cells in which protein expression and/or activity levels are modulated can include mutant, non-naturally occurring, transgenic, man-made or genetically engineered plants or plant cells. Suitably, the transgenic plant or plant cell comprises a genome that has been altered by the stable integration of recombinant DNA. Recombinant DNA includes DNA which has been genetically engineered and constructed outside of a cell and includes DNA containing naturally occurring DNA or cDNA or synthetic DNA. A transgenic plant can include a plant regenerated from an originally-transformed plant cell and progeny transgenic plants from later generations or crosses of a transformed plant. Suitably, the transgenic modification alters the expression or activity of the polynucleotide or the polypeptide described herein as compared to a control plant.

The polypeptide encoded by a recombinant polynucleotide can be a native polypeptide, or can be heterologous to the cell. In some cases, the recombinant construct contains a polynucleotide that modulates expression, operably linked to a regulatory region. Examples of suitable regulatory regions are described herein.

Vectors containing recombinant polynucleotide constructs such as those described herein are also provided. Suitable vector backbones include, for example, those routinely used in the art such as plasmids, viruses, artificial chromosomes, bacterial artificial chromosomes, yeast artificial chromosomes, or bacteriophage artificial chromosomes. Suitable expression vectors include, without limitation, plasmids and viral vectors derived from, for example, bacteriophage, baculoviruses, and retroviruses. Numerous vectors and expression systems are commercially available. The vectors can include, for example, origins of replication, scaffold attachment regions or markers. A marker gene can confer a selectable phenotype on a plant cell. For example, a marker can confer biocide resistance, such as resistance to an antibiotic (for example, kanamycin, G418, bleomycin, or hygromycin), or an herbicide (for example, glyphosate, chlorsulfuron or phosphinothricin). In addition, an expression vector can include a tag sequence designed to facilitate manipulation or detection (for example, purification or localization) of the expressed polypeptide. Tag sequences, such as luciferase, beta-glucuronidase, green fluorescent protein, glutathione S-transferase, polyhistidine, c-myc or hemagglutinin sequences typically are expressed as a fusion with the encoded polypeptide. Such tags can be inserted anywhere within the polypeptide, including at either the carboxyl or amino terminus.

A plant or plant cell can be transformed by having the recombinant polynucleotide integrated into its genome to become stably transformed. The plant or plant cell described herein can be stably transformed. Stably transformed cells typically retain the introduced polynucleotide with each cell division. A plant or plant cell can be transiently transformed such that the recombinant polynucleotide is not integrated into its genome. Transiently transformed cells typically lose all or some portion of the introduced recombinant polynucleotide with each cell division such that the introduced recombinant polynucleotide cannot be detected in daughter cells after a sufficient number of cell divisions. Suitably, NND3 is expressed in flowers (for example, immature flower, mature flower, immature capsule, dry capsule) and roots of a plant. Suitably, NND3 is expressed exclusively or specifically in flowers (for example, immature flower, mature flower, immature capsule, dry capsule) and roots of a plant. The use of genome editing is also contemplated.

A number of methods are available in the art for transforming a plant cell which are all encompassed herein, including biolistics, gene gun techniques, *Agrobacterium*-mediated transformation, viral vector-mediated transformation and electroporation. The *Agrobacterium* system for integration of foreign DNA into plant chromosomes has been extensively studied, modified, and exploited for plant genetic engineering. Naked recombinant DNA molecules comprising DNA sequences corresponding to the subject purified tobacco protein operably linked, in the sense or antisense orientation, to regulatory sequences are joined to appropriate T-DNA sequences by conventional methods. These are introduced into tobacco protoplasts by polyethylene glycol techniques or by electroporation techniques, both of which are standard.

Alternatively, such vectors comprising recombinant DNA molecules encoding the subject purified tobacco protein are introduced into live *Agrobacterium* cells, which then transfer the DNA into the tobacco plant cells. Transformation by naked DNA without accompanying T-DNA vector sequences can be accomplished via fusion of tobacco protoplasts with DNA-containing liposomes or via electroporation. Naked DNA unaccompanied by T-DNA vector sequences can also be used to transform tobacco cells via inert, high velocity microprojectiles.

If a cell or cultured tissue is used as the recipient tissue for transformation, plants can be regenerated from transformed cultures if desired, by techniques known to those skilled in the art.

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a polynucleotide can be modulated in a similar manner. Some suitable regulatory regions initiate transcription only, or predominantly, in certain cell types. Methods for identifying and characterizing regulatory regions in plant genomic DNA are known in the art.

Suitable promoters include tissue-specific promoters recognized by tissue-specific factors present in different tissues or cell types (for example, root-specific promoters, shoot-specific promoters, xylem-specific promoters), or present during different developmental stages, or present in response to different environmental conditions. Suitable promoters include constitutive promoters that can be activated in most cell types without requiring specific inducers. Examples of suitable promoters for controlling RNAi polypeptide production include the cauliflower mosaic virus 35S (CaMV/35S), SSU, OCS, lib4, usp, STLS1, B33, nos or ubiquitin- or phaseolin-promoters. Persons skilled in the art are capable of generating multiple variations of recombinant promoters.

Tissue-specific promoters are transcriptional control elements that are only active in particular cells or tissues at specific times during plant development, such as in vegetative tissues or reproductive tissues. Tissue-specific expression can be advantageous, for example, when the expression of polynucleotides in certain tissues is preferred. Examples of tissue-specific promoters under developmental control include promoters that can initiate transcription only (or primarily only) in certain tissues, such as vegetative tissues, for example, roots or leaves, or reproductive tissues, such as fruit, ovules, seeds, pollen, pistols, flowers, or any embryonic tissue. Reproductive tissue-specific promoters may be, for example, anther-specific, ovule-specific, embryo-specific, endosperm-specific, integument-specific, seed and seed coat-specific, pollen-specific, petal-specific, sepal-specific, or combinations thereof.

Suitable leaf-specific promoters include pyruvate, orthophosphate dikinase (PPDK) promoter from C4 plant (maize), cab-m1 Ca+2 promoter from maize, the *Arabidopsis thaliana* myb-related gene promoter (Atmyb5), the ribulose biphosphate carboxylase (RBCS) promoters (for example, the tomato RBCS 1, RBCS2 and RBCS3A genes expressed in leaves and light-grown seedlings, RBCS1 and RBCS2 expressed in developing tomato fruits or ribulose bisphosphate carboxylase promoter expressed almost exclusively in mesophyll cells in leaf blades and leaf sheaths at high levels).

Suitable senescence-specific promoters include a tomato promoter active during fruit ripening, senescence and abscission of leaves, a maize promoter of gene encoding a cysteine protease, the promoter of 82E4 and the promoter of SAG genes. Suitable anther-specific promoters can be used. Suitable root-preferred promoters known to persons skilled in the art may be selected. Suitable seed-preferred promoters include both seed-specific promoters (those promoters active during seed development such as promoters of seed storage proteins) and seed-germinating promoters (those promoters active during seed germination). Such seed-preferred promoters include, but are not limited to, Cim1 (cytokinin-induced message); cZ19B1 (maize 19 kDa zein); milps (myo-inositol-1-phosphate synthase); mZE40-2, also known as Zm-40; nuclc; and celA (cellulose synthase). Gama-zein is an endosperm-specific promoter. Glob-1 is an embryo-specific promoter. For dicots, seed-specific promoters include, but are not limited to, bean beta-phaseolin, napin, β-conglycinin, soybean lectin, cruciferin, and the like. For monocots, seed-specific promoters include, but are not limited to, a maize 15 kDa zein promoter, a 22 kDa zein promoter, a 27 kDa zein promoter, a g-zein promoter, a 27 kDa gamma-zein promoter (such as gzw64A promoter, see Genbank Accession number S78780), a waxy promoter, a shrunken 1 promoter, a shrunken 2 promoter, a globulin 1 promoter (see Genbank Accession number L22344), an ltp2 promoter, cim1 promoter, maize end1 and end2 promoters, nuc1 promoter, Zm40 promoter, eep1 and eep2; lec1, thioredoxin H promoter; mlip15 promoter, PCNA2 promoter; and the shrunken-2 promoter.

Examples of inducible promoters include promoters responsive to pathogen attack, anaerobic conditions, elevated temperature, light, drought, cold temperature, or high salt concentration. Pathogen-inducible promoters include those from pathogenesis-related proteins (PR proteins), which are induced following infection by a pathogen (for example, PR proteins, SAR proteins, beta-1,3-glucanase, chitinase).

In addition to plant promoters, other suitable promoters may be derived from bacterial origin for example, the octopine synthase promoter, the nopaline synthase promoter and other promoters derived from Ti plasmids, or may be derived from viral promoters (for example, 35S and 19S RNA promoters of cauliflower mosaic virus (CaMV), constitutive promoters of tobacco mosaic virus, cauliflower mosaic virus (CaMV) 19S and 35S promoters, or figwort mosaic virus 35S promoter).

In another aspect, there is provided an isolated polypeptide comprising, consisting or consisting essentially of a polypeptide sequence having at least 95% sequence identity to any of the polypeptide sequences described herein, including any of the polypeptides shown in the sequence listing. Suitably, the isolated polypeptide comprises, consists or consists essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity thereto. In one embodiment, there is provided a polypeptide encoded by SEQ ID NO: 3.

In another embodiment, there is provided an isolated polypeptide comprising, consisting or consisting essentially of a sequence having at least 95% 96%, 97%, 98%, 99%, 99.1%, 99.2%, 99.3%, 99.4%, 99.5%, 99.6%, 99.7%, 99.8%, 99.9% or 100% sequence identity to SEQ ID NO: 3.

In another embodiment, there is provided a polypeptide variant comprising, consisting or consisting essentially of an amino acid sequence encoded by a polynucleotide variant with at least about 95% 96%, 97%, 98%, 99% 99.1%, 99.2%, 99.3%, 99.4%, 99.5%, 99.6%, 99.7%, 99.8% or 99.9% sequence identity to SEQ ID NO: 3.

In another embodiment, there is provided fragments of the polypeptide of SEQ ID NO: 3 or fragments of SEQ ID NO: 3 that have at least about 95% 96%, 97%, 98%, 99%, 99.1%, 99.2%, 99.3%, 99.4%, 99.5%, 99.6%, 99.7%, 99.8%, 99.9% or 100% sequence identity to the corresponding fragments of SEQ ID NO: 3.

Fragments of SEQ ID NO:3 are, for example, at least 15 amino acids in length, comprising 15 contiguous amino acids of SEQ ID NO:3. Moreover, the fragments can be 20, 25, 30, 35, 40 or more amino acids in length, up to the entire 517 amino acid length, and comprise the corresponding number of contiguous amino acids of SEQ ID NO:3.

Preferred fragments include fragments which encompass amino acids 1-15, 330-345, 420-450 and 480-510 of SEQ ID NO:3.

The polypeptide can include sequences comprising a sufficient or substantial degree of identity or similarity to SEQ ID NO: 3 to function as nicotine N-demethylase. Fragments of the polypeptide(s) typically retain some or all of the activity of the full length sequence.

As discussed herein, the polypeptides also include mutants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally provided that they still have some or all of their function or activity as a nicotine N-demethylase. Suitably, the function or activity as a nicotine N-demethylase is modulated, reduced or inhibited. Suitably, the function or activity as a nicotine N-demethylase is inhibited such that the nicotine N-demethylase activity is not detectable.

A polypeptide encoded by SEQ ID NO: 3 that has 100% sequence identity thereto or a polypeptide comprising, consisting or consisting essentially of the sequence set forth in SEQ ID NO: 3 that has 100% sequence identity thereto is also disclosed.

Polypeptides include variants produced by introducing any type of alterations (for example, insertions, deletions, or substitutions of amino acids; changes in glycosylation states; changes that affect refolding or isomerizations, three-dimensional structures, or self-association states), which can be deliberately engineered or isolated naturally. The variant may have alterations which produce a silent change and result in a functionally equivalent protein. Deliberate amino acid substitutions may be made on the basis of similarity in polarity, charge, solubility, hydrophobicity, hydrophilicity and the amphipathic nature of the residues as long as the secondary binding activity of the substance is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine. Conservative substitutions may be made, for example according to the Table below. Amino acids in the same block in the second column and preferably in the same line in the third column may be substituted for each other:

| ALIPHATIC | Non-polar | Gly Ala Pro |
| | | Ile Leu Val |
| | Polar-uncharged | Cys Ser Thr Met |
| | | Asn Gly |
| | Polar-charged | Asp Glu |
| | | Lys Arg |
| AROMATIC | | His Phe TrpTyr |

The polypeptide may be a mature protein or an immature protein or a protein derived from an immature protein. Polypeptides may be in linear form or cyclized using known methods. Polypeptides typically comprise at least 10, at least 20, at least 30, or at least 40 contiguous amino acids.

A tobacco plant or plant cell comprising a mutation in a gene encoding NND3 as described herein is disclosed, wherein said mutation results in reduced expression or reduced function of said NND3. The expression or function of the NND3 mutant(s) may be inhibited. The expression or function of the NND3 mutant(s) may not detectable. Aside from one or more mutations in NND3, the mutant plants or plant cells can have one or more further mutations in one or more other genes or polypeptides. In certain embodiments, aside from the one or more mutations in NND3, the mutants can have one or more further mutations in one or more other genes or polypeptides—such as one or more other nicotine demethylase genes or polypeptides. Suitably, NND3 is expressed in flowers (for example, immature flower, mature flower, immature capsule, dry capsule) and roots of the mutant plant. Suitably, NND3 is expressed exclusively or specifically in flowers (for example, immature flower, mature flower, immature capsule, dry capsule) and roots of the mutant plant.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase. Suitably, said CYP82E4 nicotine demethylase is selected from the sequence set forth in SEQ ID NOs: 6 to 16 or a combination of two or more thereof. Suitably, said mutation results in a modification of said CYP82E4 nicotine demethylase occurring at a position selected from the group consisting of amino acid residues 38, 171, 201, 169, 459, 427, 329, 364, 376, 382, and 458 of SEQ ID NO: 5 or a combination of two or more thereof. Suitably, said mutation is selected from the group consisting of: a) a leucine substitution for the proline residue at position 38 of SEQ ID NO: 5; b) an asparagine substitution for the aspartic acid residue at position 171 of SEQ ID NO: 5; c) a lysine substitution for the glutamic acid residue at position 201 of SEQ ID NO: 5; d) a glutamine substitution for the arginine residue at position 169 of SEQ ID NO: 5; e) an arginine substitution for the glycine residue at position 459 of SEQ ID NO: 5; f) an isoleucine substitution for the threonine residue at position 427 of SEQ ID NO: 5; g) a methionine substitution for the valine residue at position 376 of SEQ ID NO: 5; h) an stop codon for the tryptophan residue at position 329 of SEQ ID NO: 5; i) an asparagine substitution for the lysine residue at position 364 of SEQ ID NO: 5; j) a serine substitution for the proline residue at position 382 of SEQ ID NO: 5; k) a serine substitution for the proline residue at position 458 of SEQ ID NO: 5; or l) a combination of two or more thereof.

Suitably, the NND3 mutant tobacco plant or plant cell further comprises a mutation in a gene encoding a CYP82E5 nicotine demethylase, wherein said mutation results in reduced expression or function of said CYP82E5 nicotine demethylase. Suitably, said CYP82E5 nicotine demethylase is selected from the sequence set forth in SEQ ID NOs: 18 to 25 or a combination of two or more thereof. Suitably, said mutation results in a modification of said CYP82E5 nicotine demethylase occurring at a position selected from the group consisting of amino acid residues 72, 143, 174, 224, 235, 410, 422 or 449 of SEQ ID NO: 17 or a combination of two or more thereof. Suitably, said mutation is selected from the group consisting of: a) a leucine substitution for the proline residue at position 72 of SEQ ID NO: 17; b) a phenylalanine substitution for the leucine residue at position 143 of SEQ ID NO: 17; c) a leucine substitution for the serine residue at position 174 of SEQ ID NO: 17; d) an isoleucine substitution for the methionine residue at position 224 of SEQ ID NO: 17; e) a serine substitution for the proline residue at position 235 of SEQ ID NO: 17; f) an isoleucine substitution for the threonine residue at position 427 of SEQ ID NO: 17; g) a methionine substitution for the valine residue at position 376 of SEQ ID NO: 17; h) an stop codon for the tryptophan residue at position 329 of SEQ ID NO: 17; i) a valine substitution for the alanine residue at position 410 of SEQ ID NO: 17; j) a stop codon for the tryptophan residue at position 422 of SEQ ID NO: 17; k) a leucine substitution for the proline residue at position 449 of SEQ ID NO: 17; or l) a combination of two or more thereof.

Suitably, the NND3 mutant tobacco plant or plant cell further comprises a mutation in a gene encoding a CYP82E10 nicotine demethylase, wherein said mutation results in reduced expression or function of said CYP82E10 nicotine demethylase. Suitably, said CYP82E4 nicotine demethylase is selected from the sequence set forth in SEQ ID NOs: 27 to 35 or a combination of two or more thereof. Suitably, said mutation results in a modification of said CYP82E10 nicotine demethylase occurring at a position selected from the group consisting of amino acid residues 148, 172, 344, 410, 417, 419, 79, 107 or 382 of SEQ ID NO: 26 or a combination of two or more thereof. Suitably, said mutation is selected from the group consisting of: a) a phenylanaline substitution for the leucine residue at position 148 of SEQ ID NO: 26; b) an arginine substitution for the glycine residue at position 172 of SEQ ID NO: 26; c) a threonine substitution for the alanine residue at position 344 of SEQ ID NO: 26; d) a threonine substitution for the alanine residue at position 410 of SEQ ID NO: 26; e) a histidine substitution for the arginine residue at position 417 of SEQ ID NO: 26; f) a serine substitution for the proline residue at position 419 of SEQ ID NO: 26; g) a serine substitution for the glycine residue at position 79 of SEQ ID NO: 26; h) a serine codon for the proline residue at position 107 of SEQ ID NO: 26; i) a serine substitution for the proline residue at position 382 of SEQ ID NO: 26; or j) a combination of two or more thereof.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase. Suitably, said CYP82E4 nicotine demethylase is selected from the sequence set forth in SEQ ID NOs: 13 to 16 or a combination of two or more thereof. Suitably, said mutation results in a modification of said CYP82E4 nicotine demethylase occurring at a position selected from the group consisting of amino acid residues 329, 365, 382 or 458 of SEQ ID NO: 5 or a combination of two or more thereof. Suitably, said mutation is selected from the group consisting of: a) a stop codon substitution for the tryptophan residue at position 329; b) an asparagine substitution for the lysine residue at position 364; c) a methionine substitution for the valine residue at position 376; d) a serine substitution for the proline residue at position 382; e) a serine substitution for the proline residue at position 458; and f) any combination thereof. Suitably, the tobacco plant or plant cell further comprises a mutation in a gene encoding a CYP82E4 nicotine demethylase, wherein said mutation results in reduced expression or function of said CYP82E4 nicotine demethylase. Suitably, said CYP82E4 nicotine demethylase comprises the sequence set forth in SEQ ID NO: 13 (W329Stop). Suitably, said mutation results in a modification of said CYP82E4 nicotine demethylase occurring at amino acid residue 329 of SEQ ID NO: 5. Suitably, said mutation is a stop codon substitution for the tryptophan residue at position 329.

Suitably, the NND3 mutant tobacco plant or plant cell further comprises a mutation in a gene encoding a CYP82E5 nicotine demethylase, wherein said mutation results in reduced expression or function of said CYP82E5 nicotine demethylase. Suitably, said CYP82E5 nicotine demethylase comprises the sequence set forth in SEQ ID NOs: 24 or 25 or a combination of two or more thereof. Suitably, said mutation results in a modification of said CYP82E5 nicotine demethylase occurring at a position selected from the group consisting of amino acid residues 422 and 449, wherein said numbering is according to SEQ ID NO: 12.

Suitably, said mutation is selected from the group consisting of: a) a stop codon substituted for the tryptophan residue at position 422; b) a leucine substituted for the proline residue at position 449; and c) any combination thereof.

Suitably, the NND3 mutant tobacco plant or plant cell further comprises a mutation in a gene encoding a CYP82E5 nicotine demethylase, wherein said mutation results in reduced expression or function of said CYP82E5 nicotine demethylase. Suitably, said CYP82E5 nicotine demethylase comprises the sequence set forth in SEQ ID NO: 24 (W422Stop). Suitably, said mutation results in a modification of said CYP82E5 nicotine demethylase occurring at amino acid residue 422, wherein said numbering is according to SEQ ID NO: 17. Suitably, said mutation is a stop codon substituted for the tryptophan residue at position 422. Suitably, the NND3 mutant tobacco plant or plant cell further comprises a mutation in a gene encoding a CYP82E10 nicotine demethylase, wherein said mutation results in reduced expression or function of said CYP82E10 nicotine demethylase. Suitably, said CYP82E10 nicotine demethylase is selected from the group consisting of SEQ ID NOs: 32-35 or a combination of two or more thereof. Suitably, said mutation results in a modification of said CYP82E10 nicotine demethylase occurring at a position selected from the group consisting of amino acid residues 79, 107, 382, 419 and any combination thereof, wherein said numbering is according to SEQ ID NO:26. Suitably, said mutation is selected from the group consisting of: a) a serine substitution for the glycine residue at position 79; b) a serine substitution for the proline residue at position 107; c) a serine substitution for the proline residue at position 382; d) a serine substitution for the proline residue at position 419; and e) any combination thereof.

Suitably, the NND3 mutant tobacco plant or plant cell further comprises a mutation in a gene encoding a CYP82E10 nicotine demethylase, wherein said mutation results in reduced expression or function of said CYP82E10 nicotine demethylase. Suitably, said CYP82E10 nicotine demethylase is selected from the group consisting of SEQ ID NOs: 32-34 or a combination of two or more thereof. Suitably, said mutation results in a modification of said CYP82E10 nicotine demethylase occurring at a position selected from the group consisting of amino acid residues 79, 107, 382 and any combination thereof, wherein said numbering is according to SEQ ID NO:26. Suitably, said mutation is selected from the group consisting of: a) a serine substitution for the glycine residue at position 79; b) a serine substitution for the proline residue at position 107; c) a serine substitution for the proline residue at position 382; and d) any combination thereof.

Suitably the NND3 mutant tobacco plant or plant cell further comprises one or more mutations as disclosed above in a CYP82E4 nicotine demethylase gene and in a CYP82E5 nicotine demethylase gene. Suitably said tobacco plant or plant cell further comprises one or more mutations as disclosed above in a CYP82E4 nicotine demethylase gene and a CYP82E10 nicotine demethylase gene. Suitably said tobacco plant or plant cell further comprises one or more mutations as disclosed above in a CYP82E5 nicotine demethylase gene and a CYP82E10 nicotine demethylase gene. Suitably said tobacco plant or plant cell further comprises one or more mutations as disclosed above in a CYP82E4 nicotine demethylase gene and a CYP82E5 nicotine demethylase gene and CYP82E10 nicotine demethylase gene.

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 33 (G79S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 34 (P107S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 35 (P382S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 32 (P419S).

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 419 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 79 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 107 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 382 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the glycine residue at position 79 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the proline residue at position 107 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the proline residue at position 382 of SEQ ID NO:26.

Suitably, the NND3 mutant tobacco plant or plant cell further comprises a homozygous mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a homozygous mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a homozygous mutation in a gene encoding a CYP82E10 nicotine demethylase, wherein said mutation results in reduced expression or function of said CYP82E10 nicotine demethylase and occurs at amino acid residue 419 of SEQ ID NO:26.

Suitably, the NND3 mutant tobacco plant or plant cell further comprises a homozygous mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a homozygous mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a homozygous mutation in a gene encoding a CYP82E10 nicotine demethylase, wherein said mutation results in reduced expression or function of said CYP82E10 nicotine demethylase and is a serine substitution for the proline residue at position 382 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase. Suitably, said CYP82E4 nicotine demethylase is selected from the sequence set forth in SEQ ID NOs: 12 to 16 or a combination of two or more thereof. Suitably, said mutation results in a modification of said CYP82E4 nicotine demethylase occurring at a position selected from the group consisting of amino acid residues 329, 364, 376, 382, and 458 of SEQ ID NO: 5. Suitably, said mutation is selected from the group consisting of: a) a stop codon substitution for the tryptophan residue at position 329; b) an asparagine substitution for the lysine residue at position 364; c) a methionine substitution for the valine residue at position 376; d) a serine substitution for the proline residue at position 3 82; e) a serine substitution for the proline residue at position 458; and f) any combination thereof. Suitably, the NND3 mutant tobacco plant or plant cell further comprises a mutation in a gene encoding a CYP82E4 nicotine demethylase, wherein said mutation results in reduced expression or function of said CYP82E4 nicotine demethylase. Suitably, said CYP82E4 nicotine demethylase comprises the sequence set forth in SEQ ID NO: 13 (W329Stop). Suitably, said mutation results in a modification of said CYP82E4 nicotine demethylase occurring at amino acid residue 329 of SEQ ID NO: 5. Suitably, said mutation is a stop codon substitution for the tryptophan residue at position 329.

Suitably, the NND3 mutant tobacco plant or plant cell further comprises a mutation in a gene encoding a CYP82E5 nicotine demethylase, wherein said mutation results in reduced expression or function of said CYP82E5 nicotine demethylase. Suitably, said CYP82E5 nicotine demethylase comprises the sequence set forth in SEQ ID NOs: 24 or 25 or a combination of two or more thereof. Suitably, said mutation results in a modification of said CYP82E5 nicotine demethylase occurring at a position selected from the group consisting of amino acid residues 422 and 449, wherein said numbering is according to SEQ ID NO: 12. Suitably, said mutation is selected from the group consisting of: a) a stop codon substituted for the tryptophan residue at position 422; b) a leucine substituted for the proline residue at position 449; and c) any combination thereof.

Suitably, the NND3 mutant tobacco plant or plant cell further comprises a mutation in a gene encoding a CYP82E5 nicotine demethylase, wherein said mutation results in reduced expression or function of said CYP82E5 nicotine demethylase. Suitably, said CYP82E5 nicotine demethylase comprises the sequence set forth in SEQ ID NO: 24 (W422Stop). Suitably, said mutation results in a modification of said CYP82E5 nicotine demethylase occurring at amino acid residue 422, wherein said numbering is according to SEQ ID NO: 17. Suitably, said mutation is a stop codon substituted for the tryptophan residue at position 422.

Suitably, the NND3 mutant tobacco plant or plant cell comprises a further mutation in a gene encoding a CYP82E10 nicotine demethylase, wherein said mutation results in reduced expression or function of said CYP82E10 nicotine demethylase. Suitably, said CYP82E10 nicotine demethylase is selected from the group consisting of SEQ ID NOs: 32-35 or a combination of two or more thereof. Suitably, said mutation results in a modification of said CYP82E10 nicotine demethylase occurring at a position selected from the group consisting of amino acid residues 79, 107, 382, 419 and any combination thereof, wherein said numbering is according to SEQ ID NO:26. Suitably, said mutation is selected from the group consisting of: a) a serine substitution for the glycine residue at position 79; b) a serine substitution for the proline residue at position 107; c) a serine substitution for the proline residue at position 382; d)

a serine substitution for the proline residue at position 419; and e) any combination thereof.

Suitably, the NND3 mutant tobacco plant or plant cell comprises a further mutation in a gene encoding a CYP82E10 nicotine demethylase, wherein said mutation results in reduced expression or function of said CYP82E10 nicotine demethylase. Suitably, said CYP82E10 nicotine demethylase is selected from the group consisting of SEQ ID NOs: 32-34 or a combination of two or more thereof. Suitably, said mutation results in a modification of said CYP82E10 nicotine demethylase occurring at a position selected from the group consisting of amino acid residues 79, 107, 382 and any combination thereof, wherein said numbering is according to SEQ ID NO:26. Suitably, said mutation is selected from the group consisting of: a) a serine substitution for the glycine residue at position 79; b) a serine substitution for the proline residue at position 107; c) a serine substitution for the proline residue at position 382; and d) any combination thereof.

Suitably, the NND3 mutant tobacco plant or plant cell further comprises one or more mutations as disclosed above in a CYP82E4 nicotine demethylase gene and a CYP82E5 nicotine demethylase gene. Suitably said tobacco plant or plant cell further comprises one or more mutations as disclosed above in a CYP82E4 nicotine demethylase gene and a CYP82E10 nicotine demethylase gene. Suitably said tobacco plant or plant cell further comprises one or more mutations as disclosed above in a CYP82E5 nicotine demethylase gene and a CYP82E10 nicotine demethylase gene. Suitably said tobacco plant or plant cell further comprises one or more mutations as disclosed above in a CYP82E4 nicotine demethylase gene and a CYP82E5 nicotine demethylase gene and CYP82E10 nicotine demethylase gene.

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 33 (G79S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 34 (P107S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 35 (P382S).

Suitably, said CYP82E4 nicotine demethylase comprise the sequence set forth in SEQ ID NO: 13 (W329Stop), said CYP82E5 nicotine demethylase comprise the sequence set forth in SEQ ID NO: 24 (W422Stop), and said CYP82E10 nicotine demethylase comprise the sequence set forth in SEQ ID NO: 32 (P419S).

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 419 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 79 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 107 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a mutation in a gene encoding a CYP82E10 nicotine demethylase, wherein said mutation results in reduced expression or function of said CYP82E10 nicotine demethylase and occurs at amino acid residue 382 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the glycine residue at position 79 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the proline residue at position 107 of SEQ ID NO:26.

Suitably, the NND3 mutant tobacco plant or plant cell further comprises a mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a mutation in a gene encoding a CYP82E10 nicotine demethylase, wherein said mutation results in reduced expression or function of said CYP82E10 nicotine demethylase and is a serine substitution for the proline residue at position 382 of SEQ ID NO:26.

Suitably, the NND3 mutant tobacco plant or plant cell further comprises a homozygous mutation in a gene encoding a CYP82E4 nicotine demethylase, wherein said mutation results in reduced expression or function of said CYP82E4 nicotine demethylase and occurs at amino acid residue 329 of SEQ ID NO:25, and comprises a homozygous mutation in a gene encoding a CYP82E5 nicotine demethylase, wherein said mutation results in reduced expression or function of said CYP82E5 nicotine demethylase and occurs at amino acid residue 422 of SEQ ID NO:17, and comprises a homozygous mutation in a gene encoding a CYP82E10 nicotine demethylase, wherein said mutation results in reduced expression or function of said CYP82E10 nicotine demethylase and occurs at amino acid residue 419 of SEQ ID NO:26.

Suitably, the NND3 mutant tobacco plant or plant cell further comprises a homozygous mutation in a gene encoding a CYP82E4 nicotine demethylase, wherein said mutation results in reduced expression or function of said CYP82E4 nicotine demethylase and is a stop codon substitution for the tryptophan residue at position 329 of SEQ ID NO:5, and comprises a homozygous mutation in a gene encoding a CYP82E5 nicotine demethylase, wherein said mutation results in reduced expression or function of said CYP82E5 nicotine demethylase and is a stop codon substituted for the tryptophan residue at position 422 of SEQ ID NO: 17, and comprises a homozygous mutation in a gene encoding a CYP82E10 nicotine demethylase, wherein said mutation results in reduced expression or function of said CYP82E10 nicotine demethylase and is a serine substitution for the proline residue at position 382 of SEQ ID NO:26.

Suitably, the plant, the plant cell, the plant material or the (cured) tobacco product and the like that is obtained or obtainable according to the present disclosure has less than about 1.0%, less than about 0.9%, less than about 0.8%, less than about 0.7%, less than about 0.6%, less than about 0.5%, less than about 0.4%, less than about 0.3%, less than about 0.2% or less than about 0.1% conversion of nicotine to nornicotine. The % conversion is calculated using the equation [% nornicotine/(% nornicotine+% nicotine)]×100.

Suitably, the plant, the plant cell, the plant material or the cured) tobacco product and the like that is obtained or obtainable according to the present disclosure has less than about 0.04%, less than about 0.03%, less than about 0.02% or less than about 0.01% nornicotine, calculated on a dry weight basis.

Said NND3 mutant tobacco plant or plant cell can be heterozygous or homozygous for the mutation(s). Said NND3 mutant tobacco plant or plant cell can be heterozygous for at least one mutation and homozygous for at least one different mutation.

There is also provided a method for reducing the level of nornicotine, or reducing the rate of conversion of nicotine to nornicotine or reducing the level of at least NNN in a (cured) tobacco plant or in (cured) tobacco plant material said method comprising introducing into the genome of said plant one or more mutations that reduce expression of at least one nicotine demethylase gene, wherein said at least one nicotine demethylase gene encodes NND3. Suitably, in addition to the mutation(s) in NND3, one or more mutations can also be introduced into at least one allele of at least one, two or three or more further nicotine demethylase genes, wherein said genes are selected from the group consisting of CYP82E4, CYP82E5 and CYP82E10 or a combination of two or more thereof as discussed above.

There is also provided a method for identifying a tobacco plant with low levels of nornicotine or low levels of at least NNN, said method comprising screening a nucleic acid sample from a tobacco plant of interest for the presence of one or more mutations in SEQ ID NO:1 or 2, and optionally correlating the identified mutation(s) with mutation(s) that are known to modulate levels of nornicotine or at least NNN. Suitably, said method further comprises screening said nucleic acid sample, or another nucleic acid sample from said tobacco plant of interest, for the presence of a mutation in SEQ ID NO: 5, the presence of a mutation in SEQ ID NO:12, or the presence of a mutation in SEQ ID NO: 19, and optionally correlating the identified mutation(s) with mutation(s) that are known to modulate levels of nornicotine or at least NNN.

There is also disclosed a tobacco plant or plant cell that is heterozygous or homozygous for mutations in a gene encoding NND3, a gene encoding a CYP82E10 nicotine demethylase, a gene encoding a CYP82E4 nicotine demethylase, and a gene encoding a CYP82E5 nicotine demethylase, wherein said mutation results in reduced expression or function of NND3, CYP82E10, CYP82E4, and CYP82E5 nicotine demethylases.

There is also described a tobacco plant or plant cell comprising, consisting or consisting essentially of one or more heterozygous or homozygous mutations in a NND3 gene or polypeptide, as described herein, that reduce nicotine demethylase activity in flowers (for example, immature flower, mature flower, immature capsule, dry capsule) and roots, one or more heterozygous or homozygous mutations in a CYP82E10 gene or polypeptide that reduces nicotine demethylase activity in roots, one or more heterozygous or homozygous mutations in a CYP82E4 gene or polypeptide that reduces nicotine demethylase activity in senescent leaves, and one or more mutations in a CYP83E5 gene or polypeptide that reduces nicotine demethylase activity in green leaves.

A number of approaches can be used to combine mutations in one plant including sexual crossing. A plant having one or more favourable heterozygous or homozygous mutations in NND3 that reduces nicotine demethylase can be crossed with a plant having one or more favourable heterozygous or homozygous mutations in one or more of CYP82E4, CYP82E5 and CYP82E10 that reduce nicotine demethylase activity. In one embodiment, crosses are made in order to introduce one or more favourable heterozygous or homozygous mutations within NND3 and CYP82E10 or NND3 and CYP82E4 or NND3 and CYP82E5 within the same plant. In this manner, a plant having one or more favourable heterozygous or homozygous mutations in NND3 that reduces the nicotine demethylases activity in flowers (for example, immature flower, mature flower, immature capsule, dry capsule) and roots, is crossed with a plant having one or more favourable heterozygous or homozygous mutations in CYP82E10 that reduces nicotine demethylases activity in roots, or is crossed with a plant having one or more favourable heterozygous or homozygous mutations in CYP82E4 that reduces nicotine demethylase activity in senescent leaves, or is crossed with a plant having one or more favourable heterozygous or homozygous mutations in CYP83E5 gene that reduces nicotine demethylase activity in green leaves. In another embodiment, crosses are made in order to introduce one or more favourable heterozygous or homozygous mutations within NND3, CYP82E10 and CYP82E4 within the same plant. In this manner, a plant having one or more favourable heterozygous or homozygous mutations in NND3 that reduces the nicotine demethylases activity in flowers (for example, immature flower, mature flower, immature capsule, dry capsule) and roots, is crossed with a plant having one or more favourable heterozygous or homozygous mutations in CYP82E10 that reduces nicotine demethylases activity in roots, and is crossed with a plant having one or more favourable heterozygous or homozygous mutations in CYP82E4 that reduces nicotine demethylase activity in senescent leaves. In another embodiment, crosses are made in order to introduce one or more favourable heterozygous or homozygous mutations within NND3, CYP82E10 and CYP82E5 within the same plant. In this manner, a plant having one or more favourable heterozygous or homozygous mutations in NND3 that reduces the nicotine demethylases activity in flowers (for example, immature flower, mature flower, immature capsule, dry capsule) and roots, is crossed with a plant having one or more favourable heterozygous or homozygous mutations in CYP82E10 that reduces nicotine demethylases activity in roots, and is crossed with a plant having one or more favourable heterozygous or homozygous mutations in CYP83E5 that reduces nicotine demethylase activity in green leaves. In another embodiment, crosses are made in order to introduce one or more favourable heterozygous or homozygous mutations within NND3, CYP82E4 and CYP82E5 within the same plant. In this manner, a plant having one or more favourable heterozygous or homozygous mutations in NND3 that reduces the nicotine demethylases activity in flowers (for example, immature flower, mature flower, immature capsule, dry capsule) and roots, is crossed with a plant having one or more favourable heterozygous or homozygous mutations in CYP82E4 that reduces nicotine demethylase activity in senescent leaves, and is crossed with a plant having one or more favourable heterozygous or homozygous mutations in CYP83E5 that reduces nicotine demethylase activity in green leaves. In another embodiment, crosses are made in order to introduce one or more favourable heterozygous or homozygous mutations within NND3, CYP82E4, CYP82E5 and CYP82E10 within the same plant. In this manner, a plant having one or more favourable heterozygous or homozygous mutations in NND3 that reduces the nicotine demethylases activity in flowers (for example, immature flower, mature flower, immature capsule, dry capsule) and roots, is crossed with a plant having one or more favourable heterozygous or homozygous mutations in CYP82E10 that reduces nicotine demethylases activity in roots, one or more favourable heterozygous or homozygous mutations in CYP82E4 that reduces nicotine demethylase activity in senescent leaves, and one or more favourable heterozygous or homozygous mutations in CYP83E5 that reduces nicotine demethylase activity in green leaves. By introducing one or more favourable mutation(s) into the nicotine demethylases gene(s)—such as the favourable mutations that are described herein—it is possible to produce a plant having reduced or negligible or no detectable nicotine to nornicotine conversion or metabolite thereof or a plant having reduced or negligible or no detectable NNN.

The activity of one or more nicotine demethylase polypeptides in converting nicotine to nornicotine or a metabolite thereof in a tobacco plant is reduced or inhibited according to the present disclosure if the conversion activity is statistically lower than conversion activity of the same nicotine demethylase polypeptide(s) in a tobacco plant that has not been modified to inhibit the conversion activity of that nicotine demethylase polypeptide and which has been cultured and harvested using the same protocols. The activity of a nicotine demethylase polypeptide in converting nicotine to nornicotine in a tobacco plant is considered to be eliminated when it is not detectable by the assay methods described herein. Methods of determining the activity of a nicotine demethylase polypeptide in converting nicotine to nornicotine in a tobacco plant are described herein.

In some embodiments, the favourable mutation(s) is introduced into a tobacco plant or plant cell using a mutagenesis approach, and the introduced mutation is identified or selected using methods known to those of skill in the art—such as Southern blot analysis, DNA sequencing, PCR analysis, or phenotypic analysis. Mutations that impact gene expression or that interfere with the function of the encoded protein can be determined using methods that are well known in the art. Insertional mutations in gene exons usually result in null-mutants. Mutations in conserved residues can be particularly effective in inhibiting the metabolic function of the encoded protein.

Methods for obtaining mutant polynucleotides and polypeptides are also disclosed. Any plant of interest, including a plant cell or plant material can be genetically modified by various methods known to induce mutagenesis, including site-directed mutagenesis, oligonucleotide-directed mutagenesis, chemically-induced mutagenesis, irradiation-induced mutagenesis, mutagenesis utilizing modified bases, mutagenesis utilizing gapped duplex DNA, double-strand break mutagenesis, mutagenesis utilizing repair-deficient host strains, mutagenesis by total gene synthesis, DNA shuffling and other equivalent methods.

Fragments of NND3 polynucleotides and polypeptides encoded thereby are also disclosed.

Fragments of a polynucleotide may encode protein fragments that retain the biological activity of the native protein and hence are involved in the metabolic conversion of nicotine to nornicotine. Alternatively, fragments of a polynucleotide that are useful as hybridization probes or PCR primers generally do not encode fragment proteins retaining biological activity. Furthermore, fragments of the disclosed nucleotide sequences include those that can be assembled within recombinant constructs as discussed herein. Fragments of a polynucleotide sequence may range from at least about 25 nucleotides, about 50 nucleotides, about 75 nucleotides, about 100 nucleotides about 150 nucleotides, about 200 nucleotides, about 250 nucleotides, about 300 nucleotides, about 400 nucleotides, about 500 nucleotides, about 600 nucleotides, about 700 nucleotides, about 800 nucleotides, about 900 nucleotides, about 1000 nucleotides, about 1100 nucleotides, about 1200 nucleotides, about 1300 nucleotides or about 1400 nucleotides and up to the full-length polynucleotide encoding the polypeptides described herein. Fragments of a polypeptide sequence may range from at least about 25 amino acids, about 50 amino acids, about 75 amino acids, about 100 amino acids about 150 amino acids, about 200 amino acids, about 250 amino acids, about 300 amino acids, about 400 amino acids, about 500 amino acids, and up to the full-length polypeptide described herein.

Mutant polypeptide variants can be used to create mutant, non-naturally occurring or transgenic plants (for example, mutant, non-naturally occurring, transgenic, man-made or genetically engineered plants) or plant cells comprising one or more mutant polypeptide variants. Suitably, mutant polypeptide variants retain the activity of the unmutated polypeptide. The activity of the mutant polypeptide variant may be higher, lower or about the same as the unmutated polypeptide.

Mutations in the nucleotide sequences and polypeptides described herein can include man-made mutations or synthetic mutations or genetically engineered mutations. Mutations in the nucleotide sequences and polypeptides described herein can be mutations that are obtained or obtainable via a process which includes an in vitro or an in vivo manipulation step. Mutations in the nucleotide sequences and polypeptides described herein can be mutations that are obtained or obtainable via a process which includes intervention by man. By way of example, the process may include mutagenesis using exogenously added chemicals—such as mutagenic, teratogenic, or carcinogenic organic compounds, for example ethyl methanesulfonate (EMS), that produce random mutations in genetic material. By way of further example, the process may include one or more genetic engineering steps—such as one or more of the genetic engineering steps that are described herein or combinations thereof. By way of further example, the process may include one or more plant crossing steps.

A polypeptide may be prepared by culturing transformed or recombinant host cells under culture conditions suitable to express a polypeptide. The resulting expressed polypeptide may then be purified from such culture using known purification processes. The purification of the polypeptide may include an affinity column containing agents which will bind to the polypeptide; one or more column steps over such affinity resins; one or more steps involving hydrophobic interaction chromatography; or immunoaffinity chromatography. Alternatively, the polypeptide may also be expressed in a form that will facilitate purification. For example, it may be expressed as a fusion polypeptide, such as those of maltose binding polypeptide, glutathione-5-transferase, his-tag or thioredoxin. Kits for expression and purification of fusion polypeptides are commercially available. The polypeptide may be tagged with an epitope and subsequently purified by using a specific antibody directed to such epitope. One or more liquid chromatography steps—such as reverse-phase high performance liquid chromatography can be employed to further purify the polypeptide. Some or all of the foregoing purification steps, in various combinations, can be employed to provide a substantially homogeneous recombinant polypeptide. The polypeptide thus purified may be substantially free of other polypeptides and is defined herein as a "substantially purified polypeptide"; such purified polypeptides include polypeptides, fragments, variants, and the like. Expression, isolation, and purification of the polypeptides and fragments can be accomplished by any suitable technique, including but not limited to the methods described herein.

It is also possible to utilise an affinity column such as a monoclonal antibody generated against polypeptides, to affinity-purify expressed polypeptides. These polypeptides can be removed from an affinity column using conventional techniques, for example, in a high salt elution buffer and then dialyzed into a lower salt buffer for use or by changing pH or other components depending on the affinity matrix utilized, or be competitively removed using the naturally occurring substrate of the affinity moiety.

Isolated or substantially purified polynucleotides or protein compositions are disclosed. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (for example, sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein.

A polypeptide may also be produced by known conventional chemical synthesis. Methods for constructing the polypeptides or fragments thereof by synthetic means are known to those skilled in the art. The synthetically-constructed polypeptide sequences, by virtue of sharing primary, secondary or tertiary structural or conformational characteristics with native polypeptides may possess biological properties in common therewith, including biological activity.

The term 'non-naturally occurring' as used herein describes an entity (for example, a polynucleotide, a genetic mutation, a polypeptide, a plant, a plant cell and plant material) that is not formed by nature or that does not exist in nature. Such non-naturally occurring entities or artificial entities may be made, synthesized, initiated, modified, intervened, or manipulated by methods described herein or that are known in the art. Such non-naturally occurring entities or artificial entities may be made, synthesized, initiated, modified, intervened, or manipulated by man. Thus, by way of example, a non-naturally occurring plant, a non-naturally occurring plant cell or non-naturally occurring plant material may be made using traditional plant breeding techniques—such as backcrossing—or by genetic manipulation technologies—such as antisense RNA, interfering RNA, meganuclease and the like. By way of further example, a non-naturally occurring plant, a non-naturally occurring plant cell or non-naturally occurring plant material may be made by introgression of or by transferring one or more genetic mutations (for example one or more polymorphisms) from a first plant or plant cell into a second plant or plant cell (which may itself be naturally occurring), such that the resulting plant, plant cell or plant material or the progeny thereof comprises a genetic constitution (for example, a genome, a chromosome or a segment thereof) that is not formed by nature or that does not exist in nature. The resulting plant, plant cell or plant material is thus artificial or non-naturally occurring. Accordingly, an artificial or non-naturally occurring plant or plant cell may be made by modifying a genetic sequence in a first naturally occurring plant or plant cell, even if the resulting genetic sequence occurs naturally in a second plant or plant cell that comprises a different genetic background from the first plant or plant cell. In certain embodiments, a mutation is not a naturally occurring mutation that exists naturally in a nucleotide sequence or a polypeptide—such as a gene or a protein.

Differences in genetic background can be detected by phenotypic differences or by molecular biology techniques known in the art—such as nucleic acid sequencing, presence or absence of genetic markers (for example, microsatellite RNA markers).

Antibodies that are immunoreactive with the polypeptides described herein are also provided. The polypeptides, fragments, variants, fusion polypeptides, and the like, as set forth herein, can be employed as "immunogens" in producing antibodies immunoreactive therewith. Such antibodies may specifically bind to the polypeptide via the antigen-binding sites of the antibody. Specifically binding antibodies are those that will specifically recognize and bind with a polypeptide, homologues, and variants, but not with other molecules. In one embodiment, the antibodies are specific for polypeptides having an amino acid sequence as set forth herein and do not cross-react with other polypeptides.

More specifically, the polypeptides, fragment, variants, fusion polypeptides, and the like contain antigenic determinants or epitopes that elicit the formation of antibodies. These antigenic determinants or epitopes can be either linear or conformational (discontinuous). Linear epitopes are composed of a single section of amino acids of the polypeptide, while conformational or discontinuous epitopes are composed of amino acids sections from different regions of the polypeptide chain that are brought into close proximity upon polypeptide folding. Epitopes can be identified by any of the methods known in the art. Additionally, epitopes from the polypeptides can be used as research reagents, in assays, and to purify specific binding antibodies from substances such as polyclonal sera or supernatants from cultured hybridomas. Such epitopes or variants thereof can be produced using techniques known in the art such as solid-phase synthesis, chemical or enzymatic cleavage of a polypeptide, or using recombinant DNA technology.

Both polyclonal and monoclonal antibodies to the polypeptides can be prepared by conventional techniques. Hybridoma cell lines that produce monoclonal antibodies specific for the polypeptides are also contemplated herein. Such hybridomas can be produced and identified by conventional techniques. For the production of antibodies, various host animals may be immunized by injection with a polypeptide, fragment, variant, or mutants thereof. Such host animals may include, but are not limited to, rabbits, mice, and rats, to name a few. Various adjutants may be used to increase the immunological response. Depending on the host species, such adjuvants include, but are not limited to, Freund's (complete and incomplete), mineral gels such as aluminium hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. The monoclonal antibodies can be recovered by conventional techniques. Such monoclonal antibodies may be of any immunoglobulin class including IgG, IgM, IgE, IgA, IgD, and any subclass thereof.

The antibodies can also be used in assays to detect the presence of the polypeptides or fragments, either in vitro or in vivo. The antibodies also can be employed in purifying polypeptides or fragments by immunoaffinity chromatography.

Other than mutagenesis, compositions that can modulate the expression or the activity of one or more of the polynucleotides or polypeptides selected from the group consisting of NND3, CYP82E4, CYP82E5 or CYP82E10 or a combination of two, three or four thereof (eg. a combination of NND3, CYP82E4, CYP82E5 and CYP82E10) include, but are not limited to, sequence-specific polynucleotides that can interfere with the transcription of one or more endogenous gene(s); sequence-specific polynucleotides that can interfere with the translation of RNA transcripts (for example, double-stranded RNAs, siRNAs, ribozymes); sequence-specific polypeptides that can interfere with the stability of one or more proteins; sequence-specific polynucleotides that can interfere with the enzymatic activity of one or more proteins or the binding activity of one or more proteins with respect to substrates or regulatory proteins; antibodies that exhibit specificity for one or more proteins; small molecule compounds that can interfere with the stability of one or more proteins or the enzymatic activity of one or more proteins or the binding activity of one or more proteins; zinc finger proteins that bind one or more polynucleotides; and meganucleases that have activity towards one or more polynucleotides. Gene editing technologies, genetic editing technologies and genome editing technologies are well known in the art.

One method of gene editing involves the use of transcription activator-like effector nucleases (TALENs) which induce double-strand breaks which cells can respond to with repair mechanisms. Non-homologous end joining reconnects DNA from either side of a double-strand break where there is very little or no sequence overlap for annealing. This repair mechanism induces errors in the genome via insertion or deletion, or chromosomal rearrangement. Any such errors may render the gene products coded at that location non-functional. Another method of gene editing involves the use of the bacterial CRISPR/Cas system. Bacteria and archaea exhibit chromosomal elements called clustered regularly interspaced short palindromic repeats (CRISPR) that are part of an adaptive immune system that protects against invading viral and plasmid DNA. In Type II CRISPR systems, CRISPR RNAs (crRNAs) function with trans-activating crRNA (tracrRNA) and CRISPR-associated (Cas) proteins to introduce double-stranded breaks in target DNA. Target cleavage by Cas9 requires base-pairing between the crRNA and tracrRNA as well as base pairing between the crRNA and the target DNA. Target recognition is facilitated by the presence of a short motif called a protospacer-adjacent motif (PAM) that conforms to the sequence NGG. This system can be harnessed for genome editing. Cas9 is normally programmed by a dual RNA consisting of the crRNA and tracrRNA. However, the core components of these RNAs can be combined into a single hybrid 'guide RNA' for Cas9 targeting. The use of a noncoding RNA guide to target DNA for site-specific cleavage promises to be significantly more straightforward than existing technologies—such as TALENs. Using the CRISPR/Cas strategy, retargeting the nuclease complex only requires introduction of a new RNA sequence and there is no need to reengineer the specificity of protein transcription factors. Antisense technology is another well-known method that can be used to modulate the expression of a polypeptide. A polynucleotide of the gene to be repressed is cloned and operably linked to a regulatory region and a transcription termination sequence so that the antisense strand of RNA is transcribed. The recombinant construct is then transformed into a plant cell and the antisense strand of RNA is produced. The polynucleotide need not be the entire sequence of the gene to be repressed, but typically will be substantially complementary to at least a portion of the sense strand of the gene to be repressed.

A polynucleotide may be transcribed into a ribozyme, or catalytic RNA, that affects expression of an mRNA. Ribozymes can be designed to specifically pair with virtually any target RNA and cleave the phosphodiester backbone at a specific location, thereby functionally inactivating the target RNA. Heterologous polynucleotides can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. Hammerhead ribozyme sequences can be embedded in a stable RNA such as a transfer RNA (tRNA) to increase cleavage efficiency in vivo.

In one embodiment, the sequence-specific polynucleotide that can interfere with the translation of RNA transcript(s) is interfering RNA. RNA interference or RNA silencing is an evolutionarily conserved process by which specific mRNAs can be targeted for enzymatic degradation. A double-stranded RNA (double-stranded RNA) is introduced or produced by a cell (for example, double-stranded RNA virus, or interfering RNA polynucleotides) to initiate the interfering RNA pathway. The double-stranded RNA can be converted into multiple small interfering RNA duplexes of 21-24 bp length by RNases III, which are double-stranded RNA-specific endonucleases. The small interfering RNAs can be subsequently recognized by RNA-induced silencing complexes that promote the unwinding of small interfering RNA through an ATP-dependent process. The unwound antisense strand of the small interfering RNA guides the activated RNA-induced silencing complexes to the targeted mRNA comprising a sequence complementary to the small interfering RNA anti-sense strand. The targeted mRNA and the anti-sense strand can form an A-form helix, and the major groove of the A-form helix can be recognized by the activated RNA-induced silencing complexes. The target mRNA can be cleaved by activated RNA-induced silencing complexes at a single site defined by the binding site of the 5'-end of the small interfering RNA strand. The activated RNA-induced silencing complexes can be recycled to catalyze another cleavage event.

Interfering RNA expression vectors may comprise interfering RNA constructs encoding interfering RNA polynucleotides that exhibit RNA interference activity by reducing the expression level of mRNAs, pre-mRNAs, or related RNA variants. The expression vectors may comprise a promoter positioned upstream and operably-linked to an Interfering RNA construct, as further described herein. Interfering RNA expression vectors may comprise a suitable minimal core promoter, a Interfering RNA construct of interest, an upstream (5') regulatory region, a downstream (3') regulatory region, including transcription termination and polyadenylation signals, and other sequences known to persons skilled in the art, such as various selection markers.

The polynucleotides can be produced in various forms, including as double stranded structures (that is, a double-stranded RNA molecule comprising an antisense strand and a complementary sense strand), double-stranded hairpin-like structures, or single-stranded structures (that is, a ssRNA molecule comprising just an antisense strand). The structures may comprise a duplex, asymmetric duplex, hairpin or asymmetric hairpin secondary structure, having self-complementary sense and antisense strands. The double stranded interfering RNA can be enzymatically converted to double-stranded small interfering RNAs. One of the strands of the small interfering RNA duplex can anneal to a complementary sequence within the target mRNA and related RNA variants. The small interfering RNA/mRNA duplexes are recognized by RNA-induced silencing complexes that can cleave RNAs at multiple sites in a sequence-dependent manner, resulting in the degradation of the target mRNA and related RNA variants.

The double-stranded RNA molecules may include small interfering RNA molecules assembled from a single oligonucleotide in a stem-loop structure, wherein self-complementary sense and antisense regions of the small interfering RNA molecule are linked by means of a polynucleotide based or non-polynucleotide-based linker(s), as well as circular single-stranded RNA having two or more loop structures and a stem comprising self-complementary sense and antisense strands, wherein the circular RNA can be processed either in vivo or in vitro to generate an active small interfering RNA molecule capable of mediating interfering RNA.

The use of small hairpin RNA molecules is also contemplated. They comprise a specific antisense sequence in addition to the reverse complement (sense) sequence, typically separated by a spacer or loop sequence. Cleavage of the spacer or loop provides a single-stranded RNA molecule and its reverse complement, such that they may anneal to form a double-stranded RNA molecule (optionally with additional processing steps that may result in addition or removal of one, two, three or more nucleotides from the 3' end or the 5' end of either or both strands). The spacer can be of a sufficient length to permit the antisense and sense sequences to anneal and form a double-stranded structure (or stem) prior to cleavage of the spacer (and, optionally, subsequent processing steps that may result in addition or removal of one, two, three, four, or more nucleotides from the 3' end or the 5' end of either or both strands). The spacer sequence is typically an unrelated nucleotide sequence that is situated between two complementary nucleotide sequence regions which, when annealed into a double-stranded polynucleotide, comprise a small hairpin RNA. The spacer sequence generally comprises between about 3 and about 100 nucleotides.

Any RNA polynucleotide of interest can be produced by selecting a suitable sequence composition, loop size, and stem length for producing the hairpin duplex. A suitable range for designing stem lengths of a hairpin duplex, includes stem lengths of at least about 10, 11, 12, 13, 14, 15, 16, 17, 18, 19 or 20 nucleotides—such as about 14-30 nucleotides, about 30-50 nucleotides, about 50-100 nucleotides, about 100-150 nucleotides, about 150-200 nucleotides, about 200-300 nucleotides, about 300-400 nucleotides, about 400-500 nucleotides, about 500-600 nucleotides, and about 600-700 nucleotides. A suitable range for designing loop lengths of a hairpin duplex, includes loop lengths of about 4-25 nucleotides, about 25-50 nucleotides, or longer if the stem length of the hair duplex is substantial. In certain embodiments, a double-stranded RNA or ssRNA molecule is between about 15 and about 40 nucleotides in length. In another embodiment, the small interfering RNA molecule is a double-stranded RNA or ssRNA molecule between about 15 and about 35 nucleotides in length. In another embodiment, the small interfering RNA molecule is a double-stranded RNA or ssRNA molecule between about 17 and about 30 nucleotides in length. In another embodiment, the small interfering RNA molecule is a double-stranded RNA or ssRNA molecule between about 19 and about 25 nucleotides in length. In another embodiment, the small interfering RNA molecule is a double-stranded RNA or ssRNA molecule between about 21 to about 24 nucleotides in length. In certain embodiments, hairpin structures with duplexed regions longer than 21 nucleotides may promote effective small interfering RNA-directed silencing, regardless of loop sequence and length. An exemplary sequence for RNA interference are set forth in SEQ ID NO: 4.

The target mRNA sequence is typically between about 14 to about 50 nucleotides in length. The target mRNA can, therefore, be scanned for regions between about 14 and about 50 nucleotides in length that preferably meet one or more of the following criteria for a target sequence: an A+T/G+C ratio of between about 2:1 and about 1:2; an AA dinucleotide or a CA dinucleotide at the 5' end of the target sequence; a sequence of at least 10 consecutive nucleotides unique to the target mRNA (that is, the sequence is not present in other mRNA sequences from the same plant); and no "runs" of more than three consecutive guanine (G) nucleotides or more than three consecutive cytosine (C) nucleotides. These criteria can be assessed using various techniques known in the art, for example, computer programs such as BLAST can be used to search publicly available databases to determine whether the selected target sequence is unique to the target mRNA. Alternatively, a target sequence can be selected (and a small interfering RNA sequence designed) using computer software available commercially (for example, OligoEngine, Target Finder and the small interfering RNA Design Tool which are commercially available).

In one embodiment, target mRNA sequences are selected that are between about 14 and about 30 nucleotides in length that meet one or more of the above criteria. In another embodiment, target sequences are selected that are between about 16 and about 30 nucleotides in length that meet one or more of the above criteria. In a further embodiment, target sequences are selected that are between about 19 and about 30 nucleotides in length that meet one or more of the above criteria. In another embodiment, target sequences are selected that are between about 19 and about 25 nucleotides in length that meet one or more of the above criteria.

In an exemplary embodiment, the small interfering RNA molecules comprise a specific antisense sequence that is complementary to at least 12, 13, 14, 15, 16, 17, 18, 19, 20, 21, 22, 23, 24, 25, 26, 27, 28, 29, 30, or more contiguous nucleotides of any one of the polynucleotide sequences described herein.

The specific antisense sequence comprised by the small interfering RNA molecule can be identical or substantially identical to the complement of the target sequence. In one embodiment, the specific antisense sequence comprised by the small interfering RNA molecule is at least about 75%, 80%, 85%, 90%, 95%, 96%, 97%, 98%, 99% or 100% identical to the complement of the target mRNA sequence. Methods of determining sequence identity are known in the art and can be determined, for example, by using the BLASTN program of the University of Wisconsin Computer Group (GCG) software or provided on the NCBI website.

The specific antisense sequence of the small interfering RNA molecules may exhibit variability by differing (for example, by nucleotide substitution, including transition or transversion) at one, two, three, four or more nucleotides from the sequence of the target mRNA. When such nucleotide substitutions are present in the antisense strand of a double-stranded RNA molecule, the complementary nucleotide in the sense strand with which the substitute nucleotide would typically form hydrogen bond base-pairing may or may not be correspondingly substituted. Double-stranded RNA molecules in which one or more nucleotide substitution occurs in the sense sequence, but not in the antisense strand, are also contemplated. When the antisense sequence of an small interfering RNA molecule comprises one or more mismatches between the nucleotide sequence of the small interfering RNA and the target nucleotide sequence, as described above, the mismatches may be found at the 3' terminus, the 5' terminus or in the central portion of the antisense sequence.

In another embodiment, the small interfering RNA molecules comprise a specific antisense sequence that is capable of selectively hybridizing under stringent conditions to a portion of a naturally occurring target gene or target mRNA. As known to those of ordinary skill in the art, variations in stringency of hybridization conditions may be achieved by altering the time, temperature or concentration of the solutions used for the hybridization and wash steps. Suitable conditions can also depend in part on the particular nucleotide sequences used, for example the sequence of the target mRNA or gene.

One method for inducing double stranded RNA-silencing in plants is transformation with a gene construct producing hairpin RNA (see Smith et al. (2000) *Nature*, 407, 319-320). Such constructs comprise inverted regions of the target gene sequence, separated by an appropriate spacer. The insertion of a functional plant intron region as a spacer fragment additionally increases the efficiency of the gene silencing induction, due to generation of an intron spliced hairpin RNA (Wesley et al. (2001) *Plant J.*, 27, 581-590). Suitably, the stem length is about 50 nucleotides to about 1 kilobases in length. Methods for producing intron spliced hairpin RNA are well described in the art (see for example, *Bioscience, Biotechnology, and Biochemistry* (2008) 72, 2, 615-617).

Interfering RNA molecules having a duplex or double-stranded structure, for example double-stranded RNA or small hairpin RNA, can have blunt ends, or can have 3' or 5' overhangs. As used herein, "overhang" refers to the unpaired nucleotide or nucleotides that protrude from a duplex structure when a 3'-terminus of one RNA strand extends beyond the 5'-terminus of the other strand (3' overhang), or vice versa (5' overhang). The nucleotides comprising the overhang can be ribonucleotides, deoxyribonucleotides or modified versions thereof. In one embodiment, at least one strand of the interfering RNA molecule has a 3' overhang from about 1 to about 6 nucleotides in length. In other embodiments, the 3' overhang is from about 1 to about 5 nucleotides, from about 1 to about 3 nucleotides and from about 2 to about 4 nucleotides in length.

When the interfering RNA molecule comprises a 3' overhang at one end of the molecule, the other end can be blunt-ended or have also an overhang (5' or 3'). When the interfering RNA molecule comprises an overhang at both ends of the molecule, the length of the overhangs may be the same or different. In one embodiment, the interfering RNA molecule comprises 3' overhangs of about 1 to about 3 nucleotides on both ends of the molecule. In a further embodiment, the interfering RNA molecule is a double-stranded RNA having a 3' overhang of 2 nucleotides at both ends of the molecule. In yet another embodiment, the nucleotides comprising the overhang of the interfering RNA are TT dinucleotides or UU dinucleotides.

When determining the percentage identity of the interfering RNA molecule comprising one or more overhangs to the target mRNA sequence, the overhang(s) may or may not be taken into account. For example, the nucleotides from a 3' overhang and up to 2 nucleotides from the 5'- or 3'-terminus of the double strand may be modified without significant loss of activity of the small interfering RNA molecule.

The interfering RNA molecules can comprise one or more 5' or 3'-cap structures. The interfering RNA molecule can comprise a cap structure at the 3'-end of the sense strand, the antisense strand, or both the sense and antisense strands; or at the 5'-end of the sense strand, the antisense strand, or both the sense and antisense strands of the interfering RNA molecule. Alternatively, the interfering RNA molecule can comprise a cap structure at both the 3'-end and 5'-end of the interfering RNA molecule. The term "cap structure" refers to a chemical modification incorporated at either terminus of an oligonucleotide, which protects the molecule from exonuclease degradation, and may also facilitate delivery or localisation within a cell.

Another modification applicable to interfering RNA molecules is the chemical linkage to the interfering RNA molecule of one or more moieties or conjugates which enhance the activity, cellular distribution, cellular uptake, bioavailability or stability of the interfering RNA molecule. The polynucleotides may be synthesized or modified by methods well established in the art. Chemical modifications may include, but are not limited to 2' modifications, introduction of non-natural bases, covalent attachment to a ligand, and replacement of phosphate linkages with thiophosphate linkages. In this embodiment, the integrity of the duplex structure is strengthened by at least one, and typically two, chemical linkages. Chemical linking may be achieved by any of a variety of well-known techniques, for example by introducing covalent, ionic or hydrogen bonds; hydrophobic interactions, van der Waals or stacking interactions; by means of metal-ion coordination, or through use of purine analogues.

The nucleotides at one or both of the two single strands may be modified to modulate the activation of cellular enzymes, such as, for example, without limitation, certain nucleases. Techniques for reducing or inhibiting the activation of cellular enzymes are known in the art including, but not limited to, 2'-amino modifications, 2'-fluoro modifications, 2'-alkyl modifications, uncharged backbone modifications, morpholino modifications, 2'-O-methyl modifications, and phosphoramidate. Thus, at least one 2'-hydroxyl group of the nucleotides on a double-stranded RNA is replaced by a chemical group. Also, at least one nucleotide may be modified to form a locked nucleotide. Such locked nucleotide contains a methylene or ethylene bridge that connects the 2'-oxygen of ribose with the 4'-carbon of ribose. Introduction of a locked nucleotide into an oligonucleotide improves the affinity for complementary sequences and increases the melting temperature by several degrees.

Ligands may be conjugated to an interfering RNA molecule, for example, to enhance its cellular absorption. In certain embodiments, a hydrophobic ligand is conjugated to the molecule to facilitate direct permeation of the cellular membrane. These approaches have been used to facilitate cell permeation of antisense oligonucleotides. In certain instances, conjugation of a cationic ligand to oligonucleotides often results in improved resistance to nucleases. Representative examples of cationic ligands include propylammonium and dimethylpropylammonium. Anti-sense oligonucleotides can retain their high binding affinity to mRNA when the cationic ligand is dispersed throughout the oligonucleotide.

The molecules and polynucleotides described herein may be prepared using well-known techniques of solid-phase synthesis. Any other means for such synthesis known in the art may additionally or alternatively be employed.

Various embodiments are directed to expression vectors comprising one or more of the polynucleotides or interfering RNA constructs that comprise one or more polynucleotides described herein. An exemplary interfering RNA construct is shown in SEQ ID NO:4.

Various embodiments are directed to expression vectors comprising one or more of the polynucleotides or one or more interfering RNA constructs described herein.

Various embodiments are directed to expression vectors comprising one or more polynucleotides or one or more interfering RNA constructs encoding one or more interfering RNA polynucleotides described herein that are capable of self-annealing to form a hairpin structure, in which the construct comprises (a) one or more of the polynucleotides described herein; (b) a second sequence encoding a spacer element that forms a loop of the hairpin structure; and (c) a third sequence comprising a reverse complementary sequence of the first sequence, positioned in the same orientation as the first sequence, wherein the second sequence is positioned between the first sequence and the third sequence, and the second sequence is operably-linked to the first sequence and to the third sequence.

The disclosed sequences can be utilised for constructing various polynucleotides that do not form hairpin structures. For example, a double-stranded RNA can be formed by (1) transcribing a first strand of the DNA by operably-linking to a first promoter, and (2) transcribing the reverse complementary sequence of the first strand of the DNA fragment by operably-linking to a second promoter. Each strand of the polynucleotide can be transcribed from the same expression vector, or from different expression vectors. The RNA duplex having RNA interference activity can be enzymatically converted to small interfering RNAs to modulate RNA levels.

Thus, various embodiments are directed to expression vectors comprising one or more polynucleotides or interfering RNA constructs described herein encoding interfering RNA polynucleotides capable of self-annealing, in which the construct comprises (a) one or more of the polynucleotides described herein; and (b) a second sequence comprising a complementary (for example, reverse complementary) sequence of the first sequence, positioned in the same orientation as the first sequence.

Various compositions and methods are provided for modulating the endogenous expression levels of one or more of the polypeptides described herein (or any combination thereof as described herein) by promoting co-suppression of gene expression. The phenomenon of co-suppression occurs as a result of introducing multiple copies of a transgene into a plant cell host. Integration of multiple copies of a transgene can result in modulated expression of the transgene and the targeted endogenous gene. The degree of co-suppression is dependent on the degree of sequence identity between the transgene and the targeted endogenous gene. The silencing of both the endogenous gene and the transgene can occur by extensive methylation of the silenced loci (that is, the endogenous promoter and endogenous gene of interest) that can preclude transcription. Alternatively, in some cases, co-suppression of the endogenous gene and the transgene can occur by post transcriptional gene silencing, in which transcripts can be produced but enhanced rates of degradation preclude accumulation of transcripts. The mechanism for co-suppression by post-transcriptional gene silencing is thought to resemble RNA interference, in that RNA seems to be both an important initiator and a target in these processes, and may be mediated at least in part by the same molecular machinery, possibly through RNA-guided degradation of mRNAs.

Co-suppression of nucleic acids can be achieved by integrating multiple copies of the nucleic acid or fragments thereof, as transgenes, into the genome of a plant of interest. The host plant can be transformed with an expression vector comprising a promoter operably-linked to the nucleic acid or fragments thereof. Various embodiments are directed to expression vectors for promoting co-suppression of endogenous genes comprising a promoter operably-linked to a polynucleotide.

Various embodiments are directed to methods for modulating the expression level of one or more of the polynucleotide(s) described herein (or any combination thereof as described herein) by integrating multiple copies of the polynucleotide(s) into a (tobacco) plant genome, comprising: transforming a plant cell host with an expression vector that comprises a promoter operably-linked to a polynucleotide.

Various compositions and methods are provided for modulating the endogenous gene expression level by modulating the translation of mRNA. A host (tobacco) plant cell can be transformed with an expression vector comprising: a promoter operably-linked to a polynucleotide, positioned in anti-sense orientation with respect to the promoter to enable the expression of RNA polynucleotides having a sequence complementary to a portion of mRNA.

Various expression vectors for modulating the translation of mRNA may comprise: a promoter operably-linked to a polynucleotide in which the sequence is positioned in anti-sense orientation with respect to the promoter. The lengths of anti-sense RNA polynucleotides can vary, and may be from about 15-20 nucleotides, about 20-30 nucleotides, about 30-50 nucleotides, about 50-75 nucleotides, about 75-100 nucleotides, about 100-150 nucleotides, about 150-200 nucleotides, and about 200-300 nucleotides.

Genes can also be targeted for inactivation by introducing transposons (for example, IS elements) into the genomes of plants of interest. These mobile genetic elements can be introduced by sexual cross-fertilization and insertion mutants can be screened for loss in protein activity. The disrupted gene in a parent plant can be introduced into other plants by crossing the parent plant with plant not subjected to transposon-induced mutagenesis by, for example, sexual cross-fertilization. Any standard breeding techniques known to persons skilled in the art can be utilized. In one embodiment, one or more genes can be inactivated by the insertion of one or more transposons. Mutations can result in homozygous disruption of one or more genes, in heterozygous disruption of one or more genes, or a combination of both homozygous and heterozygous disruptions if more than one gene is disrupted. Suitable transposable elements include retrotransposons, retroposons, and SINE-like elements. Such methods are known to persons skilled in the art.

Alternatively, genes can be targeted for inactivation by introducing ribozymes derived from a number of small circular RNAs that are capable of self-cleavage and replication in plants. These RNAs can replicate either alone (viroid RNAs) or with a helper virus (satellite RNAs). Examples of suitable RNAs include those derived from avocado sunblotch viroid and satellite RNAs derived from tobacco ringspot virus, lucerne transient streak virus, velvet tobacco mottle virus, *solanum nodiflorum* mottle virus, and subterranean clover mottle virus. Various target RNA-specific ribozymes are known to persons skilled in the art.

As discussed herein, the expression of one or more polypeptides can be modulated by non-transgenic means—such as creating one or more mutations in one or more genes, as discussed herein. Methods that introduce a mutation randomly in a gene sequence can include chemical mutagenesis, EMS mutagenesis and radiation mutagenesis. Methods that introduce one or more targeted mutations into a cell include but are not limited to genome editing technology, particularly zinc finger nuclease-mediated mutagenesis and targeting induced local lesions in genomes (TILLING), homologous recombination, oligonucleotide-directed mutagenesis, and meganuclease-mediated mutagenesis. In one embodiment, TILLING is used. This is a mutagenesis technology that can be used to generate and/or identify polynucleotides encoding polypeptides with modified expression and/or activity. TILLING also allows selection of plants carrying such mutants. TILLING combines high-density mutagenesis with high-throughput screening methods. Methods for TILLING are well known in the art (see McCallum et al., (2000) *Nat Biotechnol* 18: 455-457 and Stemple (2004) *Nat Rev Genet* 5(2): 145-50).

Some non-limiting examples of mutations are deletions, insertions and missense mutations of at least one nucleotide, single nucleotide polymorphisms and a simple sequence repeat. After mutation, screening can be performed to identify mutations that create premature stop codons or otherwise non-functional genes. After mutation, screening can be performed to identify mutations that create functional genes that are capable of being expressed at elevated levels. Screening of mutants can be carried out by sequencing, or by the use of one or more probes or primers specific to the gene or protein. Specific mutations in polynucleotides can also be created that can result in modulated gene expression, modulated stability of mRNA, or modulated stability of protein. Such plants are referred to herein as "non-naturally occurring" or "mutant" plants. Typically, the mutant or non-naturally occurring plants will include at least a portion of foreign or synthetic or man-made nucleic acid (for example, DNA or RNA) that was not present in the plant before it was manipulated. The foreign nucleic acid may be a single nucleotide, two or more nucleotides, two or more contiguous nucleotides or two or more non-contiguous nucleotides—such as at least 10, 20, 30, 40, 50, 100, 200, 300, 400, 500, 600, 700, 800, 900, 1000, 1100, 1200, 1300, 1400 or 1500 or more contiguous or non-contiguous nucleotides.

The mutant or non-naturally occurring plants or plant cells can have any combination of one or more mutations in one or more genes which results in modulated protein levels. For example, the mutant or non-naturally occurring plants or plant cells may have a single mutation in a single gene; multiple mutations in a single gene; a single mutation in two or more or three or more or four or more genes; or multiple mutations in two or more or three or more or four or more genes. Examples of such mutations are described herein. By way of further example, the mutant or non-naturally occurring plants or plant cells may have one or more mutations in a specific portion of the gene(s)—such as in a region of the gene that encodes an active site of the protein or a portion thereof. By way of further example, the mutant or non-naturally occurring plants or plant cells may have one or more mutations in a region outside of one or more gene(s)—such as in a region upstream or downstream of the gene it regulates provided that they modulate the activity or expression of the gene(s). Upstream elements can include promoters, enhancers or transcription factors. Some elements—such as enhancers—can be positioned upstream or downstream of the gene it regulates. The element(s) need not be located near to the gene that it regulates since some elements have been found located several hundred thousand base pairs upstream or downstream of the gene that it regulates. The mutant or non-naturally occurring plants or plant cells may have one or more mutations located within the first 100 nucleotides of the gene(s), within the first 200 nucleotides of the gene(s), within the first 300 nucleotides of the gene(s), within the first 400 nucleotides of the gene(s), within the first 500 nucleotides of the gene(s), within the first 600 nucleotides of the gene(s), within the first 700 nucleotides of the gene(s), within the first 800 nucleotides of the gene(s), within the first 900 nucleotides of the gene(s), within the first 1000 nucleotides of the gene(s), within the first 1100 nucleotides of the gene(s), within the first 1200 nucleotides of the gene(s), within the first 1300 nucleotides of the gene(s), within the first 1400 nucleotides of the gene(s) or within the first 1500 nucleotides of the gene(s). The mutant or non-naturally occurring plants or plant cells may have one or more mutations located within the first, second, third, fourth, fifth, sixth, seventh, eighth, ninth, tenth, eleventh, twelfth, thirteenth, fourteenth or fifteenth set of 100 nucleotides of the gene(s) or combinations thereof. Mutant or non-naturally occurring plants or plant cells (for example, mutant, non-naturally occurring or transgenic plants or plant cells and the like, as described herein) comprising the mutant polypeptide variants are disclosed.

In one embodiment, seeds from plants are mutagenised and then grown into first generation mutant plants. The first generation plants are then allowed to self-pollinate and seeds from the first generation plant are grown into second generation plants, which are then screened for mutations in their loci. Though the mutagenized plant material can be screened for mutations, an advantage of screening the second generation plants is that all somatic mutations correspond to germline mutations. One of skill in the art would understand that a variety of plant materials, including but not limited to, seeds, pollen, plant tissue or plant cells, may be mutagenised in order to create the mutant plants. However, the type of plant material mutagenised may affect when the plant nucleic acid is screened for mutations. For example, when pollen is subjected to mutagenesis prior to pollination of a non-mutagenized plant the seeds resulting from that pollination are grown into first generation plants. Every cell of the first generation plants will contain mutations created in the pollen; thus these first generation plants may then be screened for mutations instead of waiting until the second generation.

Mutagens that create primarily point mutations and short deletions, insertions, transversions, and or transitions, including chemical mutagens or radiation, may be used to create the mutations. Mutagens include, but are not limited to, ethyl methanesulfonate, methylmethane sulfonate, N-ethyl-N-nitrosurea, triethylmelamine, N-methyl-N-nitrosourea, procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine, nitrosoguanidine, 2-aminopurine, 7,12 dimethyl-benz(a)anthracene, ethylene oxide, hexamethylphosphoramide, bisulfan, diepoxyalkanes (diepoxyoctane, diepoxybutane, and the like), 2-methoxy-6-chloro-9[3-(ethyl-2-chloro-ethyl)aminopropylamino]acridine dihydrochloride and formaldehyde.

Spontaneous mutations in the locus that may not have been directly caused by the mutagen are also contemplated provided that they result in the desired phenotype. Suitable mutagenic agents can also include, for example, ionising radiation—such as X-rays, gamma rays, fast neutron irradiation and UV radiation. Any method of plant nucleic acid preparation known to those of skill in the art may be used to prepare the plant nucleic acid for mutation screening.

Prepared nucleic acid from individual plants, plant cells, or plant material can optionally be pooled in order to expedite screening for mutations in the population of plants originating from the mutagenized plant tissue, cells or material. One or more subsequent generations of plants, plant cells or plant material can be screened. The size of the optionally pooled group is dependent upon the sensitivity of the screening method used.

After the nucleic acid samples are optionally pooled, they can be subjected to polynucleotide-specific amplification techniques, such as Polymerase Chain Reaction. Any one or more primers or probes specific to the gene or the sequences immediately adjacent to the gene may be utilized to amplify the sequences within the optionally pooled nucleic acid sample. Suitably, the one or more primers or probes are designed to amplify the regions of the locus where useful mutations are most likely to arise. Most preferably, the primer is designed to detect mutations within regions of the polynucleotide. Additionally, it is preferable for the primer(s) and probe(s) to avoid known polymorphic sites in order to ease screening for point mutations. To facilitate detection of amplification products, the one or more primers or probes may be labelled using any conventional labelling method. Primer(s) or probe(s) can be designed based upon the sequences described herein using methods that are well understood in the art.

To facilitate detection of amplification products, the primer(s) or probe(s) may be labelled using any conventional labelling method. These can be designed based upon the sequences described herein using methods that are well understood in the art. Polymorphisms may be identified by means known in the art and some have been described in the literature.

In a further aspect there is provided a method of preparing a mutant plant. The method involves providing at least one cell of a plant comprising a gene encoding a functional polynucleotide described herein (or any combination thereof as described herein). Next, the at least one cell of the plant is treated under conditions effective to modulate the activity of the polynucleotide(s) described herein. The at least one mutant plant cell is then propagated into a mutant plant, where the mutant plant has a modulated level of polypeptide(s) described (or any combination thereof as described herein) as compared to that of a control plant. In one embodiment of this method of making a mutant plant, the treating step involves subjecting the at least one cell to a chemical mutagenising agent as described above and under conditions effective to yield at least one mutant plant cell. In another embodiment of this method, the treating step involves subjecting the at least one cell to a radiation source under conditions effective to yield at least one mutant plant cell. The term "mutant plant" includes mutants plants in which the genotype is modified as compared to a control plant, suitably by means other than genetic engineering or genetic modification.

In certain embodiments, the mutant plant, mutant plant cell or mutant plant material may comprise one or more mutations that have occurred naturally in another plant, plant cell or plant material and confer a desired trait. This mutation can be incorporated (for example, introgressed) into another plant, plant cell or plant material (for example, a plant, plant cell or plant material with a different genetic background to the plant from which the mutation was derived) to confer the trait thereto. Thus by way of example, a mutation that occurred naturally in a first plant may be introduced into a second plant—such as a second plant with a different genetic background to the first plant. The skilled person is therefore able to search for and identify a plant carrying naturally in its genome one or more mutant alleles of the genes described herein which confer a desired trait. The mutant allele(s) that occurs naturally can be transferred to the second plant by various methods including breeding, backcrossing and introgression to produce a lines, varieties or hybrids that have one or more mutations in the genes described herein. Plants showing a desired trait may be screened out of a pool of mutant plants. Suitably, the selection is carried out utilising the knowledge of the nucleotide sequences as described herein. Consequently, it is possible to screen for a genetic trait as compared to a control. Such a screening approach may involve the application of conventional nucleic acid amplification and/or hybridization techniques as discussed herein. Thus, a further aspect of the present invention relates to a method for identifying a mutant plant comprising the steps of: (a) providing a sample comprising nucleic acid from a plant; and (b) determining the nucleic acid sequence of the polynucleotide, wherein a difference in the sequence of the polynucleotide as compared to the polynucleotide sequence of a control plant is indicative that said plant is a mutant plant. In another aspect there is provided a method for identifying a mutant plant which accumulates reduced levels of nornicotine and/or at least NNN as compared to a control plant comprising the steps of: (a) providing a sample from a plant to be screened; (b) determining if said sample comprises one or more mutations in one or more of the polynucleotides described herein; and (c) determining at least the nornicotine and/or NNN content of said plant. Suitably at least the NNN content is determined in green leaves or in smoke.

In another aspect there is provided a method for preparing a mutant plant which has reduced levels of nornicotine and/or at least NNN as compared to a control plant comprising the steps of: (a) providing a sample from a first plant; (b) determining if said sample comprises one or more mutations in one or more the polynucleotides described herein that result in reduced levels of nornicotine and/or at least NNN; and (c) transferring the one or more mutations into a second plant. Suitably at least the NNN content is determined in green leaves or in smoke. The mutation(s) can be transferred into the second plant using various methods that are known in the art—such as by genetic engineering, genetic manipulation, introgression, plant breeding, backcrossing and the like. In one embodiment, the first plant is a naturally occurring plant. In one embodiment, the second plant has a different genetic background to the first plant.

In another aspect there is provided a method for preparing a mutant plant which has reduced levels of nornicotine and/or at least NNN as compared to a control plant comprising the steps of: (a) providing a sample from a first plant; (b) determining if said sample comprises one or more mutations in one or more of the polynucleotides described herein that results in reduced levels of nornicotine and/or at least NNN; and (c) introgressing the one or more mutations from the first plant into a second plant. Suitably at least the NNN content is determined in green leaves or in smoke. In one embodiment, the step of introgressing comprises plant breeding, optionally including backcrossing and the like. In one embodiment, the first plant is a naturally occurring plant. In one embodiment, the second plant has a different genetic background to the first plant. In one embodiment, the first plant is not a cultivar or an elite cultivar. In one embodiment, the second plant is a cultivar or an elite cultivar. A further aspect relates to a mutant plant (including a cultivar or elite cultivar mutant plant) obtained or obtainable by the methods described herein.

In certain embodiments, the "mutant plants" may have one or more mutations localised only to a specific region of the plant—such as within the sequence of the one or more polynucleotide(s) described herein. According to this embodiment, the remaining genomic sequence of the mutant plant will be the same or substantially the same as the plant prior to the mutagenesis.

In certain embodiments, the mutant plants may have one or more mutations localised in more than one region of the plant—such as within the sequence of one or more of the polynucleotides described herein and in one or more further regions of the genome. According to this embodiment, the remaining genomic sequence of the mutant plant will not be the same or will not be substantially the same as the plant prior to the mutagenesis. In certain embodiments, the mutant plants may not have one or more mutations in one or more, two or more, three or more, four or more or five or more exons of the polynucleotide(s) described herein; or may not have one or more mutations in one or more, two or more, three or more, four or more or five or more introns of the polynucleotide(s) described herein; or may not have one or more mutations in a promoter of the polynucleotide(s) described herein; or may not have one or more mutations in the 3' untranslated region of the polynucleotide(s) described herein; or may not have one or more mutations in the 5' untranslated region of the polynucleotide(s) described herein; or may not have one or more mutations in the coding region of the polynucleotide(s) described herein; or may not have one or more mutations in the non-coding region of the polynucleotide(s) described herein; or any combination of two or more, three or more, four or more, five or more; or six or more thereof parts thereof.

In a further aspect there is provided a method of identifying a plant, a plant cell or plant material comprising a mutation in a gene encoding a polynucleotide described herein comprising: (a) subjecting a plant, a plant cell or plant material to mutagenesis; (b) obtaining a nucleic acid sample from said plant, plant cell or plant material or descendants thereof; and (c) determining the nucleic acid sequence of the gene encoding a polynucleotide described herein or a variant or a fragment thereof, wherein a difference in said sequence is indicative of one or more mutations therein.

Zinc finger proteins can be used to modulate the expression or the activity of one or more of the polynucleotides described herein. In various embodiments, a genomic DNA sequence comprising a part of or all of the coding sequence of the polynucleotide is modified by zinc finger nuclease-mediated mutagenesis. The genomic DNA sequence is searched for a unique site for zinc finger protein binding. Alternatively, the genomic DNA sequence is searched for two unique sites for zinc finger protein binding wherein both sites are on opposite strands and close together, for example, 1, 2, 3, 4, 5, 6 or more basepairs apart. Accordingly, zinc finger proteins that bind to polynucleotides are provided.

A zinc finger protein may be engineered to recognize a selected target site in a gene. A zinc finger protein can comprise any combination of motifs derived from natural zinc finger DNA-binding domains and non-natural zinc finger DNA-binding domains by truncation or expansion or a process of site-directed mutagenesis coupled to a selection method such as, but not limited to, phage display selection, bacterial two-hybrid selection or bacterial one-hybrid selection. The term "non-natural zinc finger DNA-binding domain" refers to a zinc finger DNA-binding domain that binds a three-base pair sequence within the target nucleic acid and that does not occur in the cell or organism comprising the nucleic acid which is to be modified. Methods for the design of zinc finger protein which binds specific nucleotide sequences which are unique to a target gene are known in the art.

A zinc finger nuclease may be constructed by making a fusion of a first polynucleotide coding for a zinc finger protein that binds to a polynucleotide, and a second polynucleotide coding for a non-specific endonuclease such as, but not limited to, those of a Type IIS endonuclease. A fusion protein between a zinc finger protein and the nuclease may comprise a spacer consisting of two base pairs or alternatively, the spacer can consist of three, four, five, six, seven or more base pairs. In various embodiments, a zinc finger nuclease introduces a double stranded break in a regulatory region, a coding region, or a non-coding region of a genomic DNA sequence of a polynucleotide and leads to a reduction of the level of expression of a polynucleotide, or a reduction in the activity of the protein encoded thereby. Cleavage by zinc finger nucleases frequently results in the deletion of DNA at the cleavage site following DNA repair by non-homologous end joining.

In other embodiments, a zinc finger protein may be selected to bind to a regulatory sequence of a polynucleotide. More specifically, the regulatory sequence may comprise a transcription initiation site, a start codon, a region of an exon, a boundary of an exon-intron, a terminator, or a stop codon. Accordingly, the invention provides a mutant, non-naturally occurring or transgenic plant or plant cells, produced by zinc finger nuclease-mediated mutagenesis in the vicinity of or within one or more polynucleotides described herein, and methods for making such a plant or plant cell by zinc finger nuclease-mediated mutagenesis. Methods for delivering zinc finger protein and zinc finger nuclease to a tobacco plant are similar to those described below for delivery of meganuclease.

In another aspect, methods for producing mutant, non-naturally occurring or transgenic or otherwise genetically-modified plants using meganucleases, such as I-CreI, are described. Naturally occurring meganucleases as well as recombinant meganucleases can be used to specifically cause a double-stranded break at a single site or at relatively few sites in the genomic DNA of a plant to allow for the disruption of one or more polynucleotides described herein. The meganuclease may be an engineered meganuclease with altered DNA-recognition properties. Meganuclease proteins can be delivered into plant cells by a variety of different mechanisms known in the art.

The disclosure encompass the use of meganucleases to inactivate a polynucleotide(s) described herein (or any combination thereof as described herein) in a plant cell or plant. Particularly, the invention provides a method for inactivating a polynucleotide in a plant using a meganuclease comprising: a) providing a plant cell comprising a polynucleotide as described herein; (b) introducing a meganuclease or a construct encoding a meganuclease into said plant cell; and (c) allowing the meganuclease to substantially inactivate the polynucleotide(s)

Meganucleases can be used to cleave meganuclease recognition sites within the coding regions of a polynucleotide. Such cleavage frequently results in the deletion of DNA at the meganuclease recognition site following mutagenic DNA repair by non-homologous end joining. Such mutations in the gene coding sequence are typically sufficient to inactivate the gene. This method to modify a plant cell involves, first, the delivery of a meganuclease expression cassette to a plant cell using a suitable transformation method. For highest efficiency, it is desirable to link the meganuclease expression cassette to a selectable marker and select for successfully transformed cells in the presence of a selection agent. This approach will result in the integration of the meganuclease expression cassette into the genome, however, which may not be desirable if the plant is likely to require regulatory approval. In such cases, the meganuclease expression cassette (and linked selectable marker gene) may be segregated away in subsequent plant generations using conventional breeding techniques. Alternatively, plant cells may be initially be transformed with a meganuclease expression cassette lacking a selectable marker and may be grown on media lacking a selection agent. Under such conditions, a fraction of the treated cells will acquire the meganuclease expression cassette and will express the engineered meganuclease transiently without integrating the meganuclease expression cassette into the genome. Because it does not account for transformation efficiency, this latter transformation procedure requires that a greater number of treated cells be screened to obtain the desired genome modification. The above approach can also be applied to modify a plant cell when using a zinc finger protein or zinc finger nuclease.

Following delivery of the meganuclease expression cassette, plant cells are grown, initially, under conditions that are typical for the particular transformation procedure that was used. This may mean growing transformed cells on media at temperatures below 26° C., frequently in the dark. Such standard conditions can be used for a period of time, preferably 1-4 days, to allow the plant cell to recover from the transformation process. At any point following this initial recovery period, growth temperature may be raised to stimulate the activity of the engineered meganuclease to cleave and mutate the meganuclease recognition site.

For certain applications, it may be desirable to precisely remove the polynucleotide from the genome of the plant. Such applications are possible using a pair of engineered meganucleases, each of which cleaves a meganuclease recognition site on either side of the intended deletion. TAL Effector Nucleases (TALENs) that are able to recognize and bind to a gene and introduce a double-strand break into the genome can also be used. Thus, in another aspect, methods for producing mutant, non-naturally occurring or transgenic or otherwise genetically-modified plants as described herein using TAL Effector Nucleases are contemplated.

Plants suitable for use in genetic modification include, but are not limited to, monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genera *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca, Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis,* and *Zea.*

Suitable species may include *Panicum* spp., *Sorghum* spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cord-grass), *Medicago sativa* (alfalfa), *Arundo donax* (giant reed), *Secale cereale* (rye), *Salix* spp. (willow), *Eucalyptus* spp. (eucalyptus), Triticosecale (tritic wheat times rye), bamboo, *Helianthus annuus* (sunflower), *Carthamus tinctorius* (safflower), *Jatropha curcas* (jatropha), *Ricinus communis* (castor), *Elaeis guineensis* (palm), *Linum usitatissimum* (flax), *Brassica juncea, Beta vulgaris* (sugarbeet), *Manihot esculenta* (cassaya), *Lycopersicon esculentum* (tomato), *Lactuca sativa* (lettuce), *Musyclise alca* (banana), *Solanum tuberosum* (potato), *Brassica oleracea* (broccoli, cauliflower, Brussels sprouts), *Camellia sinensis* (tea), *Fragaria ananassa* (strawberry), *Theobroma cacao* (cocoa), *Coffe61lycliseca* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), *Solanum melongena* (eggplant), *Rosa* spp. (rose), *Dianthus caryophyllus* (carnation), *Petunia* spp. (*petunia*), *Poinsettia pulcherrima* (poinsettia), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple), *Hordeum vulgare* (barley), *Poa pratensis* (bluegrass), *Lolium* spp. (ryegrass) and *Phleum pratense* (timothy), *Panicum virgatum* (switchgrass), *Sorghu61lyclise61 or* (sorghum, sudangrass), *Miscanthus giganteus* (*miscanthus*), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

Various embodiments are directed to mutant tobacco, non-naturally occurring tobacco or transgenic tobacco plants or plant cells modified to modulate gene expression levels thereby producing a plant or plant cell—such as a tobacco plant or plant cell—in which the expression level of a polypeptide is modulated within tissues of interest as compared to a control. The disclosed compositions and methods can be applied to any species of the genus *Nicotiana*, including *N. rustica* and *N. tabacum* (for example, LA B21, LN KY171, TI 1406, Basma, Galpao, Perique, Beinhart 1000-1, and Petico). Other species include *N. acaulis, N. acuminata, N. africana, N. alata, N. ameghinoi, N. amplexicaulis, N. arentsii, N. attenuata, N. azambujae, N. benavidesii, N. benthamiana, N. bigelovii, N. bonariensis, N. cavicola, N. clevelandii, N. cordifolia, N. corymbosa, N. debneyi, N. excelsior, N. forgetiana, N. fragrans, N. glauca, N. glutinosa, N. goodspeedii, N. gossei, N. hybrid, N. ingulba, N. kawakamii, N. knightiana, N. langsdorffii, N. linearis, N. longiflora, N. maritima, N. megalosiphon, N. miersii, N. noctiflora, N. nudicaulis, N. obtusifolia, N. occidentalis, N. occidentalis* subsp. *hesperis, N. otophora, N. paniculata, N. pauciflora, N. petunioides, N. plumbaginifolia, N. quadrivalvis, N. raimondii, N. repanda, N. rosulata, N. rosulata* subsp. *ingulba, N. rotundifolia, N. setchellii, N. simulans, N. solanifolia, N. spegazzinii, N. stocktonii, N. suaveolens, N. sylvestris, N. thyrsiflora, N. tomentosa, N. tomentosiformis, N. trigonophylla, N. umbratica, N. undulata, N. velutina, N. wigandioides,* and *N. x sanderae.*

The use of tobacco cultivars and elite tobacco cultivars is also contemplated herein. The transgenic, non-naturally occurring or mutant plant may therefore be a tobacco variety or elite tobacco cultivar that comprises one or more transgenes, or one or more genetic mutations or a combination thereof. The genetic mutation(s) (for example, one or more polymorphisms) can be mutations that do not exist naturally in the individual tobacco variety or tobacco cultivar (for example, elite tobacco cultivar) or can be genetic mutation(s) that do occur naturally provided that the mutation does not occur naturally in the individual tobacco variety or tobacco cultivar (for example, elite tobacco cultivar).

Particularly useful *Nicotiana tabacum* varieties include Burley type, dark type, flue-cured type, and Oriental type tobaccos. Non-limiting examples of varieties or cultivars are: BD 64, CC 101, CC 200, CC 27, CC 301, CC 400, CC 500, CC 600, CC 700, CC 800, CC 900, Coker 176, Coker 319, Coker 371 Gold, Coker 48, CD 263, DF911, DT 538 LC Galpao tobacco, GL 26H, GL 350, GL 600, GL 737, GL 939, GL 973, HB 04P, HB 04P LC, HB3307PLC, Hybrid 403LC, Hybrid 404LC, Hybrid 501 LC, K 149, K 326, K 346, K 358, K394, K 399, K 730, KDH 959, KT 200, KT204LC, KY10, KY14, KY 160, KY 17, KY 171, KY 907, KY907LC, KY14xL8 LC, Little Crittenden, McNair 373, McNair 944, msKY 14xL8, Narrow Leaf Madole, Narrow Leaf Madole LC, NBH 98, N-126, N-777LC, N-7371LC, NC 100, NC 102, NC 2000, NC 291, NC 297, NC 299, NC 3, NC 4, NC 5, NC 6, NC7, NC 606, NC 71, NC 72, NC 810, NC BH 129, NC 2002, Neal Smith Madole, OXFORD 207, PD 7302 LC, PD 7309 LC, PD 7312 LC, 'Perique' tobacco, PVH03, PVH09, PVH19, PVH50, PVH51, R 610, R 630, R 7-11, R 7-12, RG 17, RG 81, RG H51, RGH 4, RGH 51, RS 1410, Speight 168, Speight 172, Speight 179, Speight 210, Speight 220, Speight 225, Speight 227, Speight 234, Speight G-28, Speight G-70, Speight H-6, Speight H20, Speight NF3, TI 1406, TI 1269, TN 86, TN86LC, TN 90, TN 97, TN97LC, TN D94, TN D950, TR (Tom Rosson) Madole, VA 309, VA359, AA 37-1, B13P, Xanthi (Mitchell-Mor), Bel-W3, 79-615, Samsun Holmes NN, KTRDC number 2 Hybrid 49, Burley 21, KY8959, KY9, MD 609, PG01, PG04, PO1, PO2, PO3, RG11, RG 8, VA509, AS44, Banket A1, Basma Drama B84/31, Basma I Zichna ZP4/B, Basma Xanthi BX 2A, Batek, Besuki Jember, C104, Coker 347, Criollo Misionero, Delcrest, Djebel 81, DVH 405, Galpao Comum, HB04P, Hicks Broadleaf, Kabakulak Elassona, Kutsage E1, LA BU 21, NC 2326, NC 297, PVH 2110, Red Russian, Samsun, Saplak, Simmaba, Talgar 28, Wislica, Yayaldag, Prilep HC-72, Prilep P23, Prilep PB 156/1, Prilep P12-2/1, Yaka JK-48, Yaka JB 125/3, TI-1068, KDH-960, TI-1070, TW136, Basma, TKF 4028, L8, TKF 2002, GR141, Basma xanthi, GR149, GR153, Petit Havana. Low converter subvarieties of the above, even if not specifically identified herein, are also contemplated.

Embodiments are also directed to compositions and methods for producing mutant plants, non-naturally occurring plants, hybrid plants, or transgenic plants that have been modified to modulate the expression or activity of a polynucleotide(s) described herein (or any combination thereof as described herein). Advantageously, the mutant plants, non-naturally occurring plants, hybrid plants, or transgenic plants that are obtained may be similar or substantially the same in overall appearance to control plants. Various phenotypic characteristics such as degree of maturity, number of leaves per plant, stalk height, leaf insertion angle, leaf size (width and length), internode distance, and lamina-midrib ratio can be assessed by field observations.

One aspect relates to a seed of a mutant plant, a non-naturally occurring plant, a hybrid plant or a transgenic plant described herein. Preferably, the seed is a tobacco seed. A further aspect relates to pollen or an ovule of a mutant plant, a non-naturally occurring plant, a hybrid plant or a transgenic plant that is described herein. In addition, there is provided a mutant plant, a non-naturally occurring plant, a hybrid plant or a transgenic plant as described herein which further comprises a nucleic acid conferring male sterility.

Also provided is a tissue culture of regenerable cells of the mutant plant, non-naturally occurring plant, hybrid plant, or transgenic plant or a part thereof as described herein, which culture regenerates plants capable of expressing all the morphological and physiological characteristics of the parent. The regenerable cells include but are not limited to cells from leaves, pollen, embryos, cotyledons, hypocotyls, roots, root tips, anthers, flowers and a part thereof, ovules, shoots, stems, stalks, pith and capsules or callus or protoplasts derived therefrom.

A still further aspect, relates to a cured plant material—such as cured leaf or cured tobacco—derived or derivable from a mutant, non-naturally occurring or transgenic plant or cell, wherein expression of one or more of the polynucleotides described herein or the activity of the protein encoded thereby is reduced and wherein the conversion of nicotine to nornicotine is reduced, which results in reduced levels of NNN.

Suitably the visual appearance of said plant (for example, leaf) is substantially the same as the control plant. Suitably, the plant is a tobacco plant.

Embodiments are also directed to compositions and methods for producing mutant, non-naturally occurring or transgenic plants or plant cells that have been modified to modulate the expression or activity of the one or more of the polynucleotides or polypeptides described herein which can result in plants or plant components (for example, leaves—such as green leaves or cured leaves—or tobacco) or plant cells with modulated levels of nornicotine and/or at least NNN.

The mutant, non-naturally occurring or transgenic plants that are obtained according to the methods described herein may be similar or substantially the same in visual appearance to the control plants. In one embodiment, the leaf weight of the mutant, non-naturally occurring or transgenic plant is substantially the same as the control plant. In one embodiment, the leaf number of the mutant, non-naturally occurring or transgenic plant is substantially the same as the control plant. In one embodiment, the leaf weight and the leaf number of the mutant, non-naturally occurring or transgenic plant is substantially the same as the control plant. In one embodiment, the stalk height of the mutant, non-naturally occurring or transgenic plants is substantially the same as the control plants at, for example, one, two or three or more months after field transplant or 10, 20, 30 or 36 or more days after topping. For example, the stalk height of the mutant, non-naturally occurring or transgenic plants is not less than the stalk height of the control plants. In another embodiment, the chlorophyll content of the mutant, non-naturally occurring or transgenic plants is substantially the same as the control plants. In another embodiment, the stalk height of the mutant, non-naturally occurring or transgenic plants is substantially the same as the control plants and the chlorophyll content of the mutant, non-naturally occurring or transgenic plants is substantially the same as the control plants. In other embodiments, the size or form or number or colouration of the leaves of the mutant, non-naturally occurring or transgenic plants is substantially the same as the control plants. Suitably, the plant is a tobacco plant.

In another aspect, there is provided a method for modulating (eg. reducing) the amount of nornicotine and/or NNN in at least a part of a plant (for example, the leaves—such as cured leaves—or in tobacco), comprising the steps of: (i) modulating (eg. reducing) the expression or activity of an one or more of the polypeptides described herein (or any combination thereof as described herein), suitably, wherein the polypeptide(s) is encoded by the corresponding polynucleotide sequence described herein; (ii) measuring the nornicotine and/or NNN content in at least a part (for example, the leaves—such as cured leaves—or tobacco or in smoke) of the mutant, non-naturally occurring or transgenic plant obtained in step (i); and (iii) identifying a mutant, non-naturally occurring or transgenic plant in which the nornicotine and/or NNN content therein has been modulated (eg. reduced) in comparison to a control plant. Suitably, the visual appearance of said mutant, non-naturally occurring or transgenic plant is substantially the same as the control plant. Suitably, the plant is a tobacco plant.

In another aspect, there is provided a method for modulating (eg. reducing) the amount of nornicotine and/or NNN in at least a part of cured plant material—such as cured leaf—comprising the steps of: (i) modulating (eg. reducing) the expression or activity of an one or more of the polypeptides (or any combination thereof as described herein), suitably, wherein the polypeptide(s) is encoded by the corresponding polynucleotide sequence described herein; (ii) harvesting plant material—such as one or more of the leaves—and curing for a period of time; (iii) measuring the nornicotine and/or NNN content in at least a part of the cured plant material obtained in step (ii); and (iv) identifying cured plant material in which the nornicotine and/or NNN content therein has been modulated (eg. reduced) in comparison to a control plant.

An increase in expression as compared to the control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more, which includes an increase in transcriptional activity or polynucleotide expression or polypeptide expression or a combination thereof.

An increase in activity as compared to a control may be from about 5% to about 100%, or an increase of at least 10%, at least 20%, at least 25%, at least 30%, at least 40%, at least 50%, at least 60%, at least 70%, at least 75%, at least 80%, at least 90%, at least 95%, at least 98%, or 100% or more—such as 200% or 300% or more.

A reduction in expression as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%, which includes a reduction in transcriptional activity or polynucleotide expression or polypeptide expression or a combination thereof.

A reduction in activity as compared to a control may be from about 5% to about 100%, or a reduction of at least 10%, at least 20%, at least 25%, at least 30%, at least 40%, at least 50%, at least 60%, at least 70%, at least 75%, at least 80%, at least 90%, at least 95%, at least 98%, or 100%.

Polynucleotides and recombinant constructs described herein can be used to modulate the expression of the enzymes described herein in a plant species of interest, suitably tobacco.

A number of polynucleotide based methods can be used to increase gene expression in plants and plant cells. By way of example, a construct, vector or expression vector that is compatible with the plant to be transformed can be prepared which comprises the gene of interest together with an upstream promoter that is capable of overexpressing the gene in the plant or plant cell. Exemplary promoters are described herein. Following transformation and when grown under suitable conditions, the promoter can drive expression in order to modulate (for example, reduce) the levels of this enzyme in the plant, or in a specific tissue thereof. In one exemplary embodiment, a vector carrying one or more polynucleotides described herein (or any combination thereof as described herein) is generated to overexpress the gene in a plant or plant cell. The vector carries a suitable promoter—such as the cauliflower mosaic virus CaMV 35S promoter—upstream of the transgene driving its constitutive expression in all tissues of the plant. The vector also carries an antibiotic resistance gene in order to confer selection of the transformed calli and cell lines.

Various embodiments are therefore directed to methods for modulating (for example, reducing) the expression level of one or more polynucleotides described herein (or any combination thereof as described herein) by integrating multiple copies of the polynucleotide into a plant genome, comprising: transforming a plant cell host with an expression vector that comprises a promoter operably-linked to one or more polynucleotides described herein. The polypeptide encoded by a recombinant polynucleotide can be a native polypeptide, or can be heterologous to the cell.

A tobacco plant carrying a mutant allele of one or more polynucleotides described herein (or any combination thereof as described herein) can be used in a plant breeding program to create useful lines, varieties and hybrids. In particular, the mutant allele is introgressed into the commercially important varieties described above. Thus, methods for breeding plants are provided, that comprise crossing a mutant plant, a non-naturally occurring plant or a transgenic plant as described herein with a plant comprising a different genetic identity. The method may further comprise crossing the progeny plant with another plant, and optionally repeating the crossing until a progeny with the desirable genetic traits or genetic background is obtained. One purpose served by such breeding methods is to introduce a desirable genetic trait into other varieties, breeding lines, hybrids or cultivars, particularly those that are of commercial interest. Another purpose is to facilitate stacking of genetic modifications of different genes in a single plant variety, lines, hybrids or cultivars. Intraspecific as well as interspecific matings are contemplated. The progeny plants that arise from such crosses, also referred to as breeding lines, are examples of non-naturally occurring plants of the invention.

In one embodiment, a method is provided for producing a non-naturally occurring tobacco plant comprising: (a) crossing a mutant or transgenic tobacco plant with a second tobacco plant to yield progeny tobacco seed; (b) growing the progeny tobacco seed, under plant growth conditions, to yield the non-naturally occurring tobacco plant. The method may further comprises: (c) crossing the previous generation of non-naturally occurring tobacco plant with itself or another tobacco plant to yield progeny tobacco seed; (d) growing the progeny tobacco seed of step (c) under plant growth conditions, to yield additional non-naturally occurring tobacco plants; and (e) repeating the crossing and growing steps of (c) and (d) multiple times to generate further generations of non-naturally occurring tobacco plants. The method may optionally comprises prior to step (a), a step of providing a parent plant which comprises a genetic identity that is characterized and that is not identical to the mutant or transgenic plant. In some embodiments, depending on the breeding program, the crossing and growing steps are repeated from 0 to 2 times, from 0 to 3 times, from 0 to 4 times, 0 to 5 times, from 0 to 6 times, from 0 to 7 times, from 0 to 8 times, from 0 to 9 times or from 0 to 10 times, in order to generate generations of non-naturally occurring tobacco plants. Backcrossing is an example of such a method wherein a progeny is crossed with one of its parents or another plant genetically similar to its parent, in order to obtain a progeny plant in the next generation that has a genetic identity which is closer to that of one of the parents. Techniques for plant breeding, particularly tobacco plant breeding, are well known and can be used in the methods of the invention. The invention further provides non-naturally occurring tobacco plants produced by these methods. Certain embodiments exclude the step of selecting a plant.

In some embodiments of the methods described herein, lines resulting from breeding and screening for variant genes are evaluated in the field using standard field procedures. Control genotypes including the original unmutagenized parent are included and entries are arranged in the field in a randomized complete block design or other appropriate field design. For tobacco, standard agronomic practices are used, for example, the tobacco is harvested, weighed, and sampled for chemical and other common testing before and during curing. Statistical analyses of the data are performed to confirm the similarity of the selected lines to the parental line. Cytogenetic analyses of the selected plants are optionally performed to confirm the chromosome complement and chromosome pairing relationships.

DNA fingerprinting, single nucleotide polymorphism, microsatellite markers, or similar technologies may be used in a marker-assisted selection (MAS) breeding program to transfer or breed mutant alleles of a gene into other tobaccos, as described herein. For example, a breeder can create segregating populations from hybridizations of a genotype containing a mutant allele with an agronomically desirable genotype. Plants in the F2 or backcross generations can be screened using a marker developed from a genomic sequence or a fragment thereof, using one of the techniques listed herein. Plants identified as possessing the mutant allele can be backcrossed or self-pollinated to create a second population to be screened. Depending on the expected inheritance pattern or the MAS technology used, it may be necessary to self-pollinate the selected plants before each cycle of backcrossing to aid identification of the desired individual plants. Backcrossing or other breeding procedure can be repeated until the desired phenotype of the recurrent parent is recovered.

In a breeding program, successful crosses yield F1 plants that are fertile. Selected F1 plants can be crossed with one of the parents, and the first backcross generation plants are self-pollinated to produce a population that is again screened for variant gene expression (for example, the null version of the the gene). The process of backcrossing, self-pollination, and screening is repeated, for example, at least 4 times until the final screening produces a plant that is fertile and reasonably similar to the recurrent parent. This plant, if desired, is self-pollinated and the progeny are subsequently screened again to confirm that the plant exhibits variant gene expression. In some embodiments, a plant population in the F2 generation is screened for variant gene expression, for example, a plant is identified that fails to express a polypeptide due to the absence of the gene according to standard methods, for example, by using a PCR method with primers based upon the nucleotide sequence information for the polynucleotide(s) described herein (or any combination thereof as described herein).

Hybrid tobacco varieties can be produced by preventing self-pollination of female parent plants (that is, seed parents) of a first variety, permitting pollen from male parent plants of a second variety to fertilize the female parent plants, and allowing F1 hybrid seeds to form on the female plants. Self-pollination of female plants can be prevented by emasculating the flowers at an early stage of flower development. Alternatively, pollen formation can be prevented on the female parent plants using a form of male sterility. For example, male sterility can be produced by cytoplasmic male sterility (CMS), or transgenic male sterility wherein a transgene inhibits microsporogenesis and/or pollen formation, or self-incompatibility. Female parent plants containing CMS are particularly useful. In embodiments in which the female parent plants are CMS, pollen is harvested from male fertile plants and applied manually to the stigmas of CMS female parent plants, and the resulting F1 seed is harvested.

Varieties and lines described herein can be used to form single-cross tobacco F1 hybrids. In such embodiments, the plants of the parent varieties can be grown as substantially homogeneous adjoining populations to facilitate natural cross-pollination from the male parent plants to the female parent plants. The F1 seed formed on the female parent plants is selectively harvested by conventional means. One also can grow the two parent plant varieties in bulk and harvest a blend of F1 hybrid seed formed on the female parent and seed formed upon the male parent as the result of self-pollination. Alternatively, three-way crosses can be carried out wherein a single-cross F1 hybrid is used as a female parent and is crossed with a different male parent. As another alternative, double-cross hybrids can be created wherein the F1 progeny of two different single-crosses are themselves crossed.

A population of mutant, non-naturally occurring or transgenic plants can be screened or selected for those members of the population that have a desired trait or phenotype. For example, a population of progeny of a single transformation event can be screened for those plants having a desired level of expression or activity of the polypeptide(s) encoded thereby. Physical and biochemical methods can be used to identify expression or activity levels. These include Southern analysis or PCR amplification for detection of a polynucleotide; Northern blots, S1 RNase protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining and enzyme assays also can be used to detect the presence or expression or activity of polypeptides or polynucleotides.

Mutant, non-naturally occurring or transgenic plant cells and plants are described herein comprising one or more recombinant polynucleotides, one or more polynucleotide constructs, one or more double-stranded RNAs, one or more conjugates or one or more vectors/expression vectors.

Without limitation, the plants described herein may be modified for other purposes either before or after the expression or activity has been modulated according to the present invention. One or more of the following genetic modifications can be present in the mutant, non-naturally occurring or transgenic plants. In one embodiment, one or more genes that are involved in the conversion of nitrogenous metabolic intermediates is modified resulting in plants (such as leaves) that when cured, produces lower levels of at least one tobacco-specific nitrosamine than control plants. Non-limiting examples of genes that can be modified include, as described herein, genes encoding a nicotine demethylase, such as CYP82E4, CYP82E5 and CYP82E10 which participate in the conversion of nicotine to nornicotine and are described in WO2006091194, WO2008070274, WO2009064771 and PCT/US2011/021088 and as described in detail herein. In another embodiment, one or more genes that are involved in heavy metal uptake or heavy metal transport are modified resulting in plants or parts of plants (such as leaves) having a lower heavy metal content than control plants or parts thereof without the modification(s). Non-limiting examples include genes in the family of multidrug resistance associated proteins, the family of cation diffusion facilitators (CDF), the family of Zrt-, Irt-like proteins (ZIP), the family of cation exchangers (CAX), the family of copper transporters (COPT), the family of heavy-metal P-type ATPases (for example, HMAs, as described in WO2009074325), the family of homologs of natural resistance-associated macrophage proteins (NRAMP), and the family of ATP-binding cassette (ABC) transporters (for example, MRPs, as described in WO2012/028309, which participate in transport of heavy metals, such as cadmium. The term heavy metal as used herein includes transition metals. Examples of other modifications include herbicide tolerance, for example, glyphosate is an active ingredient of many broad spectrum herbicides. Glyphosate resistant transgenic plants have been developed by transferring the aroA gene (a glyphosate EPSP synthetase from *Salmonella typhimurium* and *E. coli*). Sulphonylurea resistant plants have been produced by transforming the mutant ALS (acetolactate synthetase) gene from *Arabidopsis*. OB protein of photosystem II from mutant *Amaranthus hybridus* has been transferred in to plants to produce atrazine resistant transgenic plants; and bromoxynil resistant transgenic plants have been produced by incorporating the bxn gene from the bacterium *Klebsiella pneumoniae*. Another exemplary modification results in plants that are resistant to insects. *Bacillus thuringiensis* (Bt) toxins can provide an effective way of delaying the emergence of Bt-resistant pests, as recently illustrated in broccoli where pyramided cry1Ac and cry1C Bt genes controlled diamondback moths resistant to either single protein and significantly delayed the evolution of resistant insects. Another exemplary modification results in plants that are resistant to diseases caused by pathogens (for example, viruses, bacteria, fungi). Plants expressing the Xa21 gene (resistance to bacterial blight) with plants expressing both a Bt fusion gene and a chitinase gene (resistance to yellow stem borer and tolerance to sheath) have been engineered. Another exemplary modification results in altered reproductive capability, such as male sterility. Another exemplary modification results in plants that are tolerant to abiotic stress (for example, drought, temperature, salinity), and tolerant transgenic plants have been produced by transferring acyl glycerol phosphate enzyme from *Arabidopsis*; genes coding mannitol dehydrogenase and sorbitol dehydrogenase which are involved in synthesis of mannitol and sorbitol improve drought resistance. Other exemplary modifications can result in plants with improved storage proteins and oils, plants with enhanced photosynthetic efficiency, plants with prolonged shelf life, plants with enhanced carbohydrate content, and plants resistant to fungi; plants encoding an enzyme involved in the biosynthesis of alkaloids. Transgenic plants in which the expression of S-adenosyl-L-methionine (SAM) and/or cystathionine gamma-synthase (CGS) has been modulated are also contemplated.

One or more such traits may be introgressed into the mutant, non-naturally occurring or transgenic tobacco plants from another tobacco cultivar or may be directly transformed into it. The introgression of the trait(s) into the mutant, non-naturally occurring or transgenic tobacco plants of the invention maybe achieved by any method of plant breeding known in the art, for example, pedigree breeding, backcrossing, doubled-haploid breeding, and the like (see, Wernsman, E. A, and Rufty, R. C. 1987. Chapter Seventeen. Tobacco. Pages 669-698 In: *Cultivar Development. Crop Species*. W. H. Fehr (ed.), MacMillan Publishing Co, Inc., New York, N.Y. 761 pp.). Molecular biology-based techniques described above, in particular RFLP and microsatellite markers, can be used in such backcrosses to identify the progenies having the highest degree of genetic identity with the recurrent parent. This permits one to accelerate the production of tobacco varieties having at least 90%, preferably at least 95%, more preferably at least 99% genetic identity with the recurrent parent, yet more preferably genetically identical to the recurrent parent, and further comprising the trait(s) introgressed from the donor parent. Such determination of genetic identity can be based on molecular markers known in the art.

The last backcross generation can be selfed to give pure breeding progeny for the nucleic acid(s) being transferred. The resulting plants generally have essentially all of the morphological and physiological characteristics of the mutant, non-naturally occurring or transgenic tobacco plants of the invention, in addition to the transferred trait(s) (for example, one or more single gene traits). The exact backcrossing protocol will depend on the trait being altered to determine an appropriate testing protocol. Although backcrossing methods are simplified when the trait being transferred is a dominant allele, a recessive allele may also be transferred. In this instance, it may be necessary to introduce a test of the progeny to determine if the desired trait has been successfully transferred.

Various embodiments provide mutant plants, non-naturally occurring plants or transgenic plants, as well as biomass in which the expression level of a polynucleotide (or any combination thereof as described herein) is modulated to modulate the nornicotine and/or NNN content therein.

Parts of such plants, particularly tobacco plants, and more particularly the leaf lamina and midrib of tobacco plants, can be incorporated into or used in making various consumable products including but not limited to aerosol forming materials, aerosol forming devices, smoking articles, smokable articles, smokeless products, and tobacco products. Examples of aerosol forming materials include but are not limited to tobacco compositions, tobaccos, tobacco extract, cut tobacco, cut filler, cured tobacco, expanded tobacco, homogenized tobacco, reconstituted tobacco, and pipe tobaccos. Smoking articles and smokable articles are types of aerosol forming devices. Examples of smoking articles or smokable articles include but are not limited to cigarettes, cigarillos, and cigars. Examples of smokeless products comprise chewing tobaccos, and snuffs. In certain aerosol forming devices, rather than combustion, a tobacco composition or another aerosol forming material is heated by one or more electrical heating elements to produce an aerosol. In another type of heated aerosol forming device, an aerosol is produced by the transfer of heat from a combustible fuel element or heat source to a physically separate aerosol forming material, which may be located within, around or downstream of the heat source. Smokeless tobacco products and various tobacco-containing aerosol forming materials may contain tobacco in any form, including as dried particles, shreds, granules, powders, or a slurry, deposited on, mixed in, surrounded by, or otherwise combined with other ingredients in any format, such as flakes, films, tabs, foams, or beads. As used herein, the term 'smoke' is used to describe a type of aerosol that is produced by smoking articles, such as cigarettes, or by combusting an aerosol forming material.

In one embodiment, there is also provided cured plant material from the mutant, transgenic and non-naturally occurring tobacco plants described herein. Processes of curing green tobacco leaves are known by those having skills in the art and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco-containing aerosol forming materials comprising plant material—such as leaves, preferably cured leaves—from the mutant tobacco plants, transgenic tobacco plants or non-naturally occurring tobacco plants described herein. The tobacco products described herein can be a blended tobacco product which may further comprise unmodified tobacco.

The amount of nornicotine in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The amount of NNN in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The amount of nicotine in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% higher—when compared to consumable products derived from non-mutant, non-naturally occurring or non-transgenic counterparts. The amount of nicotine in these smokable articles and smokeless products and aerosols thereof may be about the same as compared to consumable products derived from non-mutant, non-naturally occurring or non-transgenic counterparts.

The amount of total TSNAs in these smokable articles and smokeless products and aerosols thereof may be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, and 100% lower—such as about 200% or 300% lower—when compared to consumable products derived from non-mutant, non-naturally occurring or non-transgenic counterparts.

The mutant, non-naturally occurring or transgenic plants may have other uses in, for example, agriculture. For example, mutant, non-naturally occurring or transgenic plants described herein can be used to make animal feed and human food products.

The invention also provides methods for producing seeds comprising cultivating the mutant plant, non-naturally occurring plant, or transgenic plant described herein, and collecting seeds from the cultivated plants. Seeds from plants described herein can be conditioned and bagged in packaging material by means known in the art to form an article of manufacture. Packaging material such as paper and cloth are well known in the art. A package of seed can have a label, for example, a tag or label secured to the packaging material, a label printed on the package that describes the nature of the seeds therein.

Compositions, methods and kits for genotyping plants for identification, selection, or breeding can comprise a means of detecting the presence of a polynucleotide (or any combination thereof as described herein) in a sample of polynucleotide. Accordingly, a composition is described comprising one of more primers for specifically amplifying at least a portion of one or more of the polynucleotides and optionally one or more probes and optionally one or more reagents for conducting the amplification or detection.

Accordingly, gene specific oligonucleotide primers or probes comprising about 10 or more contiguous polynucleotides corresponding to the polynucleotide(s) described herein are disclosed. Said primers or probes may comprise or consist of about 15, 20, 25, 30, 40, 45 or 50 more contiguous polynucleotides that hybridise (for example, specifically hybridise) to the polynucleotide(s) described herein. In some embodiments, the primers or probes may comprise or consist of about 10 to 50 contiguous nucleotides, about 10 to 40 contiguous nucleotides, about 10 to 30 contiguous nucleotides or about 15 to 30 contiguous nucleotides that may be used in sequence-dependent methods of gene identification (for example, Southern hybridization) or isolation (for example, in situ hybridization of bacterial colonies or bacteriophage plaques) or gene detection (for example, as one or more amplification primers in nucleic acid amplification or detection). The one or more specific primers or probes can be designed and used to amplify or detect a part or all of the polynucleotide(s). By way of specific example, two primers may be used in a polymerase chain reaction protocol to amplify a nucleic acid fragment encoding a nucleic acid—such as DNA or RNA. The polymerase chain reaction may also be performed using one primer that is derived from a nucleic acid sequence and a second primer that hybridises to the sequence upstream or downstream of the nucleic acid sequence—such as a promoter sequence, the 3' end of the mRNA precursor or a sequence derived from a vector. Examples of thermal and isothermal techniques useful for in vitro amplification of polynucleotides are well known in the art. The sample may be or may be derived from a plant, a plant cell or plant material or a tobacco product made or derived from the plant, the plant cell or the plant material as described herein.

In a further aspect, there is also provided a method of detecting a polynucleotide(s) described herein (or any combination thereof as described herein) in a sample comprising the step of: (a) providing a sample comprising, or suspected of comprising, a polynucleotide; (b) contacting said sample with one of more primers or one or more probes for specifically detecting at least a portion of the polynucleotide(s); and (c) detecting the presence of an amplification product, wherein the presence of an amplification product is indicative of the presence of the polynucleotide(s) in the sample. In a further aspect, there is also provided the use of one of more primers or probes for specifically detecting at least a portion of the polynucleotide(s). Kits for detecting at least a portion of the polynucleotide(s) are also provided which comprise one of more primers or probes for specifically detecting at least a portion of the polynucleotide(s). The kit may comprise reagents for polynucleotide amplification—such as PCR—or reagents for probe hybridization-detection technology—such as Southern Blots, Northern Blots, in-situ hybridization, or microarray. The kit may comprise reagents for antibody binding-detection technology such as Western Blots, ELISAs, SELDI mass spectrometry or test strips. The kit may comprise reagents for DNA sequencing. The kit may comprise reagents and instructions for determining at least the NNN content and/or nicotine content and/or total TSNA content and/or nornicotine content. Suitably, the kit comprises reagents and instructions for determining at least NNN content and/or nictotine content and/or total TSNA content and/or nornicotine content in plant material, cured plant material or cured leaves.

In some embodiments, a kit may comprise instructions for one or more of the methods described. The kits described may be useful for genetic identity determination, phylogenetic studies, genotyping, haplotyping, pedigree analysis or plant breeding particularly with co-dominant scoring.

The present invention also provides a method of genotyping a plant, a plant cell or plant material comprising a polynucleotide as described herein. Genotyping provides a means of distinguishing homologs of a chromosome pair and can be used to differentiate segregants in a plant population. Molecular marker methods can be used for phylogenetic studies, characterizing genetic relationships among crop varieties, identifying crosses or somatic hybrids, localizing chromosomal segments affecting monogenic traits, map based cloning, and the study of quantitative inheritance. The specific method of genotyping may employ any number of molecular marker analytic techniques including amplification fragment length polymorphisms (AFLPs). AFLPs are the product of allelic differences between amplification fragments caused by nucleotide sequence variability. Thus, the present invention further provides a means to follow segregation of one or more genes or nucleic acids as well as chromosomal sequences genetically linked to these genes or nucleic acids using such techniques as AFLP analysis.

In one embodiment, there is also provided cured plant material from the mutant, transgenic and non-naturally occurring plants described herein. For example, processes of curing tobacco leaves are known by those having skills in the field and include without limitation air-curing, fire-curing, flue-curing and sun-curing. The process of curing green tobacco leaves depends on the type of tobacco harvested. For example, Virginia flue (bright) tobacco is typically flue-cured, Burley and certain dark strains are usually air-cured, and pipe tobacco, chewing tobacco, and snuff are usually fire-cured.

In another embodiment, there is described tobacco products including tobacco products comprising plant material—such as leaves, suitably cured plant material—such as cured leaves—from the mutant, transgenic and non-naturally occurring plants described herein or which are produced by the methods described herein. The tobacco products described herein may further comprise unmodified tobacco.

In another embodiment, there is described tobacco products comprising plant material, preferably leaves—such as cured leaves, from the mutant, transgenic and non-naturally occurring plants described herein. For example, the plant material may be added to the inside or outside of the tobacco product and so upon burning a desirable aroma is released. The tobacco product according to this embodiment may even be an unmodified tobacco or a modified tobacco. The tobacco product according to this embodiment may even be derived from a mutant, transgenic or non-naturally occurring plant which has modifications in one or more genes other than the genes disclosed herein.

The invention is further described in the Examples below, which are provided to describe the invention in further detail. These examples, which set forth a preferred mode presently contemplated for carrying out the invention, are intended to illustrate and not to limit the invention.

EXAMPLES

Example 1

Analysis of NND3 Expression Levels

To determine the function of NND3 and its role in nicotine conversion, the expression of NND3 is analyzed. For this purpose, different tissues of greenhouse grown *N. tabacum* var. TN90 are harvested and analysed via quantitative PCR.

RNA extraction is performed using the RNeasy Mini kit (Qiagen) according to the manufacturer's instructions. RNA samples are diluted in water to obtain 1 μg RNA in 10 μl final volume. Then DNase digestion is performed with RQ1 RNase-Free DNase (Promega). The DNase reaction is stopped using RQ1 DNase stop solution (Promega). Immediately, the reverse transcriptase (RT) reaction is performed to convert RNA into complementary DNA (cDNA). For RT reactions, M-MLV Reverse Transcriptase, RNase H Minus, Point Mutant (Promega) was used in combination with oligo(dT)15 primers.

Quantitative real-time PCR is performed using the Stratagene Mx3005P and the corresponding software. For each target, different primer pairs are designed according to the guidelines of the Mx3005P user handbook. The primer pairs are tested for primer dimer formation and their performance in a qPCR run. Their efficiency is tested using a standard curve with a five-fold dilution of cDNA. The PCR products are sequenced in order to verify that the primers specifically amplify their target sequence. As the different CYP82E genes are close in sequence, primer design is complex and the chosen primers do not always show optimal efficiency.

The dicrepancies in efficiency mean that the qPCR experiment values are gene specific and do not represent an absolute expression value. Therefore, the comparison in expression values is valid for each gene between the various tissues but not between genes. Employed primer pairs and their efficiency are listed in Table 1. ABsolute Blue QPCR SYBR Green low ROX Mix (Thermo Scientific) is used with primer concentrations of 300 nM. In a qPCR run a denaturation temperature of 95° C. is employed, initially for 15 minutes and then in each cycle for 15 seconds, 15 seconds at 60° C. for annealing and 25 seconds at 72° C. for elongation, for 50 cycles. All samples are run in triplicates. Furthermore, biological triplicates are employed. The expression of the actin9 gene (house-keeping gene) is used for all samples as normaliser.

The results are shown in FIG. 1 and confirm the expression of CYP82E5 and CYP82E10 in green leaves. These genes are also highly expressed in all other tissues that were tested. They show similar a very similar expression pattern. Whilst CYP82E4 and NND3 each show expression in flowers and roots, NND3 is not expressed at detectable levels in leaves whereas CYP82E4 shows expression exclusively in senescent leaves. For primer specificity verification, the PCR products have been purified and sequenced. The low signal observed for NND3 in roots contained mixed products of NND3 and CYP82E4 whereas products from flower material contained NND3 only.

Example 2

Demonstration that NND3 Encodes for a Functional Nicotine Demethylase

Although the predicted protein sequence presents a high level of homology to known demethylases such as CYP82E4, CYP82E5 and CYP82E10, its function cannot be inferred from homology a since it has been shown in the cytochrome P450 family that a few aminoacids difference is enough to change or alleviate substrate specificity.

The function of NND3 is confirmed by overexpression in tobacco. For this purpose, an overexpression construct was designed with the NND3 coding sequence (SEQ ID NO:1) to be constitutively expressed under the control of the MMV promoter in an ultra-low converter burley plant background lacking functional CYP82E4, CYP82E5 and CYP82E10 genes.

Figure 2:
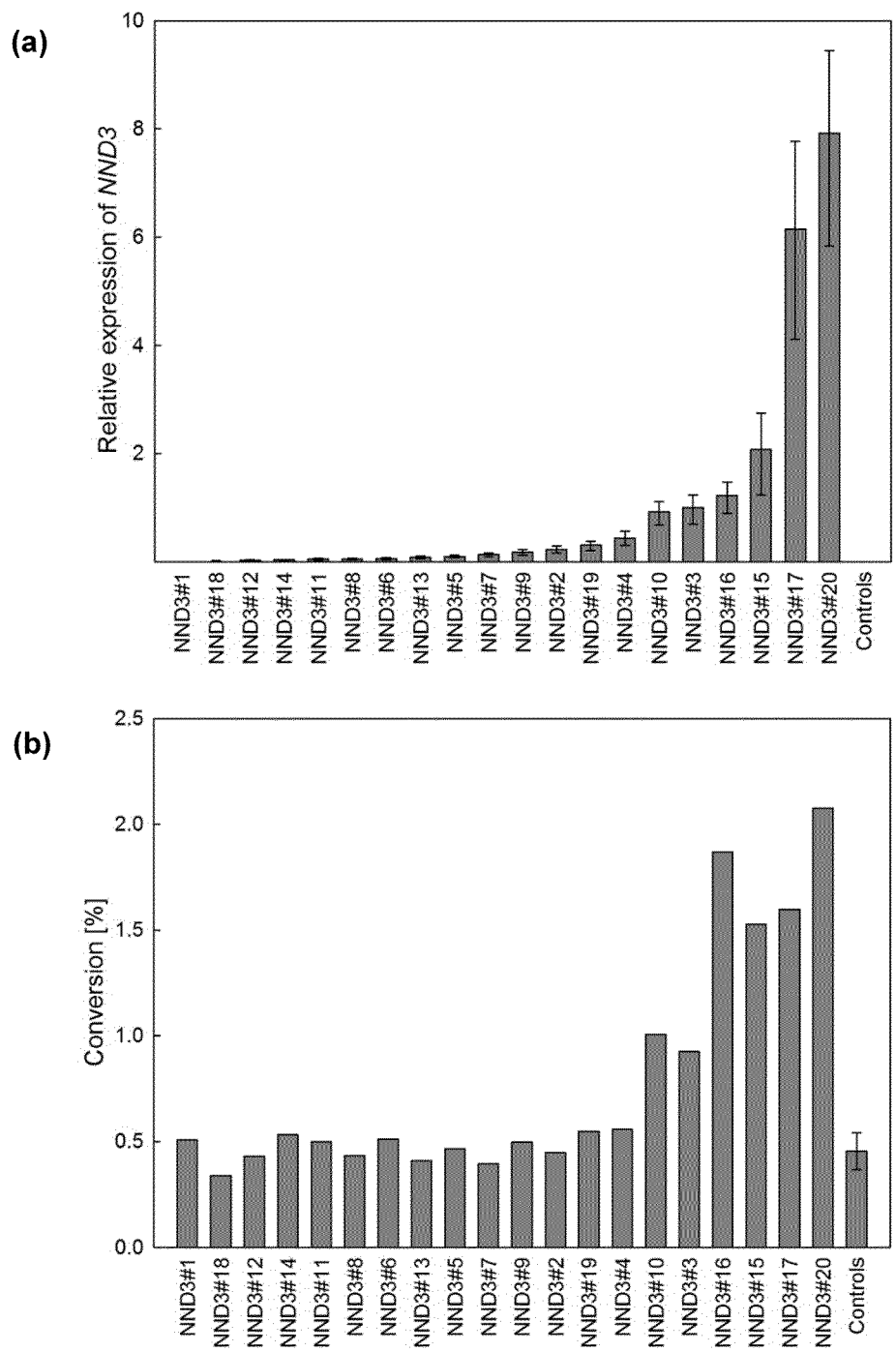
FIG. 2 shows relative NND3 expression (A) and nicotine to nornicotine conversion levels (B) measured in leaves of individual mature $T_0$ plants transformed with NND3 coding sequence under a strong constitutive promoter in the ultra-low converter TN90 cyp82e4/cyp82e5/cyp82e10 background.

Twenty independent transgenic lines were generated. The primary transformants (To) were transferred to soil and leaves of mature plants were analysed for NND3 expression using primers NND3_F6 and NND3_R7 (FIG. 2A) as well as for nicotine and nornicotine levels (FIG. 2B). Five control lines were analysed for which bar and error represent mean and standard deviation.

Expression analysis was conducted in three technical replicates. Bars and errors indicate mean and deviation in the replicates (calculated by MxPro software, Stratagene).

Expression data confirms that NND3 is not expressed in TN90 green leaves since no signal could be detected. NND3 expression levels measured in the different $T_0$ plants were therefore expressed relative to NND3#3 plant which was randomly chosen. A significant variation is observed in expression of different plants. This result is expected when surveying transgene expression in a $T_0$ population because each plant is the result of an independent transformation event. As a consequence expression levels can vary greatly from plant to plant depending on either the transgene copy number or adequate insertion of the transgene.

Same leaf samples were analysed in a single measurement for nicotine and nornicotine.

Nicotine and nornicotine content of the samples was analyzed by HILIC-UPLC-UV/MS. Nornicotine was quantified with MS detection (pos. ESI; MRM mode; internal standard: nornicotine-d4); for nicotine UV detection at 260 nm was used. Conversion was calculated as [nornicotine]/([nornicotine]+[nicotine])×100.

Six of the transgenic lines that showed highest NND3 expression (#10, #3, #16, #15, #17, and #20) exhibited elevated nicotine conversion. Nicotine conversion is 0.5% in TN90 cyp82e4/cyp82e5/cyp82e10 plants, and is increased up to fourfold in MMV:NND3 high expressing lines. Consistently a low level of conversion indistinguishable from the control plant level is observed in the plants showing the lowest expression of the transgene.

These data clearly demonstrate that the newly identified NND3 gene encodes a functional nicotine N-demethylase.

TABLE 1

Primers used for expression analysis of NND3 and related functional CYP82E genes.

| Primer name | Target gene | Sequence (5'-3') | Efficiency (%) |
|---|---|---|---|
| NND3_F1 | NND3 | TTGATCCAGGGTTTCAATTAC AGC (SEQ ID NO: 36) | 102.7 |
| NND3_R2 | NND3 | AACGTACCAAATTAGAAAAC GTGTACC (SEQ ID NO: 37) | |
| E4_F1 | CYP82E4 | TTTTCAGAATTGGTTAGAGGA ACATATTAAT (SEQ ID NO: 38) | 80.7 |
| E4_R1 | CYP82E4 | TGTGTCTATCTCTTCTTGTGC TTTCG (SEQ ID NO: 39) | |
| E5_F1 | CYP82E5 | AGAGATTCTTCGCTGATGATA TTGACTAC (SEQ ID NO: 40) | 101.3 |
| E5_R1 | CYP82E5 | CCGTAATTGTCACTTCTACAG GATTTACT (SEQ ID NO: 41) | |
| E10_F2 | CYP82E10 | GCTGATATTGACTTTCGTGGT CAA (SEQ ID NO: 42) | 87.3 |
| E10_R2 | CYP82E10 | GCGAGGCGTAATTACCACTTC TAT (SEQ ID NO: 43) | |
| P00014_F | Actin9 | CTATTCTCCGCTTTGGACTTG GCA (SEQ ID NO: 44) | |
| P00014_R | Actin9 | AGGACCTCAGGACAACGGAAA CG (SEQ ID NO: 45) | |
| NND3_F6 | NND3 | AATTTTGGTCTCATCGTGAAG ATGATA (SEQ ID NO: 46) | |
| NND3_R7 | NND3 | TCACTCTCTTCTACCCATCTA TCCTTG (SEQ ID NO: 47) | |

Example 3

Demonstration that NND3 Silencing Leads to Reduced Nicotine Conversion

A silencing construct is designed that is expressed constitutively under the control of the MMV promoter in an ultra-low converter burley plant background lacking functional CYP82E4, CYP82E5 and CYP82E10 genes. For the silencing construct, a 100 bp sequence is used in forward and reverse direction, separated by an intron sequence (SEQ ID NO: 4). Results indicate that silencing of NND3 in flowers leads to reduced nicotine conversion demonstrating that the NND3 enzyme is not only functional, but also contributes to nicotine conversion in the plant.

Example 4

Figure 3:
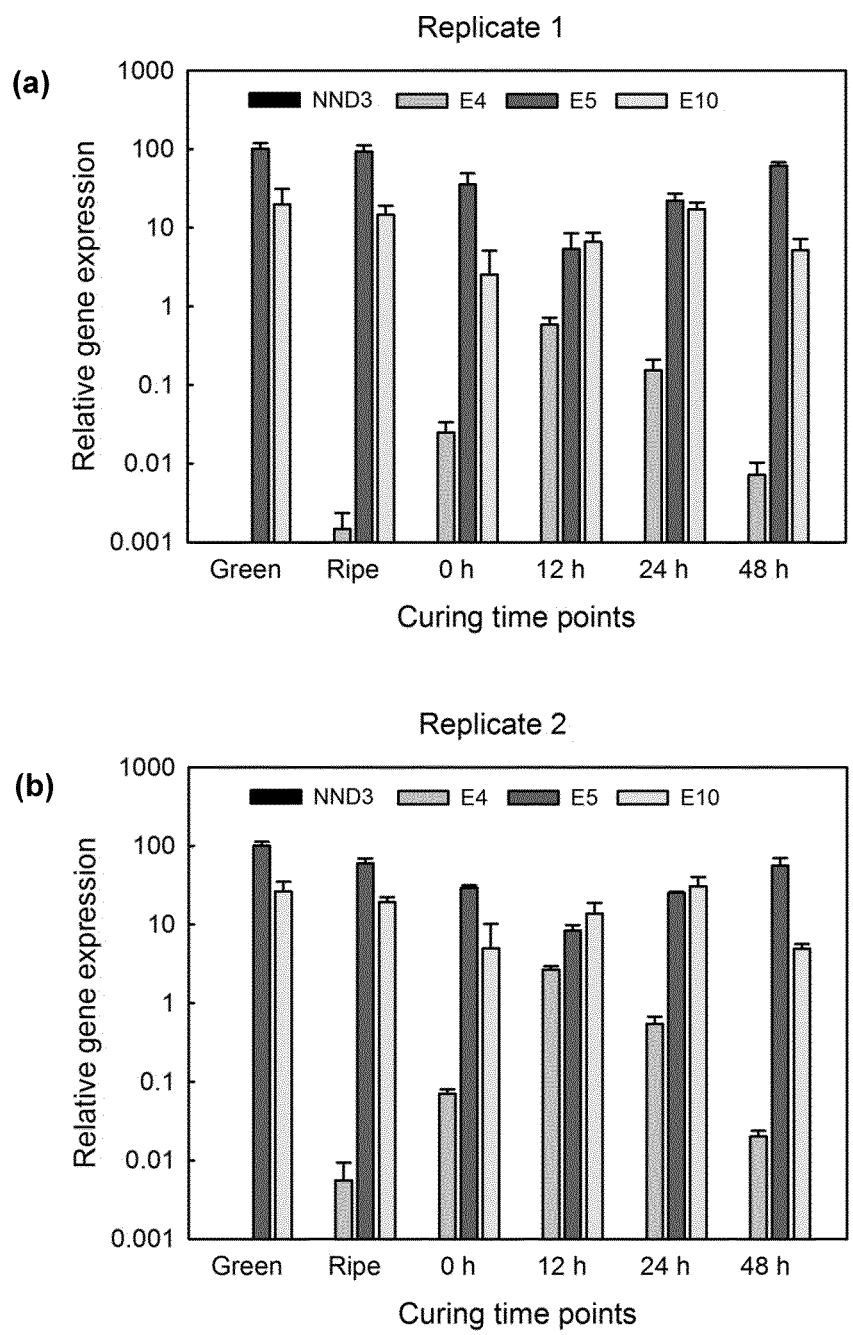
FIG. 3 shows relative expression levels of NND3 and related functional CYP82E genes in *N. tabacum* var. Stella leaves at different curing time points. Samples are taken from pools of several leaves. Two pools are analyzed as biological replicates—(a) replicate 1 and (b) replicate 2. Bars indicate mean±SD of three technical replicates.

Relative Expression Levels of NND3 in *N. tabacum* Var. Stella Leaves at Different Curing Time Points Relative expression levels of NND3 and related functional CYP82E genes in *N. tabacum* var. Stella leaves at different curing time points is analysed. Samples are taken in "green" leaves (upper stalk position) and in "ripe" leaves (lower stalk position) at harvest time. The leaves are transported to an air curing barn and a sample is taken when curing starts ("0 h") and then again after 12 hours ("12 h"), 24 hours ("24 h") and 48 hours ("48 h"). Samples are taken from pools of several leaves. Two pools are analyzed as biological replicates—replicate 1 (FIG. 3a) and 2 (FIG. 3b). The results are shown in FIG. 3. Bars indicate mean±SD of three technical replicates. Expression levels of the different CYP82E genes can only be considered independently and not by direct comparison due to different PCR efficiencies. CYP82E5 and CYP82E10 are expressed to a similar extent in all leaf samples. Expression of CYP82E4 is activated in senescent leaves and increases under curing conditions. NND3 is not expressed in leaves under all conditions analyzed.

Any publication cited or described herein provides relevant information disclosed prior to the filing date of the present application. Statements herein are not to be construed as an admission that the inventors are not entitled to antedate such disclosures. All publications mentioned in the above specification are herein incorporated by reference. Various modifications and variations of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in cellular, molecular and plant biology or related fields are intended to be within the scope of the following claims.

SEQUENCES (Polynucleotide equence of the *N. tabacum* TN90 NND3-T gene. The intron is indicated in lower-case characters, the coding sequence is underlined. Start and stop codon are highlighted in grey.)

SEQ ID NO: 1

ATGGTTTTTCCCATAGAAGCCATTGTAGGACTAGTAACCTTCACATTTCTCTTCTACTTCCTATGGACAAAAAAATCTCAAAAACC

TTCAAAACCCTTACCACCGAAAATCCCCGGAGGATGGCCGGTAATTGGCCATCTTTTCCACTTCAATGACGACGGCAACGACCGTC

-continued

CATTAGCTCGAAAACTCGGAGACTTAGCTGACAAATACGGCCCCGTTTTCACTTTTCGGCTAGGCCTTCCCCTTGTGTTAGTTGTA

AGCAGTTACGAAGCTATAAAAGACTGTTTCTCTACAAATGATGCCATTTTCTCTAATCGTCCAGCTTTTCTTTACGGCAATACCT

TGGCTACAATAATGCCATGCTATTTTTGGCAAATTACGGACCTTACTGGCGAAAAAATCGTAAATTAGTTATTCAGGAAGTTCTCT

CAGCTAGTCGTCTCAAAAAATTCAAACACGTGAGATTCGCCAGAATTCAAACGAGCATTAAGAATTTATACACTCGAATTGATAGA

AATTCGAGTACGATAAATTTAACTGATTGGTTAGAAGAATTGAATTTTGGTCTCATCGTGAAGATGATAGCTGGGAAAAATTATGA

ATCCGGTAAAGGAGATGAACAAGTGGAGAGATTTAAGAAAGCGTTTAAGGATTTTATGATTATATCAATGGAGTTTGTGTTATGGG

ATGCATTTCCAATTCCATTATTTAAATGGGTGGATTTTCAAGGGCATGTTAAGGCTATGAAAAGGACATTTAAGGATATAGATTCT

GTTTTTCAGAATTGGTTAGAGGAACATATTAACAAAAGAGAAAAAATGGAGGTTAATGCAGAAGGGAATGAACAAGATTTCATTGA

TGTGGTGCTTTCAAAAATGAGTAATGAATATCTTGGTGAAGGTTACTCTCGTGATACTGTCATAAAAGCAACAGTTTTTgtaagtt catctgtcactcccgaattctgcttgaatgcagacaccgagttgccttttattagactatctaaatattaaggatgattatatat agcaaaaatatagtaggatttctcgggctttgggatagaagaatattcatcattatataacttttgatggtaaaagatgagatcta acctcttataattgcccaaccacgttgatatatagaacaaaaccttttttactcccattgagcataacgaaaatgaaagcaaaggga cttcttctcttttttaggaaaaaaatctttgattgcttgttgaatatacattcatgttttctttttctatttctaataataatgg tgcttgaatcaggttgcgtgcctcgtgacttttgagaaaaaaaaacaaattcattagtataatgaggtgtgcatacttgacaacta ctatactaactagaacaaggttcggcagataatgacgctaacctacttttatattgaattatcatttgtatttaactgtattctat tttgtccacagAGTTTGGTCTTGGATGCTGCGGACACAGTTGCTCTTCACATAAATTGGGGTATGGCATTACTGATCAACAATCAA AATGCCTTGAAGAAAGCACAAGAAGAGATAGACACAAAAGTTGGCAAGGATAGATGGGTAGAAGAGAGTGATATTAAGGATTTGGT GTACCTCCAAGCTATTGTTAAAGAAGTGTTACGATTATATCCACCGGGACCTTTGTTAGTACCACATGAAAATATAGAGGATTGTG TTGTTAGTGGATATTACATTTCTAAAGGGACTAGACTATTCGCAAATGTTATGAAACTGCAGCGCGATCCTAAACTCTGGCCAAAT CCTGATAATTTCGATCCAGAGAGATTTGTCGCTGCAGGTATTGACTTTCGTGGTCAGCATTATGAGTATATCCCGTTTGGTTCTGG AAGACGATCTTGTCCGGGGATGACTTATGCATTGCAAGTGGAACACTTAACAATGGCACATTTGATCCAGGGTTTCAATTACAGCA CTCCAAATGACGAGCCCTTGGATATGAAGGAAGGTGCAGGTATAACTATACGTAAGGTAAATCCCGTGGAAGTGATAATTATGCCT

CGCCTGGCACCTGAGCTTTATTAA (Polynucleotide coding sequence of NND3 used in the overexpression
construct under the control of the MMV promoter).

SEQ ID NO: 2

ATGGTTTTTCCCATAGAAGCCATTGTAGGACTAGTAACCTTCACATTTCTCTTCTACTTCCTATGGACAAAAAAATCTCAAAAACC

TTCAAAACCCTTACCACCGAAAATCCCCGGAGGATGGCCGGTAATTGGCCATCTTTTCCACTTCAATGACGACGGCAACGACCGTC

CATTAGCTCGAAAACTCGGAGACTTAGCTGACAAATACGGCCCCGTTTTCACTTTTCGGCTAGGCCTTCCCCTTGTGTTAGTTGTA

AGCAGTTACGAAGCTATAAAAGACTGTTTCTCTACAAATGATGCCATTTTCTCTAATCGTCCAGCTTTTCTTTACGGCAATACCT

TGGCTACAATAATGCCATGCTATTTTTGGCAAATTACGGACCTTACTGGCGAAAAAATCGTAAATTAGTTATTCAGGAAGTTCTCT

CAGCTAGTCGTCTCAAAAAATTCAAACACGTGAGATTCGCCAGAATTCAAACGAGCATTAAGAATTTATACACTCGAATTGATAGA

AATTCGAGTACGATAAATTTAACTGATTGGTTAGAAGAATTGAATTTTGGTCTCATCGTGAAGATGATAGCTGGGAAAAATTATGA

ATCCGGTAAAGGAGATGAACAAGTGGAGAGATTTAAGAAAGCGTTTAAGGATTTTATGATTATATCAATGGAGTTTGTGTTATGGG

ATGCATTTCCAATTCCATTATTTAAATGGGTGGATTTTCAAGGGCATGTTAAGGCTATGAAAAGGACATTTAAGGATATAGATTCT

GTTTTTCAGAATTGGTTAGAGGAACATATTAACAAAAGAGAAAAAATGGAGGTTAATGCAGAAGGGAATGAACAAGATTTCATTGA

TGTGGTGCTTTCAAAAATGAGTAATGAATATCTTGGTGAAGGTTACTCTCGTGATACTGTCATAAAAGCAACAGTTTTTAGTTTGG

TCTTGGATGCTGCGGACACAGTTGCTCTTCACATAAATTGGGGTATGGCATTACTGATCAACAATCAAATGCCTTGAAGAAAGCA

CAAGAAGAGATAGACACAAAAGTTGGCAAGGATAGATGGGTAGAAGAGAGTGATATTAAGGATTTGGTGTACCTCCAAGCTATTGT

TAAAGAAGTGTTACGATTATATCCACCGGGACCTTTGTTAGTACCACATGAAAATATAGAGGATTGTGTTGTTAGTGGATATTACA

TTTCTAAAGGGACTAGACTATTCGCAAATGTTATGAAACTGCAGCGCGATCCTAAACTCTGGCCAAATCCTGATAATTTCGATCCA

GAGAGATTTGTCGCTGCAGGTATTGACTTTCGTGGTCAGCATTATGAGTATATCCCGTTTGGTTCTGGAAGACGATCTTGTCCGGG

-continued

```
GATGACTTATGCATTGCAAGTGGAACACTTAACAATGGCACATTTGATCCAGGGTTTCAATTACAGCACTCCAAATGACGAGCCCT

TGGATATGAAGGAAGGTGCAGGTATAACTATACGTAAGGTAAATCCCGTGGAAGTGATAATTATGCCTCGCCTGGCACCTGAGCTT

TATTAA
```

(Polypeptide sequence of the *N. tabacum* TN90 NND3 protein sequence)

SEQ ID NO: 3

```
MVFPIEAIVGLVTFTFLFYFLWTKKSQKPSKPLPPKIPGGWPVIGHLFHFNDDGNDRPLARKLGDLADKYGPVFTFRLGLPLVLVV

SSYEAIKDCFSTNDAIFSNRPAFLYGEYLGYNNAMLFLANYGPYWRKNRKLVIQEVLSASRLKKFKHVRFARIQTSIKNLYTRIDR

NSSTINLTDWLEELNFGLIVKMIAGKNYESGKGDEQVERFKKAFKDFMIISMEFVLWDAFPIPLFKWVDFQGHVKAMKRTFKDIDS

VFQNWLEEHINKREKMEVNAEGNEQDFIDVVLSKMSNEYLGEGYSRDTVIKATVFSLVLDAADTVALHINWGMALLINNQNALKKA

QEEIDTKVGKDRWVEESDIKDLVYLQAIVKEVLRLYPPGPLLVPHENIEDCVVSGYYISKGTRLFANVMKLQRDPKLWPNPDNFDP

ERFVAAGIDFRGQHYEYIPFGSGRRSCPGMTYALQVEHLTMAHLIQGFNYSTPNDEPLDMKEGAGITIRKVNPVEVIIMPRLAPEL

Y
```

(Polynucleotide sequence an RNAi construct using a 100 bp unique sequence of NND3 in forward and reverse direction separated by an intron sequence found in the IPMS2 gene. The intron sequence is indicated in lower-case characters).

SEQ ID NO: 4

<u>GCGATCCTAAACTCTGGCCAAATCCTGATAATTTCGATCCAGAGAGATTTGTCGCTGCAGGTATTGACTTTCGTGGT</u>

<u>CAGCATTATGAGTATATCCCGTT</u>tggtaacctttaatgtttaaccgttcacatttctaatatttacttatttgtaac atgtcgtcacgtgttagtttcattcttttttatgaaccaaacatgcatgcaaagatatttttagatatttggacggcg agtgagatttgaaactaggaccgtttgcctgatacaatattaaaatatgtaaccattttatgtacaagtttaaactg ttgatagtagcatatttttacttttatttaagtatactatattccaacaggtaagttaac<u>AACGGGATATACTCAT</u>

<u>AATGCTGACCACGAAAGTCAATACCTGCAGCGACAAATCTCTCTGGATCGAAATTATCAGGATTTGGCCAGAGTTTA</u>

<u>GGATCGC</u>

(Protein sequence of CYP82E4 nicotine demethylase)

SEQ ID NO: 5

```
Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
             20                  25                  30

Leu Pro Pro Lys Ile Pro Gly Gly Trp Pro Val Ile Gly His Leu Phe
         35                  40                  45

His Phe Asn Asp Asp Gly Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205
```

```
Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Arg Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

(Protein sequence of P38L variant CYP82E4 nicotine demethylase)                    SEQ ID NO: 6

Met Leu Ser Pro Ile Glu Ala Ile Val Gly Leu Val Thr Phe Thr Phe
  1                 5                  10                  15

Leu Phe Phe Phe Leu Trp Thr Lys Lys Ser Gln Lys Pro Ser Lys Pro
                 20                  25                  30

Leu Pro Pro Lys Ile Leu Gly Gly Trp Pro Val Ile Gly His Leu Phe
             35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                 85                  90                  95
```

-continued

Ser Thr Asn Asp Ala Ile Phe Ser Asn Arg Pro Ala Phe Leu Tyr Gly
             100                 105                 110

Asp Tyr Leu Gly Tyr Asn Asn Ala Met Leu Phe Leu Ala Asn Tyr Gly
         115                 120                 125

Pro Tyr Trp Arg Lys Asn Arg Lys Leu Val Ile Gln Glu Val Leu Ser
         130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                 165                 170                 175

Ile Asn Leu Thr Asp Trp Leu Glu Glu Leu Asn Phe Gly Leu Ile Val
             180                 185                 190

Lys Met Ile Ala Gly Lys Asn Tyr Glu Ser Gly Lys Gly Asp Glu Gln
         195                 200                 205

Val Glu Arg Phe Lys Lys Ala Phe Lys Asp Phe Met Ile Leu Ser Met
         210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                 245                 250                 255

Asp Ser Val Phe Gln Asn Trp Leu Glu Glu His Ile Asn Lys Arg Glu
             260                 265                 270

Lys Met Glu Val Asn Ala Glu Gly Asn Glu Gln Asp Phe Ile Asp Val
         275                 280                 285

Val Leu Ser Lys Met Ser Asn Glu Tyr Leu Gly Glu Gly Tyr Ser Arg
         290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                 325                 330                 335

Asn Gln Lys Ala Leu Thr Lys Ala Gln Glu Glu Ile Asp Thr Lys Val
             340                 345                 350

Gly Lys Asp Arg Trp Val Glu Glu Ser Asp Ile Lys Asp Leu Val Tyr
         355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                 405                 410                 415

Arg Asp Pro Lys Leu Trp Ser Asp Pro Asp Thr Phe Asp Pro Glu Arg
             420                 425                 430

Phe Ile Ala Thr Asp Ile Asp Phe Arg Gly Gln Tyr Tyr Lys Tyr Ile
         435                 440                 445

Pro Phe Gly Ser Gly Arg Arg Ser Cys Pro Gly Met Thr Tyr Ala Leu
         450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                 485                 490                 495

Thr Ile Arg Lys Val Asn Pro Val Glu Leu Ile Ile Ala Pro Arg Leu
             500                 505                 510

Ala Pro Glu Leu Tyr
         515

-continued (Protein sequence of D171N variant CYP82E4 nicotine demethylase)

SEQ ID NO: 7

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asn Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg

```
                        420                 425                 430
Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
515

(Protein sequence of E201K variant CYP82E4 nicotine demethylase)     SEQ ID NO: 8

Met Leu Ser Pro Ile Glu Ala Ile Val Gly Leu Val Thr Phe Thr Phe
  1               5                  10                  15

Leu Phe Phe Phe Leu Trp Thr Lys Ser Gln Lys Pro Ser Lys Pro
                 20                  25                  30

Leu Pro Pro Lys Ile Pro Gly Gly Trp Pro Val Ile Gly His Leu Phe
                 35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
65                   70                  75                  80

Pro Leu Val Leu Val Val Ser Tyr Glu Ala Val Lys Asp Cys Phe
                 85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Lys Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320
```

-continued

```
Asp Thr Val Ala Leu His Ile Asn Trp Gly Met Ala Leu Leu Ile Asn
            325                 330                 335

Asn Gln Lys Ala Leu Thr Lys Ala Gln Glu Ile Asp Thr Lys Val
        340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
        420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
        500                 505                 510

Ala Pro Glu Leu Tyr
        515

(Protein sequence of R169Q variant CYP82E4 nicotine demethylase)                        SEQ ID NO: 9

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
        100                 105                 110

Asp Tyr Leu Gly Tyr Asn Asn Ala Met Leu Phe Leu Ala Asn Tyr Gly
    115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Gln Ile Asp Gly Asn Ser Ser Thr
            165                 170                 175

Ile Asn Leu Thr Asp Trp Leu Glu Glu Leu Asn Phe Gly Leu Ile Val
        180                 185                 190

Lys Met Ile Ala Gly Lys Asn Tyr Glu Ser Gly Lys Gly Asp Glu Gln
        195                 200                 205
```

-continued

```
Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
            325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
        515

(Protein sequence of G459R variant CYP82E4 nicotine demethylase)
                                                                    SEQ ID NO: 10
Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
```

-continued

```
                    100                 105                 110
Asp Tyr Leu Gly Tyr Asn Asn Ala Met Leu Phe Leu Ala Asn Tyr Gly
                115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Arg Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515
```

-continued (Protein sequence of T427I variant CYP82E4 nicotine demethylase)

SEQ ID NO: 11

```
Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
             100                 105                 110

Asp Tyr Leu Gly Tyr Asn Asn Ala Met Leu Phe Leu Ala Asn Tyr Gly
             115                 120                 125

Pro Tyr Trp Arg Lys Asn Arg Lys Leu Val Ile Gln Glu Val Leu Ser
 130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
             180                 185                 190

Lys Met Ile Ala Gly Lys Asn Tyr Glu Ser Gly Lys Gly Asp Glu Gln
             195                 200                 205

Val Glu Arg Phe Lys Lys Ala Phe Lys Asp Phe Met Ile Leu Ser Met
 210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
             260                 265                 270

Lys Met Glu Val Asn Ala Glu Gly Asn Glu Gln Asp Phe Ile Asp Val
             275                 280                 285

Val Leu Ser Lys Met Ser Asn Glu Tyr Leu Gly Glu Gly Tyr Ser Arg
 290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
             340                 345                 350

Gly Lys Asp Arg Trp Val Glu Glu Ser Asp Ile Lys Asp Leu Val Tyr
             355                 360                 365

Leu Gln Ala Ile Val Lys Glu Val Leu Arg Leu Tyr Pro Pro Gly Pro
 370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415
```

```
Arg Asp Pro Lys Leu Trp Ser Asp Pro Asp Ile Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ala Pro Arg Leu
            500                 505                 510

Ala Pro Glu Leu Tyr
            515
```

(Protein sequence of V376M variant CYP82E4 nicotine demethylase) SEQ ID NO: 12

```
Met Leu Ser Pro Ile Glu Ala Ile Val Gly Leu Val Thr Phe Thr Phe
  1               5                  10                  15

Leu Phe Phe Phe Leu Trp Thr Lys Lys Ser Gln Lys Pro Ser Lys Pro
             20                  25                  30

Leu Pro Pro Lys Ile Pro Gly Gly Trp Pro Val Ile Gly His Leu Phe
             35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
```

-continued

```
            305                 310                 315                 320
Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Ser Asp Ile Lys Asp Leu Val Tyr
            355                 360                 365

Leu Gln Ala Ile Val Lys Glu Met Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515
```

(Protein sequence of W329Stop variant CYP82E4 nicotine demethylase)

SEQ ID NO: 13

```
Met Leu Ser Pro Ile Glu Ala Ile Val Gly Leu Val Thr Phe Thr Phe
 1               5                  10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205
```

```
Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                    245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn
                325
```

(Protein sequence of K364N variant CYP82E4 nicotine demethylase)

SEQ ID NO: 14

```
Met Leu Ser Pro Ile Glu Ala Ile Val Gly Leu Val Thr Phe Thr Phe
 1                5                  10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285
```

-continued

```
Val Leu Ser Lys Met Ser Asn Glu Tyr Leu Gly Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
                340                 345                 350

Gly Lys Asp Arg Trp Val Glu Glu Ser Asp Ile Asn Asp Leu Val Tyr
                355                 360                 365

Leu Gln Ala Ile Val Lys Glu Val Leu Arg Leu Tyr Pro Pro Gly Pro
                370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
                450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515
```

(Protein sequence of P382S variant CYP82E4 nicotine demethylase)  SEQ ID NO: 15

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
```

-continued

```
                180                 185                 190
Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Ser Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515
```

(Protein sequence of P458S variant CYP82E4 nicotine demethylase)

SEQ ID NO: 16

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80
```

```
Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Ser Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510
```

```
Ala Pro Glu Leu Tyr
        515
```

(Protein sequence of CYP82E5 nicotine demethylase)  SEQ ID NO: 17

```
Met Val Ser Pro Val Glu Ala Ile Val Gly Leu Val Thr Leu Thr Leu
 1               5                  10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65              70                  75                  80

Pro Leu Val Leu Val Val Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400
```

```
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
                420                 425                 430
Phe Phe Ala Asp Asp Ile Asp Tyr Arg Gly Gln His Tyr Glu Phe Ile
                435                 440                 445
Pro Phe Gly Ser Gly Arg Arg Ser Cys Pro Gly Met Thr Tyr Ala Leu
                450                 455                 460
Gln Ala Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Val Glu Val Thr Ile Thr Ala Arg Leu
                500                 505                 510
Ala Pro Glu Leu Tyr
                515
```

(Protein sequence of P72L variant of CYP82E5 nicotine demethylase)

SEQ ID NO: 18

```
Met Val Ser Pro Val Glu Ala Ile Val Gly Leu Val Thr Leu Thr Leu
  1               5                  10                  15
Leu Phe Tyr Phe Leu Trp Pro Lys Lys Phe Gln Ile Pro Ser Lys Pro
                 20                  25                  30
Leu Pro Pro Lys Ile Pro Gly Gly Trp Pro Val Ile Gly His Leu Phe
                 35                  40                  45
Tyr Phe Asp Asp Gly Asp Asp Arg Pro Leu Ala Arg Lys Leu Gly
                 50                  55                  60
Asp Leu Ala Asp Lys Tyr Gly Leu Val Phe Thr Phe Arg Leu Gly Leu
 65                  70                  75                  80
Pro Leu Val Leu Val Ser Ser Tyr Glu Ala Val Lys Asp Cys Phe
                 85                  90                  95
Ser Thr Asn Asp Ala Ile Phe Ser Asn Arg Pro Ala Phe Leu Tyr Gly
                100                 105                 110
Glu Tyr Leu Gly Tyr Ser Asn Ala Met Leu Phe Leu Thr Lys Tyr Gly
                115                 120                 125
Pro Tyr Trp Arg Lys Asn Arg Lys Leu Val Ile Gln Glu Val Leu Ser
                130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
                180                 185                 190
Lys Met Ile Ala Gly Lys Asn Tyr Glu Ser Gly Lys Gly Asp Glu Gln
                195                 200                 205
Val Glu Arg Phe Arg Lys Ala Phe Lys Asp Phe Ile Ile Leu Ser Met
                210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Arg Glu
                260                 265                 270
Lys Met Glu Val Asn Ala Gln Gly Asn Glu Gln Asp Phe Ile Asp Val
                275                 280                 285
Val Leu Ser Lys Met Ser Asn Glu Tyr Leu Asp Glu Gly Tyr Ser Arg
```

-continued

```
                    290                 295                 300
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
                500                 505                 510

Ala Pro Glu Leu Tyr
            515
```

(Protein sequence of L143F variant of CYP82E5 nicotine demethylase)
SEQ ID NO: 19

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Phe Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190
```

```
Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

(Protein sequence of S174L variant of CYP82E5 nicotine demethylase)
                                                                    SEQ ID NO: 20
Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80
```

```
Pro Leu Val Leu Val Ser Ser Tyr Glu Ala Val Lys Asp Cys Phe
            85                  90                  95
Ser Thr Asn Asp Ala Ile Phe Ser Asn Arg Pro Ala Phe Leu Tyr Gly
            100                 105                 110
Glu Tyr Leu Gly Tyr Ser Asn Ala Met Leu Phe Leu Thr Lys Tyr Gly
            115                 120                 125
Pro Tyr Trp Arg Lys Asn Arg Lys Leu Val Ile Gln Glu Val Leu Ser
            130                 135                 140
Ala Ser Arg Leu Glu Lys Leu Lys His Val Arg Phe Gly Lys Ile Gln
145                 150                 155                 160
Thr Ser Ile Lys Ser Leu Tyr Thr Arg Ile Asp Gly Asn Leu Ser Thr
                165                 170                 175
Ile Asn Leu Thr Asp Trp Leu Glu Glu Leu Asn Phe Gly Leu Ile Val
                180                 185                 190
Lys Met Ile Ala Gly Lys Asn Tyr Glu Ser Gly Lys Gly Asp Glu Gln
                195                 200                 205
Val Glu Arg Phe Arg Lys Ala Phe Lys Asp Phe Ile Ile Leu Ser Met
            210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu His Val Lys Lys Arg Glu
            260                 265                 270
Lys Met Glu Val Asn Ala Gln Gly Asn Glu Gln Asp Phe Ile Asp Val
            275                 280                 285
Val Leu Ser Lys Met Ser Asn Glu Tyr Leu Asp Glu Gly Tyr Ser Arg
            290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
                340                 345                 350
Gly Lys Glu Arg Trp Val Glu Glu Ser Asp Ile Lys Asp Leu Val Tyr
            355                 360                 365
Leu Gln Ala Ile Val Lys Glu Val Leu Arg Leu Tyr Pro Pro Gly Pro
            370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
                420                 425                 430
Phe Phe Ala Asp Asp Ile Asp Tyr Arg Gly Gln His Tyr Glu Phe Ile
            435                 440                 445
Pro Phe Gly Ser Gly Arg Arg Ser Cys Pro Gly Met Thr Tyr Ala Leu
            450                 455                 460
Gln Ala Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Val Glu Val Thr Ile Thr Ala Arg Leu
                500                 505                 510
```

Ala Pro Glu Leu Tyr
        515

(Protein sequence of M224I variant of CYP82E5 nicotine demethylase)
SEQ ID NO: 21

Met Val Ser Pro Val Glu Ala Ile Val Gly Leu Val Thr Leu Thr Leu
 1               5                  10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Ile
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln

-continued

```
            405                 410                 415
Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515
```

(Protein sequence of P235S variant of CYP82E5 nicotine demethylase)

SEQ ID NO: 22

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Ser Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300
```

-continued

```
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Gly Ala Gly Leu
                485                 490                 495

Thr Ile Arg Lys Val Asn Pro Val Glu Val Thr Ile Thr Ala Arg Leu
                500                 505                 510

Ala Pro Glu Leu Tyr
            515

(Protein sequence of A410V variant of CYP82E5 nicotine demethylase)
                                                                        SEQ ID NO: 23
Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
                20                  25                  30

Leu Pro Pro Lys Ile Pro Gly Gly Trp Pro Val Ile Gly His Leu Phe
                35                  40                  45

Tyr Phe Asp Asp Asp Gly Asp Arg Pro Leu Ala Arg Lys Leu Gly
    50                  55                  60

Asp Leu Ala Asp Lys Tyr Gly Pro Val Phe Thr Phe Arg Leu Gly Leu
 65                 70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190
```

-continued

```
Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Val Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
        450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
```

(Protein sequence of W422Stop variant of CYP82E5 nicotine demethylase)

SEQ ID NO: 24

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95
```

```
Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu
            420

(Protein sequence of P449L variant of CYP82E5 nicotine demethylase)    SEQ ID NO: 25

Met Val Ser Pro Val Glu Ala Ile Val Gly Leu Val Thr Leu Thr Leu
  1               5                  10                  15

Leu Phe Tyr Phe Leu Trp Pro Lys Lys Phe Gln Ile Pro Ser Lys Pro
              20                  25                  30

Leu Pro Pro Lys Ile Pro Gly Gly Trp Pro Val Ile Gly His Leu Phe
              35                  40                  45

Tyr Phe Asp Asp Asp Gly Asp Asp Arg Pro Leu Ala Arg Lys Leu Gly
              50                  55                  60

Asp Leu Ala Asp Lys Tyr Gly Pro Val Phe Thr Phe Arg Leu Gly Leu
65                  70                  75                  80
```

```
Pro Leu Val Leu Val Ser Ser Tyr Glu Ala Val Lys Asp Cys Phe
             85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
            130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Leu Phe Gly Ser Gly Arg Arg Ser Cys Pro Gly Met Thr Tyr Ala Leu
450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510
```

Ala Pro Glu Leu Tyr
           515

(Protein sequence of CYP82E10 nicotine demethylase)    SEQ ID NO: 26

Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
             20                  25                  30

Leu Pro Pro Lys Ile Pro Gly Gly Trp Pro Val Ile Gly His Leu Phe
             35                  40                  45

Tyr Phe Asp Asp Ser Asp Asp Arg Pro Leu Ala Arg Lys Leu Gly
     50                  55                  60

Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
             100                 105                 110

Glu Tyr Leu Gly Tyr Asn Asn Ala Met Leu Phe Leu Thr Lys Tyr Gly
             115                 120                 125

Pro Tyr Trp Arg Lys Asn Arg Lys Leu Val Ile Gln Glu Val Leu Cys
             130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                 165                 170                 175

Ile Asn Leu Thr Asp Trp Leu Glu Glu Leu Asn Phe Gly Leu Ile Val
                 180                 185                 190

Lys Met Ile Ala Gly Lys Asn Tyr Glu Ser Gly Lys Gly Asp Glu Gln
                 195                 200                 205

Val Glu Arg Phe Arg Lys Ala Phe Lys Asp Phe Ile Ile Leu Ser Met
             210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                 245                 250                 255

Asp Ser Val Phe Gln Asn Trp Leu Glu Glu His Val Lys Lys Lys Glu
             260                 265                 270

Lys Met Glu Val Asn Ala Glu Gly Asn Glu Gln Asp Phe Ile Asp Val
             275                 280                 285

Val Leu Ser Lys Met Ser Asn Glu Tyr Leu Asp Glu Gly Tyr Ser Arg
             290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                 325                 330                 335

Asn Gln His Ala Leu Lys Lys Ala Gln Glu Glu Ile Asp Lys Lys Val
             340                 345                 350

Gly Lys Asp Arg Trp Val Glu Glu Ser Asp Ile Lys Asp Leu Val Tyr
             355                 360                 365

Leu Gln Thr Ile Val Lys Glu Val Leu Arg Leu Tyr Pro Pro Gly Pro
             370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln

```
                            405                 410                 415
Arg Asp Pro Lys Leu Trp Ser Asn Pro Asp Lys Phe Asp Pro Glu Arg
                420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
    515

(Protein sequence of L148F variant of CYP82E10 nicotine demethylase)
                                                                    SEQ ID NO: 27
Met Val Ser Pro Val Glu Ala Ile Val Gly Leu Val Thr Leu Thr Leu
  1               5                  10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
    115                 120                 125

Pro Tyr Trp Arg Lys Asn Arg Lys Leu Val Ile Gln Glu Val Leu Cys
    130                 135                 140

Ala Ser Arg Phe Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
    195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Asp Glu Gly Tyr Ser Arg
    290                 295                 300
```

-continued

```
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
                340                 345                 350

Gly Lys Asp Arg Trp Val Glu Glu Ser Asp Ile Lys Asp Leu Val Tyr
                355                 360                 365

Leu Gln Thr Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Ala Asp Ile Asp Phe Arg Gly Gln His Tyr Glu Phe Ile
                435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
                515

(Protein sequence of G172R variant of CYP82E10 nicotine demethylase)
                                                                    SEQ ID NO: 28
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
                35                  40                  45

Tyr Phe Asp Asp Asp Ser Asp Arg Pro Leu Ala Arg Lys Leu Gly
            50                  55                  60

Asp Leu Ala Asp Lys Tyr Gly Pro Val Phe Thr Phe Arg Leu Gly Leu
65              70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
                115                 120                 125

Pro Tyr Trp Arg Lys Asn Arg Lys Leu Val Ile Gln Glu Val Leu Cys
                130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Arg Asn Ser Ser Thr
                165                 170                 175

Ile Asn Leu Thr Asp Trp Leu Glu Glu Leu Asn Phe Gly Leu Ile Val
                180                 185                 190
```

-continued

```
Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
            515
```

(Protein sequence of A344T variant of CYP82E10 nicotine demethylase)
SEQ ID NO: 29

```
Met Val Ser Pro Val Glu Ala Ile Val Gly Leu Val Thr Leu Thr Leu
  1               5                  10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
```

-continued

```
                85                  90                  95
Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
            130                 135                 140

Ala Ser Arg Leu Glu Lys Leu Lys His Val Arg Phe Gly Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Thr Gln Glu Glu Ile Asp Lys Lys Val
            340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
            450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
```

-continued

515

(Protein sequence of A410T variant of CYP82E10 nicotine demethylase)

SEQ ID NO: 30

```
Met Val Ser Pro Val Glu Ala Ile Val Gly Leu Val Thr Leu Thr Leu
 1               5                  10                  15

Leu Phe Tyr Phe Ile Arg Thr Lys Lys Ser Gln Lys Pro Ser Lys Pro
             20                  25                  30

Leu Pro Pro Lys Ile Pro Gly Gly Trp Pro Val Ile Gly His Leu Phe
         35                  40                  45

Tyr Phe Asp Asp Asp Ser Asp Arg Pro Leu Ala Arg Lys Leu Gly
     50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Thr Asn Val Met Lys Leu Gln
                405                 410                 415
```

-continued

```
Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
        450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
            515
```

(Protein sequence of R417H variant of CYP82E10 nicotine demethylase)

SEQ ID NO: 31

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
            130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300
```

-continued

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
        340                 345                 350

Gly Lys Asp Arg Trp Val Glu Glu Ser Asp Ile Lys Asp Leu Val Tyr
    355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

His Asp Pro Lys Leu Trp Ser Asn Pro Asp Lys Phe Asp Pro Glu Arg
        420                 425                 430

Phe Phe Ala Ala Asp Ile Asp Phe Arg Gly Gln His Tyr Glu Phe Ile
    435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
        500                 505                 510

Thr Pro Glu Leu Tyr
        515

(Protein sequence of P419S variant of CYP82E10 nicotine demethylase)

SEQ ID NO: 32

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Ser Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
            85                  90                  95

Ser Thr Asn Asp Ala Ile Phe Ser Asn Arg Pro Ala Phe Leu Tyr Gly
        100                 105                 110

Glu Tyr Leu Gly Tyr Asn Asn Ala Met Leu Phe Leu Thr Lys Tyr Gly
    115                 120                 125

Pro Tyr Trp Arg Lys Asn Arg Lys Leu Val Ile Gln Glu Val Leu Cys
130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
        180                 185                 190

Lys Met Ile Ala Gly Lys Asn Tyr Glu Ser Gly Lys Gly Asp Glu Gln

```
                195                 200                 205
Val Glu Arg Phe Arg Lys Ala Phe Lys Asp Phe Ile Ile Leu Ser Met
210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Lys Glu
                260                 265                 270
Lys Met Glu Val Asn Ala Glu Gly Asn Glu Gln Asp Phe Ile Asp Val
                275                 280                 285
Val Leu Ser Lys Met Ser Asn Glu Tyr Leu Asp Glu Gly Tyr Ser Arg
                290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
                340                 345                 350
Gly Lys Asp Arg Trp Val Glu Ser Asp Ile Lys Asp Leu Val Tyr
                355                 360                 365
Leu Gln Thr Ile Val Lys Glu Val Leu Arg Leu Tyr Pro Pro Gly Pro
                370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Ser Lys Leu Trp Ser Asn Pro Asp Lys Phe Asp Pro Glu Arg
                420                 425                 430
Phe Phe Ala Ala Asp Ile Asp Phe Arg Gly Gln His Tyr Glu Phe Ile
                435                 440                 445
Pro Phe Gly Ser Gly Arg Arg Ser Cys Pro Gly Met Thr Tyr Ala Met
                450                 455                 460
Gln Val Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Ile Glu Val Val Ile Thr Pro Arg Leu
                500                 505                 510
Thr Pro Glu Leu Tyr
        515
```

(Protein sequence of G79S variant of CYP82E10 nicotine demethylase)   SEQ ID NO: 33

```
Met Val Ser Pro Val Glu Ala Ile Val Gly Leu Val Thr Leu Thr Leu
1               5                   10                  15
Leu Phe Tyr Phe Ile Arg Thr Lys Lys Ser Gln Lys Pro Ser Lys Pro
                20                  25                  30
Leu Pro Pro Lys Ile Pro Gly Gly Trp Pro Val Ile Gly His Leu Phe
                35                  40                  45
Tyr Phe Asp Asp Asp Ser Asp Asp Arg Pro Leu Ala Arg Lys Leu Gly
                50                  55                  60
Asp Leu Ala Asp Lys Tyr Gly Pro Val Phe Thr Phe Arg Leu Ser Leu
65                  70                  75                  80
Pro Leu Val Leu Val Val Ser Ser Tyr Glu Ala Ile Lys Asp Cys Phe
                85                  90                  95
```

```
Ser Thr Asn Asp Ala Ile Phe Ser Asn Arg Pro Ala Phe Leu Tyr Gly
                100                 105                 110
Glu Tyr Leu Gly Tyr Asn Asn Ala Met Leu Phe Leu Thr Lys Tyr Gly
            115                 120                 125
Pro Tyr Trp Arg Lys Asn Arg Lys Leu Val Ile Gln Glu Val Leu Cys
        130                 135                 140
Ala Ser Arg Leu Glu Lys Leu Lys His Val Arg Phe Gly Glu Ile Gln
145                 150                 155                 160
Thr Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Lys Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Asp Glu Gly Tyr Ser Arg
            290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
            340                 345                 350
Gly Lys Asp Arg Trp Val Glu Glu Ser Asp Ile Lys Asp Leu Val Tyr
        355                 360                 365
Leu Gln Thr Ile Val Lys Glu Val Leu Arg Leu Tyr Pro Pro Gly Pro
370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asn Pro Asp Lys Phe Asp Pro Glu Arg
            420                 425                 430
Phe Phe Ala Ala Asp Ile Asp Phe Arg Gly Gln His Tyr Glu Phe Ile
        435                 440                 445
Pro Phe Gly Ser Gly Arg Arg Ser Cys Pro Gly Met Thr Tyr Ala Met
    450                 455                 460
Gln Val Glu His Leu Thr Ile Ala His Leu Ile Gln Gly Phe Asn Tyr
465                 470                 475                 480
Lys Thr Pro Asn Asp Glu Pro Leu Asp Met Lys Glu Gly Ala Gly Leu
                485                 490                 495
Thr Ile Arg Lys Val Asn Pro Ile Glu Val Val Ile Thr Pro Arg Leu
            500                 505                 510
Thr Pro Glu Leu Tyr
            515
```

-continued (Protein sequence of P107S variant of CYP82E10 nicotine demethylase)

SEQ ID NO: 34

```
Met Val Ser Pro Val Glu Ala Ile Val Gly Leu Val Thr Leu Thr Leu
 1               5                  10                  15
Leu Phe Tyr Phe Ile Arg Thr Lys Lys Ser Gln Lys Pro Ser Lys Pro
                20                  25                  30
Leu Pro Pro Lys Ile Pro Gly Gly Trp Pro Val Ile Gly His Leu Phe
            35                  40                  45
Tyr Phe Asp Asp Asp Ser Asp Asp Arg Pro Leu Ala Arg Lys Leu Gly
        50                  55                  60
Asp Leu Ala Asp Lys Tyr Gly Pro Val Phe Thr Phe Arg Leu Gly Leu
 65                  70                  75                  80
Pro Leu Val Leu Val Val Ser Ser Tyr Glu Ala Ile Lys Asp Cys Phe
                85                  90                  95
Ser Thr Asn Asp Ala Ile Phe Ser Asn Arg Ser Ala Phe Leu Tyr Gly
            100                 105                 110
Glu Tyr Leu Gly Tyr Asn Asn Ala Met Leu Phe Leu Thr Lys Tyr Gly
        115                 120                 125
Pro Tyr Trp Arg Lys Asn Arg Lys Leu Val Ile Gln Glu Val Leu Cys
130                 135                 140
Ala Ser Arg Leu Glu Lys Leu Lys His Val Arg Phe Gly Glu Ile Gln
145                 150                 155                 160
Thr Ser Ile Lys Asn Leu Tyr Thr Arg Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
        195                 200                 205
Val Glu Arg Phe Arg Lys Ala Phe Lys Asp Phe Ile Ile Leu Ser Met
210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Val Lys Lys Lys Glu
            260                 265                 270
Lys Met Glu Val Asn Ala Glu Gly Asn Glu Gln Asp Phe Ile Asp Val
        275                 280                 285
Val Leu Ser Lys Met Ser Asn Glu Tyr Leu Asp Glu Gly Tyr Ser Arg
290                 295                 300
Asp Thr Val Ile Lys Ala Thr Val Phe Ser Leu Val Leu Asp Ala Ala
305                 310                 315                 320
Asp Thr Val Ala Leu His Met Asn Trp Gly Met Ala Leu Leu Ile Asn
                325                 330                 335
Asn Gln His Ala Leu Lys Lys Ala Gln Glu Glu Ile Asp Lys Lys Val
            340                 345                 350
Gly Lys Asp Arg Trp Val Glu Glu Ser Asp Ile Lys Asp Leu Val Tyr
        355                 360                 365
Leu Gln Thr Ile Val Lys Glu Val Leu Arg Leu Tyr Pro Pro Gly Pro
370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
```

-continued

```
Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
            450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
            500                 505                 510

Thr Pro Glu Leu Tyr
            515
```

(Protein sequence of P382S variant of CYP82E10 nicotine demethylase)

SEQ ID NO: 35

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
            85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
            130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
```

-continued

```
                305                 310                 315                 320
Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
                340                 345                 350

Gly Lys Asp Arg Trp Val Glu Ser Asp Ile Lys Asp Leu Val Tyr
                355                 360                 365

Leu Gln Thr Ile Val Lys Glu Val Leu Arg Leu Tyr Pro Ser Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Ala Asp Ile Asp Phe Arg Gly Gln His Tyr Glu Phe Ile
                435                 440                 445

Pro Phe Gly Ser Gly Arg Arg Ser Cys Pro Gly Met Thr Tyr Ala Met
                450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
                515
```

The invention claimed is:

1. A transgenic tobacco plant cell comprising a recombinant construct including a polynucleotide that reduces or inhibits expression of a nicotine N-demethylase compared to a control tobacco plant which does not comprise said recombinant construct, wherein the nicotine N-demethylase comprises a polypeptide having the sequence of SEQ ID NO: 3.

2. The transgenic tobacco plant cell according to claim 1, wherein said tobacco plant cell further comprises one or more mutations that reduce the expression or activity of said nicotine N-demethylase.

3. The transgenic tobacco plant cell according to claim 1, further comprising one or more mutations in a gene encoding a CYP82E4 nicotine demethylase, wherein said mutation results in reduced expression or function of said CYP82E4 nicotine demethylase.

4. The transgenic tobacco plant cell according to claim 1, further comprising one or more mutations in a gene encoding a CYP82E5 nicotine demethylase, wherein said mutation results in reduced expression or function of said CYP82E5 nicotine demethylase.

5. The transgenic tobacco plant cell according to claim 1, further comprising one or more mutations in a gene encoding a CYP82E10 nicotine demethylase, wherein said mutation results in reduced expression or function of said CYP82E 10 nicotine demethylase.

6. The transgenic tobacco plant cell according to claim 1, further comprising
   (i) one or more mutations in a gene encoding a CYP82E4 nicotine demethylase, wherein said mutation results in reduced expression or function of said CYP82E4 nicotine demethylase; and
   (ii) one or more mutations in a gene encoding a CYP82E5 nicotine demethylase, wherein said mutation results in reduced expression or function of said CYP82E5 nicotine demethylase; and
   (iii) one or more mutations in a gene encoding a CYP82E10 nicotine demethylase, wherein said mutation results in reduced expression or function of said CYP82E10 nicotine demethylase.

7. The transgenic tobacco plant cell according to claim 1, further comprising:
   (i) one or more mutations in a gene encoding a CYP82E4 nicotine demethylase, one or more mutations in a gene encoding a CYP82E5 nicotine demethylase and one or more mutations in a gene encoding a CYP82E10 nicotine demethylase, wherein said CYP82E4 nicotine demethylase comprises the sequence set forth in SEQ ID NO: 13 and the mutation designated as W329Stop, said CYP82E5 nicotine demethylase comprises the sequence set forth in SEQ ID NO: 24 and the mutation designated as W422Stop, and said CYP82E10 nicotine demethylase comprises the sequence set forth in SEQ ID NO: 33 and the mutation designated as G79S; or
   (ii) one or more mutations in a gene encoding a CYP82E4 nicotine demethylase, one or more mutations in a gene encoding a CYP82ES nicotine demethylase and one or more mutations a gene encoding a CYP82E10 nicotine demethylase, wherein said CYP82E4 nicotine demethylase comprises the sequence set forth in SEQ ID NO: 13 and the mutation designated as W329Stop, said CYP82E5 nicotine demethylase comprises the sequence set forth in SEQ ID NO: 24 and the mutation designated as W422Stop, and said CYP82E10 nicotine demethylase comprises the sequence set forth in SEQ ID NO: 34 and the mutation designated as P107S; or
   (iii) one or more mutations in a gene encoding a CYP82E4 nicotine demethylase one or more mutations in a gene encoding a CYP82ES nicotine demethylase and one or more mutations in a gene encoding a CYP82E10 nicotine demethylase, wherein said CYP82E4 nicotine demethylase comprises the sequence set forth in SEQ ID NO: 13 and the mutation designated as W329Stop, said CYP82E5 nicotine demethylase comprises the sequence set forth in SEQ ID NO: 24 and the mutation designated as W422Stop, and said CYP82E10 nicotine demethylase comprises the sequence set forth in SEQ ID NO: 35 and the mutation designated as P382S; or
   (iv) one or more mutations in a gene encoding a CYP82E4 nicotine demethylase, one or more mutations in a gene encoding a CYP82E5 nicotine demethylase and one or more mutations in a gene encoding a CYP82E10 nicotine demethylase, wherein said CYP82E4 nicotine demethylase comprises the sequence set forth in SEQ ID NO: 13 and the mutation designated as W329Stop, said CYP82E5 nicotine demethylase comprises the sequence set forth in SEQ ID NO: 24 and the mutation designated as W422Stop, and said CYP82E10 nicotine demethylase comprises the sequence set forth in SEQ ID NO: 32 and the mutation designated as P419S.

8. The transgenic tobacco plant cell according to claim 2, wherein said mutation(s) is a heterozygous or homozygous mutation.

9. The transgenic tobacco plant cell according to claim 1, wherein said plant cell has a less than 1% conversion of nicotine to nornicotine.

10. A transgenic plant or component or part thereof comprising the transgenic plant cell according to claim 1.

11. Plant material including biomass, seed, stem, flowers or leaves from the transgenic plant of claim 10, comprising the transgenic plant cell.

12. A tobacco product comprising the transgenic tobacco plant cell of claim 1.

* * * * *

SEQUENCE LISTING

<160> NUMBER OF SEQ ID NOS: 47

<210> SEQ ID NO 1
<211> LENGTH: 2088
<212> TYPE: DNA
<213> ORGANISM: Nicotiana tabacum

<400> SEQUENCE: 1

```
atggttttc  ccatagaagc cattgtagga ctagtaacct tcacatttct cttctacttc    60
ctatggacaa aaaatctca  aaaaccttca aaacccttac caccgaaaat ccccggagga   120
tggccggtaa ttggccatct tttccacttc aatgacgacg gcaacgaccg tccattagct   180
cgaaaactcg gagacttagc tgacaaatac ggccccgttt tcacttttcg gctaggcctt   240
cccttgtgt  tagttgtaag cagttacgaa gctataaaag actgtttctc tacaaatgat   300
gccattttct ctaatcgtcc agcttttctt tacggcgaat accttggcta caataatgcc   360
atgctatttt tggcaaatta cggaccttac tggcgaaaaa atcgtaaatt agttattcag   420
gaagttctct cagctagtcg tctcaaaaaa ttcaaacacg tgagattcgc cagaattcaa   480
acgagcatta agaatttata cactcgaatt gatagaaatt cgagtacgat aaatttaact   540
gattggttag aagaattgaa ttttggtctc atcgtgaaga tgatagctgg gaaaaattat   600
gaatccggta aaggagatga acaagtggag agatttaaga aagcgtttaa ggattttatg   660
attatatcaa tggagtttgt gttatgggat gcatttccaa ttccattatt taaatgggtg   720
gattttcaag ggcatgttaa ggctatgaaa aggacattta aggatataga ttctgttttt   780
```

```
cagaattggt tagaggaaca tattaacaaa agagaaaaaa tggaggttaa tgcagaaggg      840
aatgaacaag atttcattga tgtggtgctt tcaaaaatga gtaatgaata tcttggtgaa      900
ggttactctc gtgatactgt cataaaagca acagttttg  taagttcatc tgtcactccc      960
gaattctgct tgaatgcaga caccgagttg ccttttatt  agactatcta aatattaagg     1020
atgattatat atagcaaaaa tatagtagga tttctcgggc tttgggatag aagaatattc     1080
atcattatat aacttttgat ggtaaaagat gagatctaac ctcttataat tgcccaacca     1140
cgttgatata tagaacaaaa ccttttact  cccattgagc ataacgaaaa tgaaagcaaa     1200
gggacttctt ctcttttta  ggaaaaaaat ctttgattgc ttgttaata  tacattcatg     1260 tttttctttt tctatttcta ataataatgg tgcttgaatc aggttgcgtg cctcgtgact     1320
tttgagaaaa aaaacaaat  tcattagtat aatgaggtgt gcatacttga caactactat     1380
actaactaga acaaggttcg gcagataatg acgctaacct actttatat  tgaattatca     1440 tttgtattta actgtattct attttgtcca cagagtttgg tcttggatgc tgcggacaca     1500
gttgctcttc acataaattg gggtatggca ttactgatca acaatcaaaa tgccttgaag     1560
aaagcacaag aagagataga cacaaaagtt ggcaaggata gatgggtaga agagagtgat     1620
attaaggatt tggtgtacct ccaagctatt gttaaagaag tgttacgatt atatccaccg     1680
ggacctttgt tagtaccaca tgaaaatata gaggattgtg ttgttagtgg atattacatt     1740
tctaaaggga ctagactatt cgcaaatgtt atgaaactgc agcgcgatcc taaactctgg     1800
ccaaatcctg ataatttcga tccagagaga tttgtcgctg caggtattga ctttcgtggt     1860
cagcattatg agtatatccc gtttggttct ggaagacgat cttgtccggg gatgacttat     1920
gcattgcaag tggaacactt aacaatggca catttgatcc agggtttcaa ttacagcact     1980
ccaaatgacg agcccttgga tatgaaggaa ggtgcaggta taactatacg taaggtaaat     2040
cccgtggaag tgataattat gcctcgcctg gcacctgagc tttattaa                  2088
```

<210> SEQ ID NO 2
<211> LENGTH: 1554
<212> TYPE: DNA
<213> ORGANISM: Nicotiana tabacum

<400> SEQUENCE: 2

```
atggttttc  ccatagaagc cattgtagga ctagtaacct tcacatttct cttctacttc       60
ctatggacaa aaaatctca  aaaaccttca aaacccttac caccgaaaat ccccggagga      120
tggccggtaa ttggccatct tttccacttc aatgacgacg gcaacgaccg tccattagct      180
cgaaaactcg gagacttagc tgacaaatac ggccccgttt tcacttttcg gctaggcctt      240 cccccttgtgt tagttgtaag cagttacgaa gctataaaag actgtttctc tacaaatgat      300 gccatttct  ctaatcgtcc agcttttctt tacggcgaat accttggcta caataatgcc      360
atgctatttt tggcaaatta cggaccttac tggcgaaaaa atcgtaaatt agttattcag      420
gaagttctct cagctagtcg tctcaaaaaa ttcaaacacg tgagattcgc cagaattcaa      480
acgagcatta agaatttata cactcgaatt gatagaaatt cgagtacgat aaatttaact      540
gattggttag aagaattgaa ttttggtctc atcgtgaaga tgatagctgg gaaaaattat      600
gaatccggta aggagatgaa acaagtggag agatttaaga aagcgtttaa ggattttatg      660
attatatcaa tggagtttgt gttatgggat gcatttccaa ttccattatt taaatgggtg      720
gattttcaag ggcatgttaa ggctatgaaa aggacatttta aggatataga ttctgttttt      780
```

```
cagaattggt tagaggaaca tattaacaaa agagaaaaaa tggaggttaa tgcagaaggg    840
aatgaacaag atttcattga tgtggtgctt tcaaaaatga gtaatgaata tcttggtgaa    900
ggttactctc gtgatactgt cataaaagca acagttttta gtttggtctt ggatgctgcg    960
gacacagttg ctcttcacat aaattggggt atggcattac tgatcaacaa tcaaaatgcc   1020
ttgaagaaag cacaagaaga gatagacaca aaagttggca aggatagatg ggtagaagag   1080
agtgatatta aggatttggt gtacctccaa gctattgtta agaagtgtt acgattatat    1140 ccaccgggac ctttgttagt accacatgaa aatatagagg attgtgttgt tagtggatat   1200
tacatttcta aagggactag actattcgca aatgttatga actgcagcg cgatcctaaa    1260 ctctggccaa atcctgataa tttcgatcca gagagatttg tcgctgcagg tattgacttt   1320
cgtggtcagc attatgagta tatcccgttt ggttctggaa gacgatcttg tccggggatg   1380
acttatgcat tgcaagtgga acacttaaca atggcacatt tgatccaggg tttcaattac   1440
agcactccaa atgacgagcc cttggatatg aaggaaggtg caggtataac tatacgtaag   1500
gtaaatcccg tggaagtgat aattatgcct cgcctggcac ctgagcttta ttaa         1554
```

<210> SEQ ID NO 3
<211> LENGTH: 517
<212> TYPE: PRT
<213> ORGANISM: Nicotiana tabacum

<400> SEQUENCE: 3

```
Met Val Phe Pro Ile Glu Ala Ile Val Gly Leu Val Thr Phe Thr Phe
  1               5                  10                  15

Leu Phe Tyr Phe Leu Trp Thr Lys Lys Ser Gln Lys Pro Ser Lys Pro
                 20                  25                  30

Leu Pro Pro Lys Ile Pro Gly Gly Trp Pro Val Ile Gly His Leu Phe
             35                  40                  45

His Phe Asn Asp Asp Gly Asn Asp Arg Pro Leu Ala Arg Lys Leu Gly
         50                  55                  60

Asp Leu Ala Asp Lys Tyr Gly Pro Val Phe Thr Phe Arg Leu Gly Leu
 65                  70                  75                  80

Pro Leu Val Leu Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Lys Lys Phe Lys His Val Arg Phe Ala Arg Ile Gln
145                 150                 155                 160

Thr Ser Ile Lys Asn Leu Tyr Thr Arg Ile Asp Arg Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Ile Ser Met
    210                 215                 220

Glu Phe Val Leu Trp Asp Ala Phe Pro Ile Pro Leu Phe Lys Trp Val
225                 230                 235                 240
```

| | | | | | | | | | | | |
|---|---|---|---|---|---|---|---|---|---|---|---|
|Asp|Phe|Gln|Gly|His|Val|Lys|Ala|Met|Lys|Arg|Thr|Phe|Lys|Asp|Ile|
| | | |245| | | |250| | | |255|

Asp Phe Gln Gly His Val Lys Ala Met Lys Arg Thr Phe Lys Asp Ile
                    245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Asn Ala Leu Lys Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Ile Glu Asp Cys Val Val Ser Gly Tyr
385                 390                 395                 400

Tyr Ile Ser Lys Gly Thr Arg Leu Phe Ala Asn Val Met Lys Leu Gln
                405                 410                 415

Arg Asp Pro Lys Leu Trp Pro Asn Pro Asp Asn Phe Asp Pro Glu Arg
            420                 425                 430

Phe Val Ala Ala Gly Ile Asp Phe Arg Gly Gln His Tyr Glu Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Ser Thr Pro Asn Asp Glu Pro Leu Asp Met Lys Glu Gly Ala Gly Ile
                485                 490                 495

Thr Ile Arg Lys Val Asn Pro Val Glu Val Ile Ile Met Pro Arg Leu
            500                 505                 510

Ala Pro Glu Leu Tyr
        515

<210> SEQ ID NO 4
<211> LENGTH: 469
<212> TYPE: DNA
<213> ORGANISM: Artificial sequence
<220> FEATURE:
<223> OTHER INFORMATION: Synthetic sequence: Polynucleotide sequence an
      RNAi construct using a 100bp unique sequence of NND3 in forward
      and reverse direction separated by an intron sequence found in the
      IPMS2 gene

<400> SEQUENCE: 4
gcgatcctaa actctggcca atcctgata atttcgatcc agagagattt gtcgctgcag      60
gtattgactt tcgtggtcag cattatgagt atatcccgtt tggtaacctt taatgtttaa    120
ccgttcacat ttctaatatt tactattttg taacatgtcg tcacgtgtta gtttcattct    180
ttttatgaac caaacatgca tgcaaagata ttttagata tttggacggc gagtgagatt    240
tgaaactagg accgtttgcc tgatacaata ttaaaatatg taaccatttt atgtacaagt    300
ttaaactgtt gatagtagca tatttttttac ttttatttaa gtatactata ttccaacagg    360

```
taagttaaca acgggatata ctcataatgc tgaccacgaa agtcaatacc tgcagcgaca      420
aatctctctg gatcgaaatt atcaggattt ggccagagtt taggatcgc                 469
```

<210> SEQ ID NO 5
<211> LENGTH: 517
<212> TYPE: PRT
<213> ORGANISM: Artificial sequence
<220> FEATURE:
<223> OTHER INFORMATION: Synthetic sequence: Protein sequence of CYP82E4
      nicotine demethylase

<400> SEQUENCE: 5

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
```

```
                    340                 345                 350
Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
        420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Arg Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
        500                 505                 510

Ala Pro Glu Leu Tyr
        515

<210> SEQ ID NO 6
<211> LENGTH: 517
<212> TYPE: PRT
<213> ORGANISM: Artificial sequence
<220> FEATURE:
<223> OTHER INFORMATION: Synthetic sequence: Protein sequence of P38L
      variant CYP82E4 nicotine demethylase

<400> SEQUENCE: 6

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Leu Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
            85                  90                  95

Ser Thr Asn Asp Ala Ile Phe Ser Asn Arg Pro Ala Phe Leu Tyr Gly
        100                 105                 110

Asp Tyr Leu Gly Tyr Asn Asn Ala Met Leu Phe Leu Ala Asn Tyr Gly
    115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Arg Ile Asp Gly Asn Ser Ser Thr
            165                 170                 175
```

```
Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 7
<211> LENGTH: 517
<212> TYPE: PRT
<213> ORGANISM: Artificial sequence
<220> FEATURE:
<223> OTHER INFORMATION: Synthetic sequence: Protein sequence of D171N
      variant CYP82E4 nicotine demethylase

<400> SEQUENCE: 7

Met Leu Ser Pro Ile Glu Ala Ile Val Gly Leu Val Thr Phe Thr Phe
1               5                   10                  15
```

```
Leu Phe Phe Phe Leu Trp Thr Lys Lys Ser Gln Lys Pro Ser Lys Pro
             20                  25                  30

Leu Pro Pro Lys Ile Pro Gly Gly Trp Pro Val Ile Gly His Leu Phe
         35                  40                  45

His Phe Asn Asp Asp Gly Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Val Lys Asp Cys Phe
                 85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asn Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Gly Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430
```

-continued

```
Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 8
<211> LENGTH: 517
<212> TYPE: PRT
<213> ORGANISM: Artificial sequence
<220> FEATURE:
<223> OTHER INFORMATION: Synthetic sequence: Protein sequence of E210K
      variant CYP82E4 nicotine demethylase

<400> SEQUENCE: 8

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Lys Ser Gly Lys Gly Asp Glu Gln
        195                 200                 205

Val Glu Arg Phe Lys Lys Ala Phe Lys Asp Phe Met Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270
```

```
Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
                340                 345                 350

Gly Lys Asp Arg Trp Val Glu Ser Asp Ile Lys Asp Leu Val Tyr
                355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515

<210> SEQ ID NO 9
<211> LENGTH: 517
<212> TYPE: PRT
<213> ORGANISM: Artificial sequence
<220> FEATURE:
<223> OTHER INFORMATION: Synthetic sequence: Protein sequence of R169Q
      variant CYP82E4 nicotine demethylase

<400> SEQUENCE: 9

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
```

```
                100                 105                 110
Asp Tyr Leu Gly Tyr Asn Asn Ala Met Leu Phe Leu Ala Asn Tyr Gly
            115                 120                 125
Pro Tyr Trp Arg Lys Asn Arg Lys Leu Val Ile Gln Glu Val Leu Ser
130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Gln Ile Asp Gly Asn Ser Ser Thr
                165                 170                 175
Ile Asn Leu Thr Asp Trp Leu Glu Glu Leu Asn Phe Gly Leu Ile Val
            180                 185                 190
Lys Met Ile Ala Gly Lys Asn Tyr Glu Ser Gly Lys Gly Asp Glu Gln
            195                 200                 205
Val Glu Arg Phe Lys Lys Ala Phe Lys Asp Phe Met Ile Leu Ser Met
            210                 215                 220
Glu Phe Val Leu Trp Asp Ala Phe Pro Ile Pro Leu Phe Lys Trp Val
225                 230                 235                 240
Asp Phe Gln Gly His Val Lys Ala Met Lys Arg Thr Phe Lys Asp Ile
                245                 250                 255
Asp Ser Val Phe Gln Asn Trp Leu Glu Glu His Ile Asn Lys Arg Glu
            260                 265                 270
Lys Met Glu Val Asn Ala Glu Gly Asn Glu Gln Asp Phe Ile Asp Val
            275                 280                 285
Val Leu Ser Lys Met Ser Asn Glu Tyr Leu Gly Glu Gly Tyr Ser Arg
            290                 295                 300
Asp Thr Val Ile Lys Ala Thr Val Phe Ser Leu Val Leu Asp Ala Ala
305                 310                 315                 320
Asp Thr Val Ala Leu His Ile Asn Trp Gly Met Ala Leu Leu Ile Asn
                325                 330                 335
Asn Gln Lys Ala Leu Thr Lys Ala Gln Glu Glu Ile Asp Thr Lys Val
            340                 345                 350
Gly Lys Asp Arg Trp Val Glu Glu Ser Asp Ile Lys Asp Leu Val Tyr
            355                 360                 365
Leu Gln Ala Ile Val Lys Glu Val Leu Arg Leu Tyr Pro Pro Gly Pro
370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
                405                 410                 415
Arg Asp Pro Lys Leu Trp Ser Asp Pro Asp Thr Phe Asp Pro Glu Arg
            420                 425                 430
Phe Ile Ala Thr Asp Ile Asp Phe Arg Gly Gln Tyr Tyr Lys Tyr Ile
            435                 440                 445
Pro Phe Gly Ser Gly Arg Arg Ser Cys Pro Gly Met Thr Tyr Ala Leu
            450                 455                 460
Gln Val Glu His Leu Thr Met Ala His Leu Ile Gln Gly Phe Asn Tyr
465                 470                 475                 480
Arg Thr Pro Asn Asp Glu Pro Leu Asp Met Lys Glu Gly Ala Gly Ile
                485                 490                 495
Thr Ile Arg Lys Val Asn Pro Val Glu Leu Ile Ile Ala Pro Arg Leu
            500                 505                 510
Ala Pro Glu Leu Tyr
            515
```

```
<210> SEQ ID NO 10
<211> LENGTH: 517
<212> TYPE: PRT
<213> ORGANISM: Artificial sequence
<220> FEATURE:
<223> OTHER INFORMATION: Synthetic sequence: Protein sequence of G459R
      variant CYP82E4 nicotine demethylase

<400> SEQUENCE: 10
```

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr

```
            355                 360                 365
Leu Gln Ala Ile Val Lys Glu Val Leu Arg Leu Tyr Pro Pro Gly Pro
            370                 375                 380
Leu Leu Val Pro His Glu Asn Val Glu Asp Cys Val Val Ser Gly Tyr
385                 390                 395                 400
His Ile Pro Lys Gly Thr Arg Leu Phe Ala Asn Val Met Lys Leu Gln
            405                 410                 415
Arg Asp Pro Lys Leu Trp Ser Asp Pro Asp Thr Phe Asp Pro Glu Arg
        420                 425                 430
Phe Ile Ala Thr Asp Ile Asp Phe Arg Gly Gln Tyr Tyr Lys Tyr Ile
            435                 440                 445
Pro Phe Gly Ser Gly Arg Arg Ser Cys Pro Arg Met Thr Tyr Ala Leu
        450                 455                 460
Gln Val Glu His Leu Thr Met Ala His Leu Ile Gln Gly Phe Asn Tyr
465                 470                 475                 480
Arg Thr Pro Asn Asp Glu Pro Leu Asp Met Lys Glu Gly Ala Gly Ile
            485                 490                 495
Thr Ile Arg Lys Val Asn Pro Val Glu Leu Ile Ile Ala Pro Arg Leu
            500                 505                 510
Ala Pro Glu Leu Tyr
            515

<210> SEQ ID NO 11
<211> LENGTH: 517
<212> TYPE: PRT
<213> ORGANISM: Artificial sequence
<220> FEATURE:
<223> OTHER INFORMATION: Synthetic sequence: Protein sequence of T427I
      variant CYP82E4 nicotine demethylase

<400> SEQUENCE: 11

Met Leu Ser Pro Ile Glu Ala Ile Val Gly Leu Val Thr Phe Thr Phe
1               5                   10                  15
Leu Phe Phe Phe Leu Trp Thr Lys Lys Ser Gln Lys Pro Ser Lys Pro
            20                  25                  30
Leu Pro Pro Lys Ile Pro Gly Gly Trp Pro Val Ile Gly His Leu Phe
        35                  40                  45
His Phe Asn Asp Asp Gly Asp Asp Arg Pro Leu Ala Arg Lys Leu Gly
    50                  55                  60
Asp Leu Ala Asp Lys Tyr Gly Pro Val Phe Thr Phe Arg Leu Gly Leu
65                  70                  75                  80
Pro Leu Val Leu Val Ser Ser Tyr Glu Ala Val Lys Asp Cys Phe
            85                  90                  95
Ser Thr Asn Asp Ala Ile Phe Ser Asn Arg Pro Ala Phe Leu Tyr Gly
            100                 105                 110
Asp Tyr Leu Gly Tyr Asn Asn Ala Met Leu Phe Leu Ala Asn Tyr Gly
        115                 120                 125
Pro Tyr Trp Arg Lys Asn Arg Lys Leu Val Ile Gln Glu Val Leu Ser
    130                 135                 140
Ala Ser Arg Leu Glu Lys Phe Lys His Val Arg Phe Ala Arg Ile Gln
145                 150                 155                 160
Ala Ser Ile Lys Asn Leu Tyr Thr Arg Ile Asp Gly Asn Ser Ser Thr
            165                 170                 175
Ile Asn Leu Thr Asp Trp Leu Glu Glu Leu Asn Phe Gly Leu Ile Val
            180                 185                 190
```

```
Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Ile Asn Lys Arg Glu
        260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Ile Phe Asp Pro Glu Arg
            420                 425                 430

Phe Ile Ala Thr Asp Ile Asp Phe Arg Gly Gln Tyr Tyr Lys Tyr Ile
        435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 12
<211> LENGTH: 517
<212> TYPE: PRT
<213> ORGANISM: Artificial sequence
<220> FEATURE:
<223> OTHER INFORMATION: Synthetic sequence: Protein sequence of V376M
      variant CYP82E4 nicotine demethylase

<400> SEQUENCE: 12

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30
```

```
Leu Pro Pro Lys Ile Pro Gly Gly Trp Pro Val Ile Gly His Leu Phe
            35              40                  45

His Phe Asn Asp Asp Gly Asp Arg Pro Leu Ala Arg Lys Leu Gly
 50              55                  60

Asp Leu Ala Asp Lys Tyr Gly Pro Val Phe Thr Phe Arg Leu Gly Leu
 65              70                  75                      80

Pro Leu Val Leu Val Val Ser Ser Tyr Glu Ala Val Lys Asp Cys Phe
                 85              90                  95

Ser Thr Asn Asp Ala Ile Phe Ser Asn Arg Pro Ala Phe Leu Tyr Gly
            100             105                 110

Asp Tyr Leu Gly Tyr Asn Asn Ala Met Leu Phe Leu Ala Asn Tyr Gly
            115             120                 125

Pro Tyr Trp Arg Lys Asn Arg Lys Leu Val Ile Gln Glu Val Leu Ser
        130             135                 140

Ala Ser Arg Leu Glu Lys Phe Lys His Val Arg Phe Ala Arg Ile Gln
145             150                 155                 160

Ala Ser Ile Lys Asn Leu Tyr Thr Arg Ile Asp Gly Asn Ser Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
        210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Met Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445
```

```
Pro Phe Gly Ser Gly Arg Arg Ser Cys Pro Gly Met Thr Tyr Ala Leu
    450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
            515

<210> SEQ ID NO 13
<211> LENGTH: 328
<212> TYPE: PRT
<213> ORGANISM: Artificial sequence
<220> FEATURE:
<223> OTHER INFORMATION: Synthetic sequence: Protein sequence of
      W329Stop variant CYP82E4 nicotine demethylase

<400> SEQUENCE: 13

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285
```

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn
                325

<210> SEQ ID NO 14
<211> LENGTH: 517
<212> TYPE: PRT
<213> ORGANISM: Artificial sequence
<220> FEATURE:
<223> OTHER INFORMATION: Synthetic sequence: Protein sequence of K364N
      variant CYP82E4 nicotine demethylase

<400> SEQUENCE: 14

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
    130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
            195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
    275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala

Asp Thr Val Ala Leu His Ile Asn Trp Gly Met Ala Leu Leu Ile Asn
305                 310                 315                 320

Asn Gln Lys Ala Leu Thr Lys Ala Gln Glu Ile Asp Thr Lys Val
            325                 330                 335

Gly Lys Asp Arg Trp Val Glu Ser Asp Ile Asn Asp Leu Val Tyr
            355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Pro Gly Met Thr Tyr Ala Leu
450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
        515

<210> SEQ ID NO 15
<211> LENGTH: 517
<212> TYPE: PRT
<213> ORGANISM: Artificial sequence
<220> FEATURE:
<223> OTHER INFORMATION: Synthetic sequence: Protein sequence of P382S
      variant CYP82E4 nicotine demethylase

<400> SEQUENCE: 15

Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Asp Tyr Leu Gly Tyr Asn Asn Ala Met Leu Phe Leu Ala Asn Tyr Gly
        115                 120                 125

Pro Tyr Trp Arg Lys Asn Arg Lys Leu Val Ile Gln Glu Val Leu Ser
    130                 135                 140

```
Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
                260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Glu Ile Asp Thr Lys Val
                340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Ser Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asp Pro Asp Thr Phe Asp Pro Glu Arg
                420                 425                 430

Phe Ile Ala Thr Asp Ile Asp Phe Arg Gly Gln Tyr Tyr Lys Tyr Ile
                435                 440                 445

Pro Phe Gly Ser Gly Arg Arg Ser Cys Pro Gly Met Thr Tyr Ala Leu
        450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
                485                 490                 495

Thr Ile Arg Lys Val Asn Pro Val Glu Leu Ile Ile Ala Pro Arg Leu
                500                 505                 510

Ala Pro Glu Leu Tyr
        515

<210> SEQ ID NO 16
<211> LENGTH: 517
<212> TYPE: PRT
<213> ORGANISM: Artificial sequence
<220> FEATURE:
<223> OTHER INFORMATION: Synthetic sequence: Protein sequence of P458S
``` variant CYP82E4 nicotine demethylase

<400> SEQUENCE: 16

```
Met Leu Ser Pro Ile Glu Ala Ile Val Gly Leu Val Thr Phe Thr Phe
1               5                   10                  15

Leu Phe Phe Phe Leu Trp Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

His Phe Asn Asp Asp Gly Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
                100                 105                 110

Asp Tyr Leu Gly Tyr Asn Asn Ala Met Leu Phe Leu Ala Asn Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Phe Lys His Val Arg Phe Ala Arg Ile Gln
145                 150                 155                 160

Ala Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Lys Lys Ala Phe Lys Asp Phe Met Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Ile Asn Lys Arg Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Gly Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Ile Asn Trp Gly Met Ala Leu Leu Ile Asn
                325                 330                 335

Asn Gln Lys Ala Leu Thr Lys Ala Gln Glu Ile Asp Thr Lys Val
            340                 345                 350

Gly Lys Asp Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400
```

His Ile Pro Lys Gly Thr Arg Leu Phe Ala Asn Val Met Lys Leu Gln
            405                 410                 415

Arg Asp Pro Lys Leu Trp Ser Asp Pro Asp Thr Phe Asp Pro Glu Arg
            420                 425                 430

Phe Ile Ala Thr Asp Ile Asp Phe Arg Gly Gln Tyr Tyr Lys Tyr Ile
            435                 440                 445

Pro Phe Gly Ser Gly Arg Arg Ser Cys Ser Gly Met Thr Tyr Ala Leu
            450                 455                 460

Gln Val Glu His Leu Thr Met Ala His Leu Ile Gln Gly Phe Asn Tyr
465                 470                 475                 480

Arg Thr Pro Asn Asp Glu Pro Leu Asp Met Lys Glu Gly Ala Gly Ile
            485                 490                 495

Thr Ile Arg Lys Val Asn Pro Val Glu Leu Ile Ile Ala Pro Arg Leu
            500                 505                 510

Ala Pro Glu Leu Tyr
            515

<210> SEQ ID NO 17
<211> LENGTH: 517
<212> TYPE: PRT
<213> ORGANISM: Artificial sequence
<220> FEATURE:
<223> OTHER INFORMATION: Synthetic sequence: Protein sequence of CYP82E5
      nicotine demethylase

<400> SEQUENCE: 17

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 18
<211> LENGTH: 517
<212> TYPE: PRT
<213> ORGANISM: Artificial sequence
<220> FEATURE:
<223> OTHER INFORMATION: Synthetic sequence: Protein sequence of P72L
      variant of CYP82E5 nicotine demethylase

<400> SEQUENCE: 18

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
            50                  55                  60

Asp Leu Ala Asp Lys Tyr Gly Leu Val Phe Thr Phe Arg Leu Gly Leu

-continued

```
                65                  70                  75                  80
Pro Leu Val Leu Val Ser Ser Tyr Glu Ala Val Lys Asp Cys Phe
                    85                  90                  95

Ser Thr Asn Asp Ala Ile Phe Ser Asn Arg Pro Ala Phe Leu Tyr Gly
                    100                 105                 110

Glu Tyr Leu Gly Tyr Ser Asn Ala Met Leu Phe Leu Thr Lys Tyr Gly
                    115                 120                 125

Pro Tyr Trp Arg Lys Asn Arg Lys Leu Val Ile Gln Glu Val Leu Ser
                    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                    165                 170                 175

Ile Asn Leu Thr Asp Trp Leu Glu Glu Leu Asn Phe Gly Leu Ile Val
                    180                 185                 190

Lys Met Ile Ala Gly Lys Asn Tyr Glu Ser Gly Lys Gly Asp Glu Gln
                    195                 200                 205

Val Glu Arg Phe Arg Lys Ala Phe Lys Asp Phe Ile Ile Leu Ser Met
                210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                    245                 250                 255

Asp Ser Val Phe Gln Asn Trp Leu Glu Glu His Val Lys Lys Arg Glu
                    260                 265                 270

Lys Met Glu Val Asn Ala Gln Gly Asn Glu Gln Asp Phe Ile Asp Val
                275                 280                 285

Val Leu Ser Lys Met Ser Asn Glu Tyr Leu Asp Glu Gly Tyr Ser Arg
                290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                    325                 330                 335

Asn Gln His Ala Leu Lys Lys Ala Gln Glu Glu Ile Asp Lys Lys Val
                    340                 345                 350

Gly Lys Glu Arg Trp Val Glu Glu Ser Asp Ile Lys Asp Leu Val Tyr
                    355                 360                 365

Leu Gln Ala Ile Val Lys Glu Val Leu Arg Leu Tyr Pro Pro Gly Pro
                370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                    405                 410                 415

Arg Asp Pro Lys Leu Trp Ser Asn Pro Asp Lys Phe Asp Pro Glu Arg
                    420                 425                 430

Phe Phe Ala Asp Asp Ile Asp Tyr Arg Gly Gln His Tyr Glu Phe Ile
                    435                 440                 445

Pro Phe Gly Ser Gly Arg Arg Ser Cys Pro Gly Met Thr Tyr Ala Leu
                    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                    485                 490                 495
```

Thr Ile Arg Lys Val Asn Pro Val Glu Val Thr Ile Thr Ala Arg Leu
            500                 505                 510

Ala Pro Glu Leu Tyr
        515

<210> SEQ ID NO 19
<211> LENGTH: 517
<212> TYPE: PRT
<213> ORGANISM: Artificial sequence
<220> FEATURE:
<223> OTHER INFORMATION: Synthetic sequence: Protein sequence of L143F
      variant of CYP82E5 nicotine demethylase

<400> SEQUENCE: 19

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Phe Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
    275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn

```
                       325                 330                 335
Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 20
<211> LENGTH: 517
<212> TYPE: PRT
<213> ORGANISM: Artificial sequence
<220> FEATURE:
<223> OTHER INFORMATION: Synthetic sequence: Protein sequence of S174L
      variant of CYP82E5 nicotine demethylase

<400> SEQUENCE: 20

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
        130                 135                 140

Ala Ser Arg Leu Glu Lys Leu Lys His Val Arg Phe Gly Lys Ile Gln
145                 150                 155                 160
```

```
Thr Ser Ile Lys Ser Leu Tyr Thr Arg Ile Asp Gly Asn Leu Ser Thr
            165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
            245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 21
<211> LENGTH: 517
<212> TYPE: PRT
<213> ORGANISM: Artificial sequence
<220> FEATURE:
<223> OTHER INFORMATION: Synthetic sequence: Protein sequence of M224I
      variant of CYP82E5 nicotine demethylase

<400> SEQUENCE: 21
```

-continued

```
Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
            35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Ile
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415
```

```
Arg Asp Pro Lys Leu Trp Ser Asn Pro Asp Lys Phe Asp Pro Glu Arg
                420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
        450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 22
<211> LENGTH: 517
<212> TYPE: PRT
<213> ORGANISM: Artificial sequence
<220> FEATURE:
<223> OTHER INFORMATION: Synthetic sequence: Protein sequence of P235S
      variant of CYP82E5 nicotine demethylase

<400> SEQUENCE: 22

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Ser Leu Phe Lys Trp Val
225                 230                 235                 240

Asp Phe Gln Gly His Val Lys Ala Met Lys Arg Thr Phe Lys Asp Ile
                245                 250                 255
```

```
Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Pro Phe Gly Ser Gly Arg Arg Ser Cys Pro Gly Met Thr Tyr Ala Leu
    450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
        515

<210> SEQ ID NO 23
<211> LENGTH: 517
<212> TYPE: PRT
<213> ORGANISM: Artificial sequence
<220> FEATURE:
<223> OTHER INFORMATION: Synthetic sequence: Protein sequence of A410V
      variant of CYP82E5 nicotine demethylase

<400> SEQUENCE: 23

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
```

```
                85                 90                  95
Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
            115                 120                 125

Pro Tyr Trp Arg Lys Asn Arg Lys Leu Val Ile Gln Glu Val Leu Ser
130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
                195                 200                 205

Val Glu Arg Phe Arg Lys Ala Phe Lys Asp Phe Ile Ile Leu Ser Met
            210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
                260                 265                 270

Lys Met Glu Val Asn Ala Gln Gly Asn Glu Gln Asp Phe Ile Asp Val
                275                 280                 285

Val Leu Ser Lys Met Ser Asn Glu Tyr Leu Asp Glu Gly Tyr Ser Arg
            290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
                340                 345                 350

Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
            370                 375                 380

Leu Leu Val Pro His Glu Asn Val Glu Asp Cys Val Val Ser Gly Tyr
385                 390                 395                 400

His Ile Pro Lys Gly Thr Arg Leu Phe Val Asn Val Met Lys Leu Gln
                405                 410                 415

Arg Asp Pro Lys Leu Trp Ser Asn Pro Asp Lys Phe Asp Pro Glu Arg
                420                 425                 430

Phe Phe Ala Asp Asp Ile Asp Tyr Arg Gly Gln His Tyr Glu Phe Ile
            435                 440                 445

Pro Phe Gly Ser Gly Arg Arg Ser Cys Pro Gly Met Thr Tyr Ala Leu
            450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
                500                 505                 510
```

```
Ala Pro Glu Leu Tyr
        515

<210> SEQ ID NO 24
<211> LENGTH: 421
<212> TYPE: PRT
<213> ORGANISM: Artificial sequence
<220> FEATURE:
<223> OTHER INFORMATION: Synthetic sequence: Protein sequence of
      W422Stop variant of CYP82E5 nicotine demethylase

<400> SEQUENCE: 24

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270

Lys Met Glu Val Asn Ala Gln Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
```

```
                340                 345                 350
Gly Lys Glu Arg Trp Val Glu Glu Ser Asp Ile Lys Asp Leu Val Tyr
            355                 360                 365

Leu Gln Ala Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu
            420

<210> SEQ ID NO 25
<211> LENGTH: 517
<212> TYPE: PRT
<213> ORGANISM: Artificial sequence
<220> FEATURE:
<223> OTHER INFORMATION: Synthetic sequence: Protein sequence of P449L
      variant of CYP82E5 nicotine demethylase

<400> SEQUENCE: 25

Met Val Ser Pro Val Glu Ala Ile Val Gly Leu Val Thr Leu Thr Leu
1               5                   10                  15

Leu Phe Tyr Phe Leu Trp Pro Lys Lys Phe Gln Ile Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Gly Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Val Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Ser Asn Ala Met Leu Phe Leu Thr Lys Tyr Gly
        115                 120                 125

Pro Tyr Trp Arg Lys Asn Arg Lys Leu Val Ile Gln Glu Val Leu Ser
    130                 135                 140

Ala Ser Arg Leu Glu Lys Leu Lys His Val Arg Phe Gly Lys Ile Gln
145                 150                 155                 160

Thr Ser Ile Lys Ser Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Arg Glu
            260                 265                 270
```

```
Lys Met Glu Val Asn Ala Gln Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Ile Asp Lys Lys Val
            340                 345                 350

Gly Lys Glu Arg Trp Val Glu Glu Ser Asp Ile Lys Asp Leu Val Tyr
        355                 360                 365

Leu Gln Ala Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Asp Asp Ile Asp Tyr Arg Gly Gln His Tyr Glu Phe Ile
        435                 440                 445

Leu Phe Gly Ser Gly Arg Arg Ser Cys Pro Gly Met Thr Tyr Ala Leu
        450                 455                 460

Gln Ala Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Val Glu Val Thr Ile Thr Ala Arg Leu
            500                 505                 510

Ala Pro Glu Leu Tyr
            515

<210> SEQ ID NO 26
<211> LENGTH: 517
<212> TYPE: PRT
<213> ORGANISM: Artificial sequence
<220> FEATURE:
<223> OTHER INFORMATION: Synthetic sequence: Protein sequence of
      CYP82E10 nicotine demethylase

<400> SEQUENCE: 26

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110
```

```
Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515
```

<210> SEQ ID NO 27
<211> LENGTH: 517
<212> TYPE: PRT
<213> ORGANISM: Artificial sequence
<220> FEATURE:
<223> OTHER INFORMATION: Synthetic sequence: Protein sequence of L148F variant of CYP82E10 nicotine demethylase

<400> SEQUENCE: 27

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Phe Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365
```

```
Leu Gln Thr Ile Val Lys Glu Val Leu Arg Leu Tyr Pro Pro Gly Pro
        370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
        450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
            515

<210> SEQ ID NO 28
<211> LENGTH: 517
<212> TYPE: PRT
<213> ORGANISM: Artificial sequence
<220> FEATURE:
<223> OTHER INFORMATION: Synthetic sequence: Protein sequence of G172R
      variant of CYP82E10 nicotine demethylase

<400> SEQUENCE: 28

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Arg Asn Ser Ser Thr
                165                 170                 175

Ile Asn Leu Thr Asp Trp Leu Glu Glu Leu Asn Phe Gly Leu Ile Val
                180                 185                 190

Lys Met Ile Ala Gly Lys Asn Tyr Glu Ser Gly Lys Gly Asp Glu Gln
```

```
            195                 200                 205
Val Glu Arg Phe Arg Lys Ala Phe Lys Asp Phe Ile Ile Leu Ser Met
210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 29
<211> LENGTH: 517
<212> TYPE: PRT
<213> ORGANISM: Artificial sequence
<220> FEATURE:
<223> OTHER INFORMATION: Synthetic sequence: Protein sequence of A344T
      variant of CYP82E10 nicotine demethylase

<400> SEQUENCE: 29

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30
```

-continued

```
Leu Pro Pro Lys Ile Pro Gly Gly Trp Pro Val Ile His Leu Phe
         35                  40                  45

Tyr Phe Asp Asp Ser Asp Asp Arg Pro Leu Ala Arg Lys Leu Gly
 50                  55                  60

Asp Leu Ala Asp Lys Tyr Gly Pro Val Phe Thr Phe Arg Leu Gly Leu
 65                  70                  75                  80

Pro Leu Val Leu Val Val Ser Ser Tyr Glu Ala Ile Lys Asp Cys Phe
                 85                  90                  95

Ser Thr Asn Asp Ala Ile Phe Ser Asn Arg Pro Ala Phe Leu Tyr Gly
             100                 105                 110

Glu Tyr Leu Gly Tyr Asn Asn Ala Met Leu Phe Leu Thr Lys Tyr Gly
         115                 120                 125

Pro Tyr Trp Arg Lys Asn Arg Lys Leu Val Ile Gln Glu Val Leu Cys
     130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                 165                 170                 175

Ile Asn Leu Thr Asp Trp Leu Glu Glu Leu Asn Phe Gly Leu Ile Val
             180                 185                 190

Lys Met Ile Ala Gly Lys Asn Tyr Glu Ser Gly Lys Gly Asp Glu Gln
         195                 200                 205

Val Glu Arg Phe Arg Lys Ala Phe Lys Asp Phe Ile Ile Leu Ser Met
     210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                 245                 250                 255

Asp Ser Val Phe Gln Asn Trp Leu Glu Glu His Val Lys Lys Lys Glu
             260                 265                 270

Lys Met Glu Val Asn Ala Glu Gly Asn Glu Gln Asp Phe Ile Asp Val
         275                 280                 285

Val Leu Ser Lys Met Ser Asn Glu Tyr Leu Asp Glu Gly Tyr Ser Arg
     290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                 325                 330                 335

Asn Gln His Ala Leu Lys Lys Thr Gln Glu Glu Ile Asp Lys Lys Val
             340                 345                 350

Gly Lys Asp Arg Trp Val Glu Glu Ser Asp Ile Lys Asp Leu Val Tyr
         355                 360                 365

Leu Gln Thr Ile Val Lys Glu Val Leu Arg Leu Tyr Pro Pro Gly Pro
     370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                 405                 410                 415

Arg Asp Pro Lys Leu Trp Ser Asn Pro Asp Lys Phe Asp Pro Glu Arg
             420                 425                 430

Phe Phe Ala Ala Asp Ile Asp Phe Arg Gly Gln His Tyr Glu Phe Ile
         435                 440                 445

Pro Phe Gly Ser Gly Arg Arg Ser Cys Pro Gly Met Thr Tyr Ala Met
```

450                 455                 460
Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
                500                 505                 510

Thr Pro Glu Leu Tyr
            515

<210> SEQ ID NO 30
<211> LENGTH: 517
<212> TYPE: PRT
<213> ORGANISM: Artificial sequence
<220> FEATURE:
<223> OTHER INFORMATION: Synthetic sequence: Protein sequence of A410T
      variant of CYP82E10 nicotine demethylase

<400> SEQUENCE: 30

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Ser Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

-continued

```
Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
                340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Pro Pro Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Thr Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
                435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 31
<211> LENGTH: 517
<212> TYPE: PRT
<213> ORGANISM: Artificial sequence
<220> FEATURE:
<223> OTHER INFORMATION: Synthetic sequence: Protein sequence of R417H
      variant of CYP82E10 nicotine demethylase

<400> SEQUENCE: 31

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Asp Ser Asp Asp Arg Pro Leu Ala Arg Lys Leu Gly
        50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125
```

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

His Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 32
<211> LENGTH: 517

<212> TYPE: PRT
<213> ORGANISM: Artificial sequence
<220> FEATURE:
<223> OTHER INFORMATION: Synthetic sequence: Protein sequence of P419S
      variant of CYP82E10 nicotine demethylase

<400> SEQUENCE: 32

```
Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Arg Pro Leu Ala Arg Lys Leu Gly
    50                  55                  60

Asp Leu Ala Asp Lys Tyr Gly Pro Val Phe Thr Phe Arg Leu Gly Leu
65                  70                  75                  80

Pro Leu Val Leu Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
        130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380
```

```
Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Ser Lys Leu Trp Ser Asn Pro Asp Lys Phe Asp Pro Glu Arg
        420                 425                 430

Phe Phe Ala Ala Asp Ile Asp Phe Arg Gly Gln His Tyr Glu Phe Ile
    435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 33
<211> LENGTH: 517
<212> TYPE: PRT
<213> ORGANISM: Artificial sequence
<220> FEATURE:
<223> OTHER INFORMATION: Synthetic sequence: Protein sequence of G79S
      variant of CYP82E10 nicotine demethylase

<400> SEQUENCE: 33

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
            20                  25                  30

Leu Pro Pro Lys Ile Pro Gly Gly Trp Pro Val Ile Gly His Leu Phe
        35                  40                  45

Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Ser Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
            100                 105                 110

Glu Tyr Leu Gly Tyr Asn Asn Ala Met Leu Phe Leu Thr Lys Tyr Gly
        115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
```

```
        210                 215                 220
Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu His Val Lys Lys Lys Glu
                260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
        290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
        355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
        435                 440                 445

Pro Phe Gly Ser Gly Arg Arg Ser Cys Pro Gly Met Thr Tyr Ala Met
    450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
                485                 490                 495

Thr Ile Arg Lys Val Asn Pro Ile Glu Val Val Ile Thr Pro Arg Leu
            500                 505                 510

Thr Pro Glu Leu Tyr
        515

<210> SEQ ID NO 34
<211> LENGTH: 517
<212> TYPE: PRT
<213> ORGANISM: Artificial sequence
<220> FEATURE:
<223> OTHER INFORMATION: Synthetic sequence: Protein sequence of P107S
      variant of CYP82E10 nicotine demethylase

<400> SEQUENCE: 34

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45
```

```
Tyr Phe Asp Asp Asp Ser Asp Asp Arg Pro Leu Ala Arg Lys Leu Gly
    50                  55                  60

Asp Leu Ala Asp Lys Tyr Gly Pro Val Phe Thr Phe Arg Leu Gly Leu
65              70                  75                      80

Pro Leu Val Leu Val Val Ser Ser Tyr Glu Ala Ile Lys Asp Cys Phe
                85                  90                  95

Ser Thr Asn Asp Ala Ile Phe Ser Asn Arg Ser Ala Phe Leu Tyr Gly
            100                 105                 110

Glu Tyr Leu Gly Tyr Asn Asn Ala Met Leu Phe Leu Thr Lys Tyr Gly
                115                 120                 125

Pro Tyr Trp Arg Lys Asn Arg Lys Leu Val Ile Gln Glu Val Leu Cys
    130                 135                 140

Ala Ser Arg Leu Glu Lys Leu Lys His Val Arg Phe Gly Glu Ile Gln
145             150                 155                     160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
            195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
            275                 280                 285

Val Leu Ser Lys Met Ser Asn Glu Tyr Leu Asp Glu Gly Tyr Ser Arg
    290                 295                 300

Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
                325                 330                 335

Asn Gln His Ala Leu Lys Lys Ala Gln Glu Glu Ile Asp Lys Lys Val
            340                 345                 350

Gly Lys Asp Arg Trp Val Glu Glu Ser Asp Ile Lys Asp Leu Val Tyr
            355                 360                 365

Leu Gln Thr Ile Val Lys Glu Val Leu Arg Leu Tyr Pro Pro Gly Pro
    370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
                405                 410                 415

Arg Asp Pro Lys Leu Trp Ser Asn Pro Asp Lys Phe Asp Pro Glu Arg
            420                 425                 430

Phe Phe Ala Ala Asp Ile Asp Phe Arg Gly Gln His Tyr Glu Phe Ile
            435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
```

```
                465                 470                 475                 480
Lys Thr Pro Asn Asp Glu Pro Leu Asp Met Lys Glu Gly Ala Gly Leu
                    485                 490                 495

Thr Ile Arg Lys Val Asn Pro Ile Glu Val Val Ile Thr Pro Arg Leu
                    500                 505                 510

Thr Pro Glu Leu Tyr
            515

<210> SEQ ID NO 35
<211> LENGTH: 517
<212> TYPE: PRT
<213> ORGANISM: Artificial sequence
<220> FEATURE:
<223> OTHER INFORMATION: Synthetic sequence: Protein sequence of P382S
      variant of CYP82E10 nicotine demethylase

<400> SEQUENCE: 35

Met Val Ser Pro Val Glu Ala Ile Val Gly Leu Val Thr Leu Thr Leu
1               5                   10                  15

Leu Phe Tyr Phe Ile Arg Thr Lys Lys Ser Gln Lys Pro Ser Lys Pro
                20                  25                  30

Leu Pro Pro Lys Ile Pro Gly Gly Trp Pro Val Ile Gly His Leu Phe
            35                  40                  45

Tyr Phe Asp Asp Ser Asp Asp Arg Pro Leu Ala Arg Lys Leu Gly
50                  55                  60

Asp Leu Ala Asp Lys Tyr Gly Pro Val Phe Thr Phe Arg Leu Gly Leu
65                  70                  75                  80

Pro Leu Val Leu Val Val Ser Ser Tyr Glu Ala Ile Lys Asp Cys Phe
                85                  90                  95

Ser Thr Asn Asp Ala Ile Phe Ser Asn Arg Pro Ala Phe Leu Tyr Gly
                100                 105                 110

Glu Tyr Leu Gly Tyr Asn Asn Ala Met Leu Phe Leu Thr Lys Tyr Gly
            115                 120                 125

Pro Tyr Trp Arg Lys Asn Arg Lys Leu Val Ile Gln Glu Val Leu Cys
130                 135                 140

Ala Ser Arg Leu Glu Lys Leu Lys His Val Arg Phe Gly Glu Ile Gln
145                 150                 155                 160

Thr Ser Ile Lys Asn Leu Tyr Thr Arg Ile Asp Gly Asn Ser Ser Thr
                165                 170                 175

Ile Asn Leu Thr Asp Trp Leu Glu Glu Leu Asn Phe Gly Leu Ile Val
            180                 185                 190

Lys Met Ile Ala Gly Lys Asn Tyr Glu Ser Gly Lys Gly Asp Glu Gln
        195                 200                 205

Val Glu Arg Phe Arg Lys Ala Phe Lys Asp Phe Ile Ile Leu Ser Met
    210                 215                 220

Glu Phe Val Leu Trp Asp Ala Phe Pro Ile Pro Leu Phe Lys Trp Val
225                 230                 235                 240

Asp Phe Gln Gly His Val Lys Ala Met Lys Arg Thr Phe Lys Asp Ile
                245                 250                 255

Asp Ser Val Phe Gln Asn Trp Leu Glu Glu His Val Lys Lys Lys Glu
            260                 265                 270

Lys Met Glu Val Asn Ala Glu Gly Asn Glu Gln Asp Phe Ile Asp Val
        275                 280                 285

Val Leu Ser Lys Met Ser Asn Glu Tyr Leu Asp Glu Gly Tyr Ser Arg
    290                 295                 300
```

-continued

```
Asp Thr Val Ile Lys Ala Thr Val Phe Ser Leu Val Leu Asp Ala Ala
305                 310                 315                 320

Asp Thr Val Ala Leu His Met Asn Trp Gly Met Ala Leu Leu Ile Asn
            325                 330                 335

Asn Gln His Ala Leu Lys Lys Ala Gln Glu Glu Ile Asp Lys Lys Val
        340                 345                 350

Gly Lys Asp Arg Trp Val Glu Glu Ser Asp Ile Lys Asp Leu Val Tyr
    355                 360                 365

Leu Gln Thr Ile Val Lys Glu Val Leu Arg Leu Tyr Pro Ser Gly Pro
370                 375                 380

Leu Leu Val Pro His Glu Asn Val Glu Asp Cys Val Val Ser Gly Tyr
385                 390                 395                 400

His Ile Pro Lys Gly Thr Arg Leu Phe Ala Asn Val Met Lys Leu Gln
            405                 410                 415

Arg Asp Pro Lys Leu Trp Ser Asn Pro Asp Lys Phe Asp Pro Glu Arg
        420                 425                 430

Phe Phe Ala Ala Asp Ile Asp Phe Arg Gly Gln His Tyr Glu Phe Ile
    435                 440                 445

Pro Phe Gly Ser Gly Arg Arg Ser Cys Pro Gly Met Thr Tyr Ala Met
450                 455                 460

Gln Val Glu His Leu Thr Ile Ala His Leu Ile Gln Gly Phe Asn Tyr
465                 470                 475                 480

Lys Thr Pro Asn Asp Glu Pro Leu Asp Met Lys Glu Gly Ala Gly Leu
            485                 490                 495

Thr Ile Arg Lys Val Asn Pro Ile Glu Val Val Ile Thr Pro Arg Leu
        500                 505                 510

Thr Pro Glu Leu Tyr
        515
```

<210> SEQ ID NO 36
<211> LENGTH: 24
<212> TYPE: DNA
<213> ORGANISM: Artificial sequence
<220> FEATURE:
<223> OTHER INFORMATION: Synthetic primer NND3_F1

<400> SEQUENCE: 36
ttgatccagg gtttcaatta cagc                                        24

<210> SEQ ID NO 37
<211> LENGTH: 28
<212> TYPE: DNA
<213> ORGANISM: Artificial sequence
<220> FEATURE:
<223> OTHER INFORMATION: Synthetic primer NND3_R2

<400> SEQUENCE: 37
aacgtaccaa attagaaaaa cgtgtacc                                    28

<210> SEQ ID NO 38
<211> LENGTH: 31
<212> TYPE: DNA
<213> ORGANISM: Artificial sequence
<220> FEATURE:
<223> OTHER INFORMATION: Synthetic primer E4_F1

<400> SEQUENCE: 38
ttttcagaat tggttagagg aacatattaa t                                31

```
<210> SEQ ID NO 39
<211> LENGTH: 26
<212> TYPE: DNA
<213> ORGANISM: Artificial sequence
<220> FEATURE:
<223> OTHER INFORMATION: Synthetic primer E4_R1

<400> SEQUENCE: 39
tgtgtctatc tcttcttgtg ctttcg                                          26

<210> SEQ ID NO 40
<211> LENGTH: 29
<212> TYPE: DNA
<213> ORGANISM: Artificial sequence
<220> FEATURE:
<223> OTHER INFORMATION: Synthetic primer E5_F1

<400> SEQUENCE: 40
agagattctt cgctgatgat attgactac                                       29

<210> SEQ ID NO 41
<211> LENGTH: 29
<212> TYPE: DNA
<213> ORGANISM: Artificial sequence
<220> FEATURE:
<223> OTHER INFORMATION: Synthetic primer E5_R1

<400> SEQUENCE: 41
ccgtaattgt cacttctaca ggatttact                                       29

<210> SEQ ID NO 42
<211> LENGTH: 24
<212> TYPE: DNA
<213> ORGANISM: Artificial sequence
<220> FEATURE:
<223> OTHER INFORMATION: Synthetic primer E10_F2

<400> SEQUENCE: 42
gctgatattg actttcgtgg tcaa                                            24

<210> SEQ ID NO 43
<211> LENGTH: 24
<212> TYPE: DNA
<213> ORGANISM: Artificial sequence
<220> FEATURE:
<223> OTHER INFORMATION: Synthetic primer E10_R2

<400> SEQUENCE: 43
gcgaggcgta attaccactt ctat                                            24

<210> SEQ ID NO 44
<211> LENGTH: 24
<212> TYPE: DNA
<213> ORGANISM: Artificial sequence
<220> FEATURE:
<223> OTHER INFORMATION: Synthetic primer PQ0014_F

<400> SEQUENCE: 44
ctattctccg ctttggactt ggca                                            24

<210> SEQ ID NO 45
<211> LENGTH: 23
<212> TYPE: DNA
<213> ORGANISM: Artificial sequence
<220> FEATURE:
<223> OTHER INFORMATION: Synthetic primer PQ0014_R
```

```
<400> SEQUENCE: 45
aggacctcag gacaacggaa acg                                            23

<210> SEQ ID NO 46
<211> LENGTH: 27
<212> TYPE: DNA
<213> ORGANISM: Artificial sequence
<220> FEATURE:
<223> OTHER INFORMATION: Synthetic primer NND3_F6

<400> SEQUENCE: 46
aattttggtc tcatcgtgaa gatgata                                        27

<210> SEQ ID NO 47
<211> LENGTH: 27
<212> TYPE: DNA
<213> ORGANISM: Artificial sequence
<220> FEATURE:
<223> OTHER INFORMATION: Synthetic primer NND3_R7

<400> SEQUENCE: 47
tcactctctt ctacccatct atccttg                                        27
```